(12) United States Patent
Hastings et al.

(10) Patent No.: US 11,938,309 B2
(45) Date of Patent: Mar. 26, 2024

(54) HYPODERMIC INTERFACE ASSEMBLY

(71) Applicant: Neogen Corporation, Lansing, MI (US)

(72) Inventors: Gregory S. Hastings, Richmond, KY (US); Bradley E. Galbreath, Lexington, KY (US); Nicholas J. Wagner, Lexington, KY (US); Taylor Kopacka Leigh, Alpharetta, GA (US); Peter Wyndham Shipp, Jr., Woodstock, GA (US); Jason Lye, Atlanta, GA (US); Randall M. Bachtel, Lawrenceville, GA (US); Dexter E. Jacobs, Austin, TX (US); Michael Trovato, Portland, OR (US)

(73) Assignee: NEOGEN CORPORATION, Lansing, MI (US)

( * ) Notice: Subject to any disclaimer, the term of this patent is extended or adjusted under 35 U.S.C. 154(b) by 130 days.

(21) Appl. No.: 16/947,305

(22) Filed: Jul. 28, 2020

(65) Prior Publication Data

US 2022/0031961 A1 Feb. 3, 2022

(51) Int. Cl.
*A61M 5/32* (2006.01)
*A61M 5/31* (2006.01)
*A61M 5/34* (2006.01)

(52) U.S. Cl.
CPC ........ *A61M 5/3293* (2013.01); *A61M 5/3134* (2013.01); *A61M 5/349* (2013.01); *A61M 2205/583* (2013.01)

(58) Field of Classification Search
CPC .... A61M 5/349; A61M 5/3293; A61M 5/343; A61M 2005/3206; A61M 5/3205
See application file for complete search history.

(56) References Cited

U.S. PATENT DOCUMENTS

| | | | | |
|---|---|---|---|---|
| 1,272,104 A | * | 7/1918 | Riethmueller | A61M 5/46 604/117 |
| 1,465,851 A | * | 8/1923 | Kress | A61M 5/32 604/273 |
| 1,503,399 A | * | 7/1924 | Webb | A61M 5/32 604/273 |
| 2,034,294 A | | 3/1936 | Hein | |
| 2,091,438 A | * | 8/1937 | Casper | A61M 5/46 604/117 |
| 3,096,763 A | | 7/1963 | McConnaughey et al. | |

(Continued)

FOREIGN PATENT DOCUMENTS

| AU | 2001226596 B2 | 8/2001 |
|---|---|---|
| CA | 2416723 A1 | 5/2002 |

(Continued)

OTHER PUBLICATIONS

U.S. Appl. No. 16/947,306, filed Jul. 28, 2020, Hastings et al., Pending.

(Continued)

*Primary Examiner* — Emily L Schmidt
(74) *Attorney, Agent, or Firm* — Honigman LLP; Douglas H. Siegel; Jonathan P. O'Brien

(57) ABSTRACT

A hypodermic interface assembly is disclosed. The hypodermic interface assembly includes a hub, a cannula, and a cannula carrier. The cannula carrier is non-removably-connected to the cannula. The cannula carrier is controllably separable from the hub.

26 Claims, 55 Drawing Sheets

(56) References Cited

U.S. PATENT DOCUMENTS

| | | |
|---|---|---|
| 3,216,616 A | 11/1965 | Blankenship, Jr. |
| 3,320,954 A | 5/1967 | Cowley |
| 3,472,227 A | 10/1969 | Burke |
| 3,517,668 A | 6/1970 | Brickson |
| 3,540,447 A | 11/1970 | Howe et al. |
| 3,884,230 A | 5/1975 | Wulff |
| 3,994,295 A | 11/1976 | Wulff |
| 4,335,718 A | 6/1982 | Calabrese |
| 4,508,534 A | 4/1985 | Garver, Sr. et al. |
| 5,405,330 A | 4/1995 | Zunitch et al. |
| 5,829,589 A | 11/1998 | Nguyen et al. |
| 6,488,668 B1 | 12/2002 | Prindle |
| 6,595,960 B2 | 7/2003 | West et al. |
| 6,599,276 B1 | 7/2003 | Humphrey |
| 6,960,196 B2 | 11/2005 | Prindle |
| 7,905,869 B2 | 3/2011 | Prindle |
| 9,174,000 B2 | 11/2015 | Bode |
| 9,446,190 B2 | 9/2016 | Miller |
| 9,675,789 B2 | 6/2017 | Chen et al. |
| 2003/0009137 A1 | 1/2003 | Klint et al. |
| 2004/0064109 A1 | 4/2004 | Klint et al. |
| 2005/0049560 A1 | 3/2005 | Hauri |
| 2005/0177117 A1 | 8/2005 | Crocker et al. |
| 2009/0312715 A1 | 12/2009 | Monson et al. |
| 2012/0123334 A1* | 5/2012 | Schraga ............ A61M 5/3213 604/111 |
| 2012/0179115 A1 | 7/2012 | Horvath et al. |
| 2013/0267904 A1 | 10/2013 | Limaye et al. |
| 2015/0032060 A1 | 1/2015 | Patel |
| 2018/0021526 A1* | 1/2018 | Sullivan ............ A61M 5/3293 604/506 |
| 2018/0333544 A1* | 11/2018 | Ploch ............ A61M 5/345 |
| 2022/0031961 A1 | 2/2022 | Hastings et al. |
| 2022/0062563 A1 | 3/2022 | Hastings et al. |

FOREIGN PATENT DOCUMENTS

| | | |
|---|---|---|
| CN | 201161027 | 12/2008 |
| CN | 201161027 Y | 12/2008 |
| EP | 1333876 B1 | 7/2001 |
| EP | 1253961 B1 | 6/2004 |
| KR | 1020120042604 A | 5/2012 |
| WO | WO2004037325 A1 | 5/2004 |
| WO | WO2006045215 A1 | 4/2006 |
| WO | WO2009079872 A1 | 2/2009 |
| WO | WO2009079880 A1 | 2/2009 |

OTHER PUBLICATIONS

U.S. Appl. No. 17/008,936, filed Sep. 1, 2020, Hastings et al., Pending.

International Search Report & Written Opinion for PCT/US2020/048892 dated Nov. 13, 2020.

International Search Report & Written Opinion for PCT/US2020/070314 dated Oct. 5, 2020.

International Search Report and Written Opinion for PCT/US20/70316 dated Oct. 9, 2020.

International Search Report & Written Opinion for PCT/US2022/046975 dated Feb. 10, 2023.

* cited by examiner

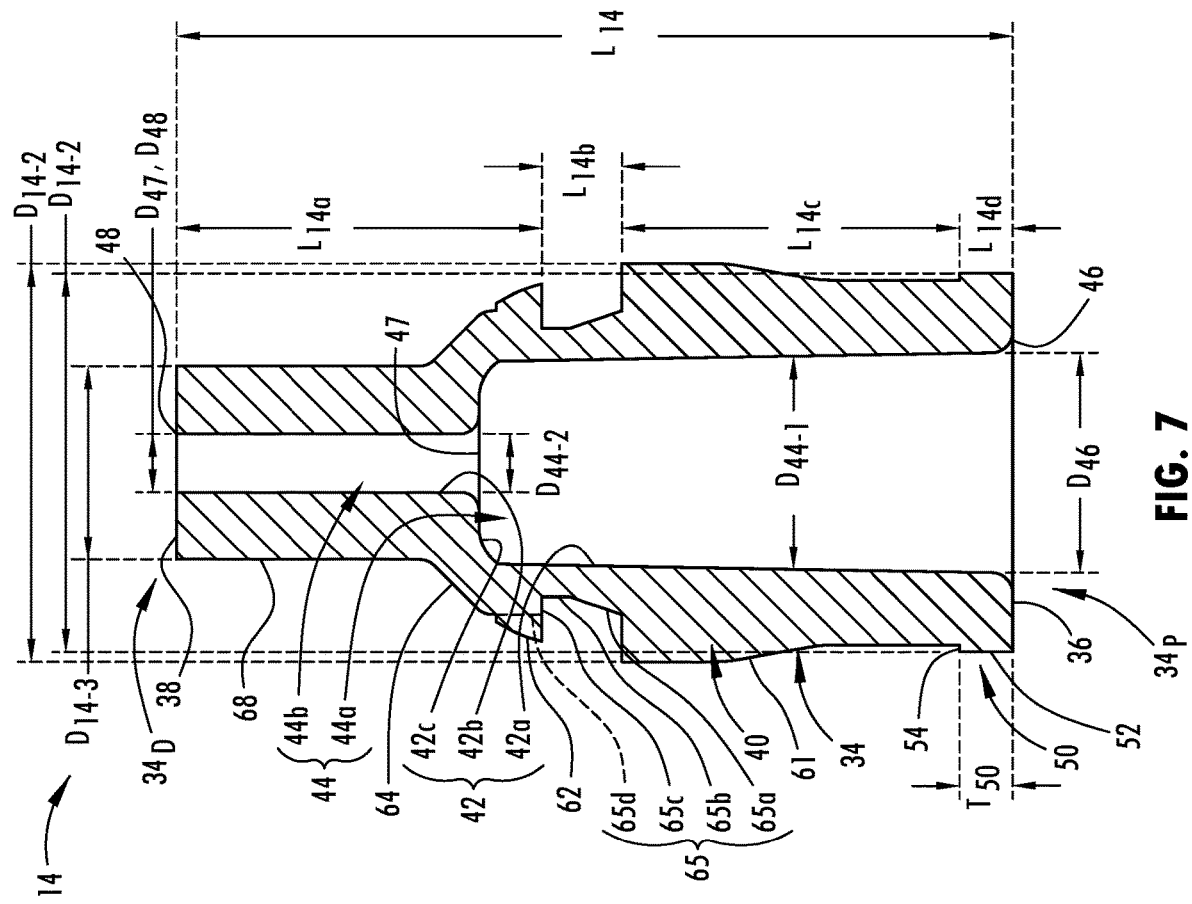
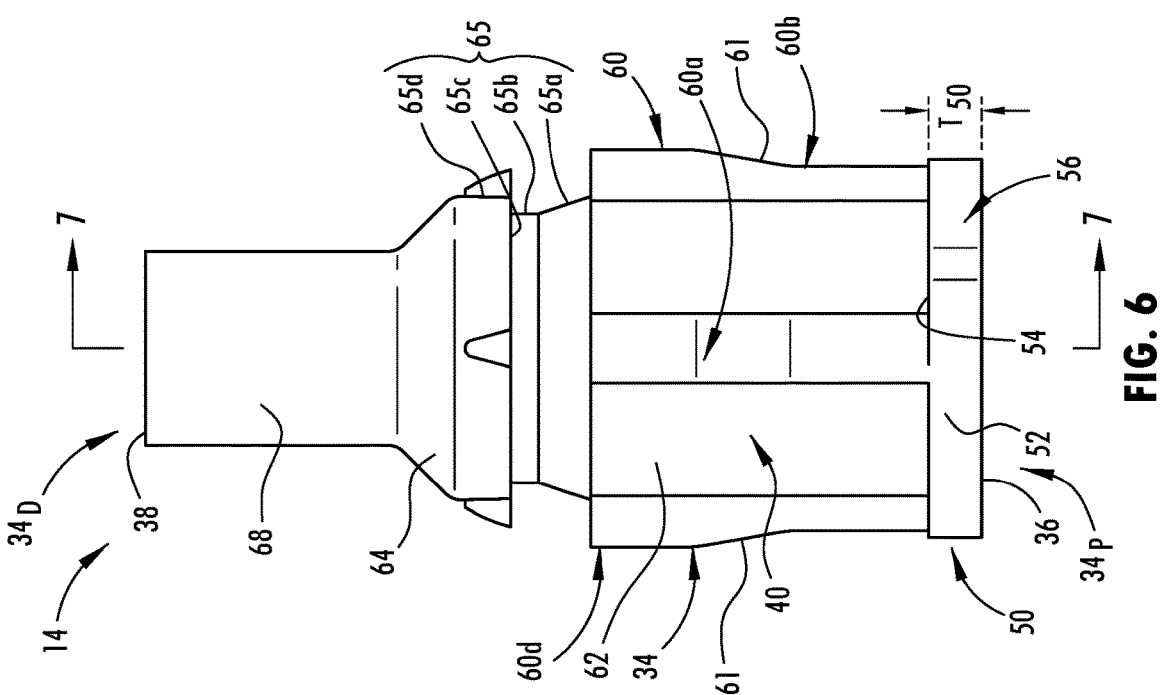

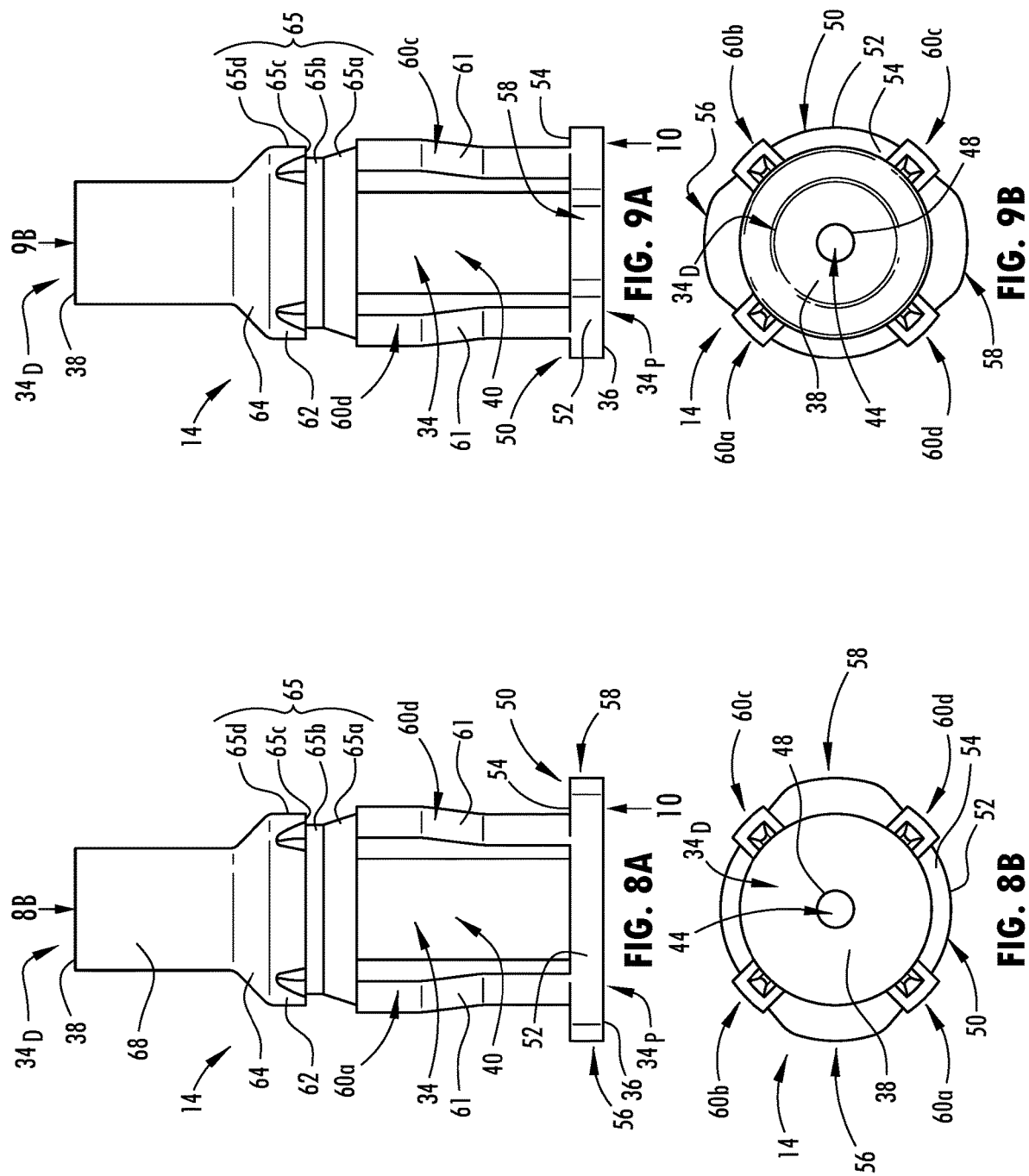

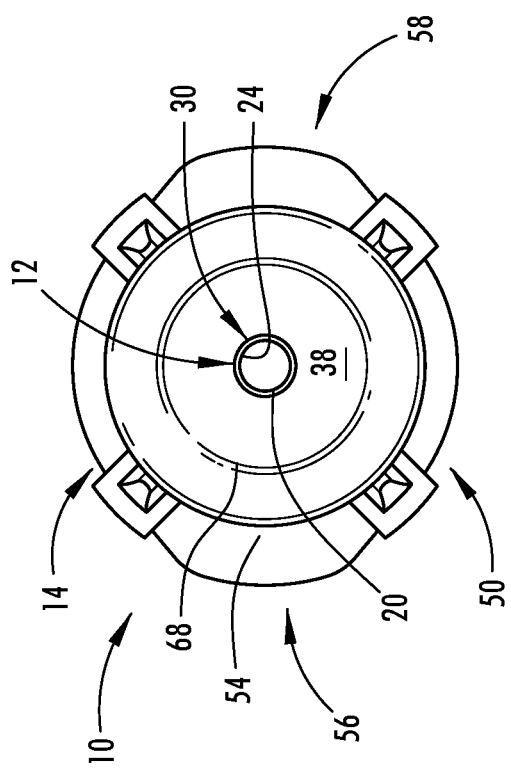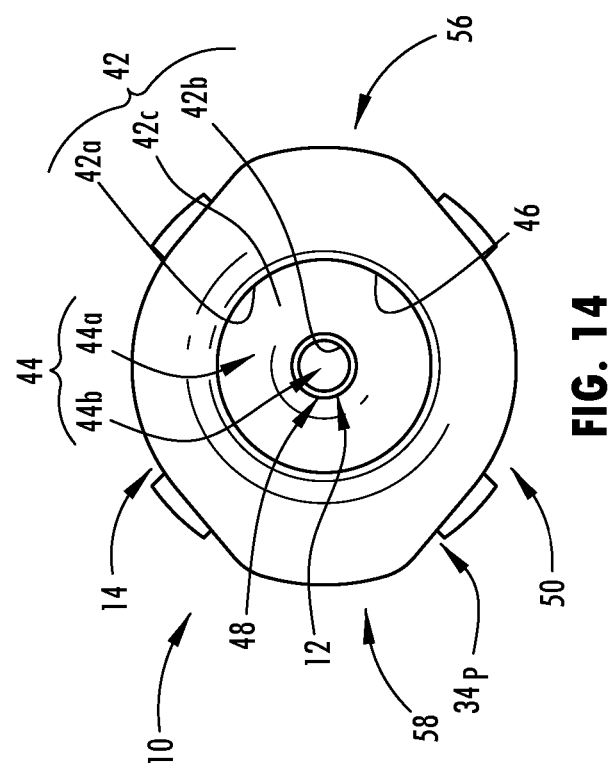

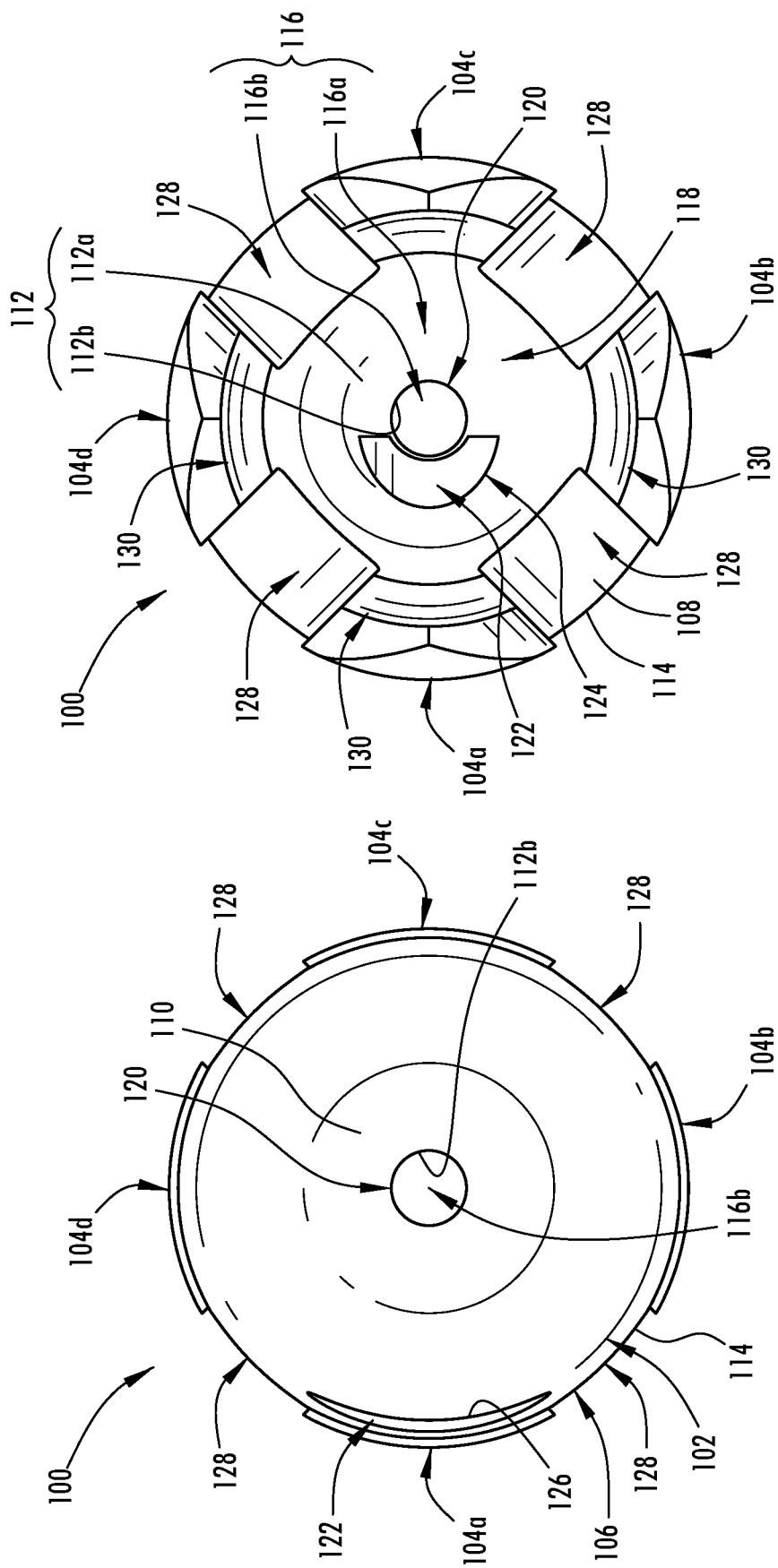

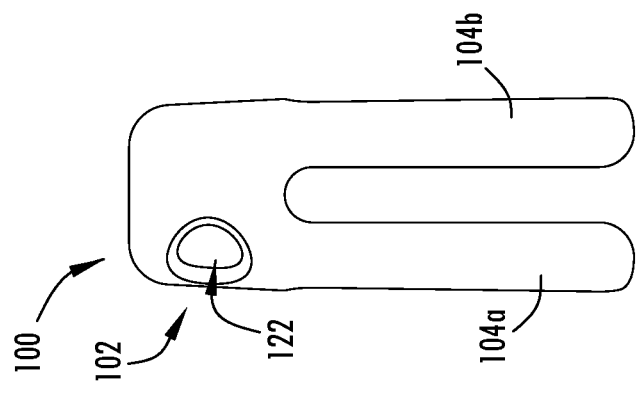
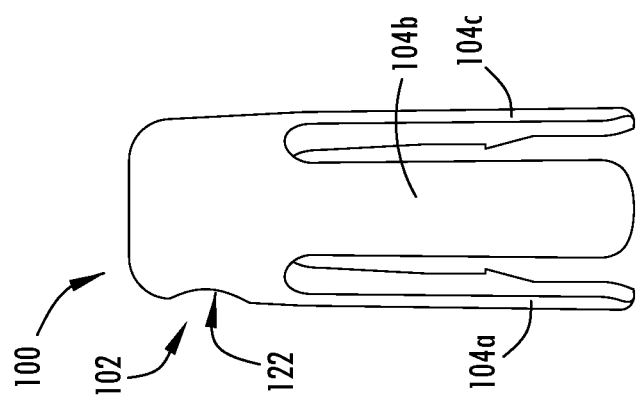
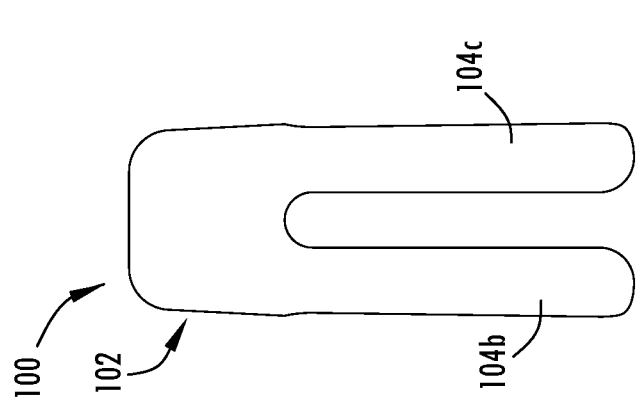
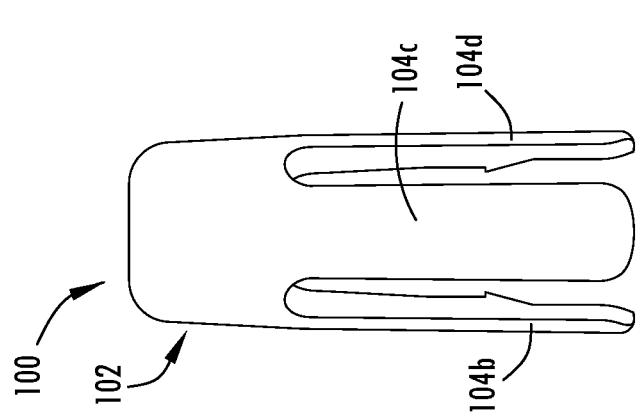
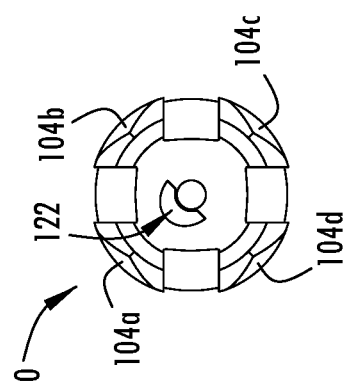
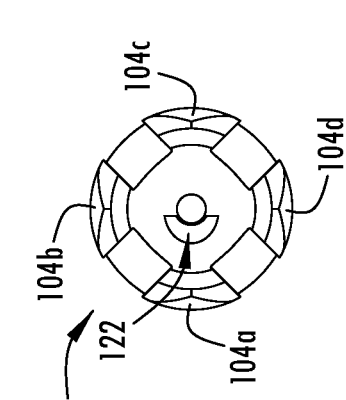
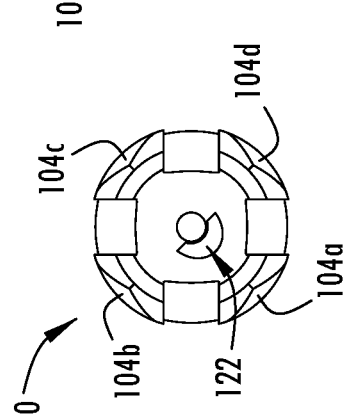
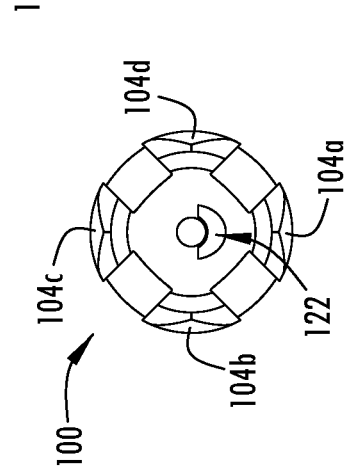

HYPODERMIC INTERFACE ASSEMBLY

TECHNICAL FIELD

The disclosure relates generally to hypodermic interface assemblies.

BACKGROUND

This section provides background information related to the present disclosure and is not necessarily prior art.

While known hypodermic interface assemblies have proven to be acceptable for various applications, such hypodermic interface assemblies are nevertheless susceptible to improvements that may enhance their overall performance and cost. Therefore, a need exists to develop hypodermic interface assemblies that advance the art.

SUMMARY

This section provides a general summary of the disclosure, and is not a comprehensive disclosure of its full scope or all of its features.

In one aspect, the invention provides a hypodermic interface assembly which may include a hub; a cannula; and a cannula carrier, wherein the cannula carrier is non-removably connected to the cannula, and the cannula carrier is controllably separable from the hub. In a further embodiment, the hypodermic interface assembly also may include an adhesive connecting the cannula to the cannula carrier. In yet another embodiment of the hypodermic interface assembly, the cannula carrier may include an adhesive-depositing passage, and the adhesive may be deposited into the adhesive-depositing passage of the cannula carrier.

In one embodiment of the hypodermic interface assembly of the present invention, the cannula carrier may include at least one leg portion; further, the at least one leg portion of the cannula carrier may include a barb portion, and the hub may include a groove that is sized to receive the barb portion of the at least one leg portion.

In an embodiment of the present invention, the cannula of the hypodermic interface assembly may be disposed within a hub passage extending through the hub and a cannula carrier passage extending through the cannula carrier. In another embodiment, an outer surface of the cannula may be secured to an inner surface that defines the hub passage.

In another aspect of the hypodermic interface assembly, a first portion of an outer surface of the cannula may be arranged in a spaced-apart relationship with respect to a first inner surface portion that defines a first cannula carrier passage portion of the cannula carrier passage of the cannula carrier, and a second portion of the outer surface of the cannula may be disposed adjacent a second inner surface portion that defines a second cannula carrier passage portion of the cannula carrier passage of the cannula carrier for fluidly-sealing the second cannula carrier passage portion of the cannula carrier passage of the cannula carrier. Further, the cannula carrier may include a head portion defined by a body and at least one leg portion.

In another aspect, the invention provides a hypodermic interface assembly including (a) a first hypodermic interface assembly portion that is defined by a hub; and (b) a second hypodermic interface assembly portion that is separably-connected to the first hypodermic interface assembly portion, wherein the second hypodermic interface assembly portion is defined by (i) a cannula and (ii) a cannula carrier non-removably-connected to the cannula, wherein the cannula carrier is controllably separable from the hub. The hypodermic interface assembly may further include an adhesive connecting the cannula to the cannula carrier. In yet another aspect, the cannula carrier may include an adhesive-depositing passage, and the adhesive may be deposited into the adhesive-depositing passage of the cannula carrier.

In another embodiment of the hypodermic interface assembly of the present invention, the cannula carrier may include at least one leg portion. Further, the at least one leg portion of the cannula carrier may include a barb portion, and the hub may include a groove that is sized to receive the barb portion of the at least one leg portion.

In yet another embodiment, the cannula of the hypodermic interface assembly may be disposed within a hub passage extending through the hub and a cannula carrier passage extending through the cannula carrier. Further, an outer surface of the cannula may be secured to an inner surface that defines the hub passage.

In an further embodiment of the hypodermic interface assembly, a first portion of an outer surface of the cannula may be arranged in a spaced-apart relationship with respect to a first inner surface portion that defines a first cannula carrier passage portion of the cannula carrier passage of the cannula carrier, and a second portion of the outer surface of the cannula may be disposed adjacent a second inner surface portion that defines a second cannula carrier passage portion of the cannula carrier passage of the cannula carrier for fluidly-sealing the second cannula carrier passage portion of the cannula carrier passage of the cannula carrier. Further, the cannula carrier may include a head portion defined by a body and at least one leg portion.

A further embodiment of the invention is a method including (a) providing a cannula carrier, a cannula, and a hub; (b) non-separably joining the cannula carrier to the cannula; and (c) joining the cannula carrier to the hub, wherein the cannula carrier is controllably separable from the hub. The method also may include separably joining the hub to an injection gun, and inserting the cannula into the flesh of a subject. Additional method steps may include subjecting one or both of the cannula and the cannula carrier to one or more radial forces relative to a central axis extending through the cannula and the cannula carrier for mechanically-separating the cannula carrier from the hub whereby (i) the hub remains separably joined to the injection gun, (ii) the cannula is removably disposed within the flesh of the subject, and (iii) the cannula carrier is disposed adjacent an outer surface of the flesh of the subject.

In another embodiment, the inventive method may include locating the cannula carrier that is disposed adjacent the outer surface of the flesh of the subject; grasping the cannula carrier; and applying a force to the cannula carrier to remove the cannula from the flesh of the subject. A further method step may include separating the hub from the injection gun. Additionally, the cannula carrier may include a high visibility dye or pigment. In another embodiment, the subjecting step may result in splaying one or more leg portions of the cannula carrier.

The details of one or more implementations of the disclosure are set forth in the accompanying drawings and the description below. Other aspects, features, and advantages will be apparent from the description and drawings, and from the claims.

DESCRIPTION OF DRAWINGS

The drawings described herein are for illustrative purposes only of selected configurations and not all possible implementations, and are not intended to limit the scope of the present disclosure.

FIG. 6 is a side view of the hub of FIG. 2.

FIG. 7 is a cross-sectional view of the hub according to line 7-7 of FIG. 6.

FIG. 8A is another side view of the hub of FIG. 2.

FIG. 8B is a top view of the hub according to arrow 8B of FIG. 8A.

FIG. 9A is another side view of the hub of FIG. 2.

FIG. 9B is a top view of the hub according to arrow 9B of FIG. 9A.

FIG. 13 is a top view of the hypodermic interface sub-assembly according to arrow 13 of FIG. 12.

FIG. 14 is a bottom view of the hypodermic interface sub-assembly according to arrow 14 of FIG. 12.

FIG. 24 is a top view of the cannula carrier according to arrow 24 of any of FIGS. 18-23.

FIG. 25 is a bottom view of the cannula carrier according to arrow 25 of any of FIGS. 18-23.

FIG. 26E is a side view of the cannula carrier of FIG. 26D rotated 45°.

FIG. 26F is a side view of the cannula carrier of FIG. 26E rotated 45°.

FIG. 26G is a side view of the cannula carrier of FIG. 26F rotated 45°.

FIG. 26H is a side view of the cannula carrier of FIG. 26G rotated 45°.

FIG. 27E is a bottom view of the cannula carrier corresponding to FIG. 26E.

FIG. 27F is a bottom view of the cannula carrier corresponding to FIG. 26F.

FIG. 27G is a bottom view of the cannula carrier corresponding to FIG. 26G

FIG. 27H is a bottom view of the cannula carrier corresponding to FIG. 26H.

Corresponding reference numerals indicate corresponding parts throughout the drawings.

DETAILED DESCRIPTION

Figure 1:
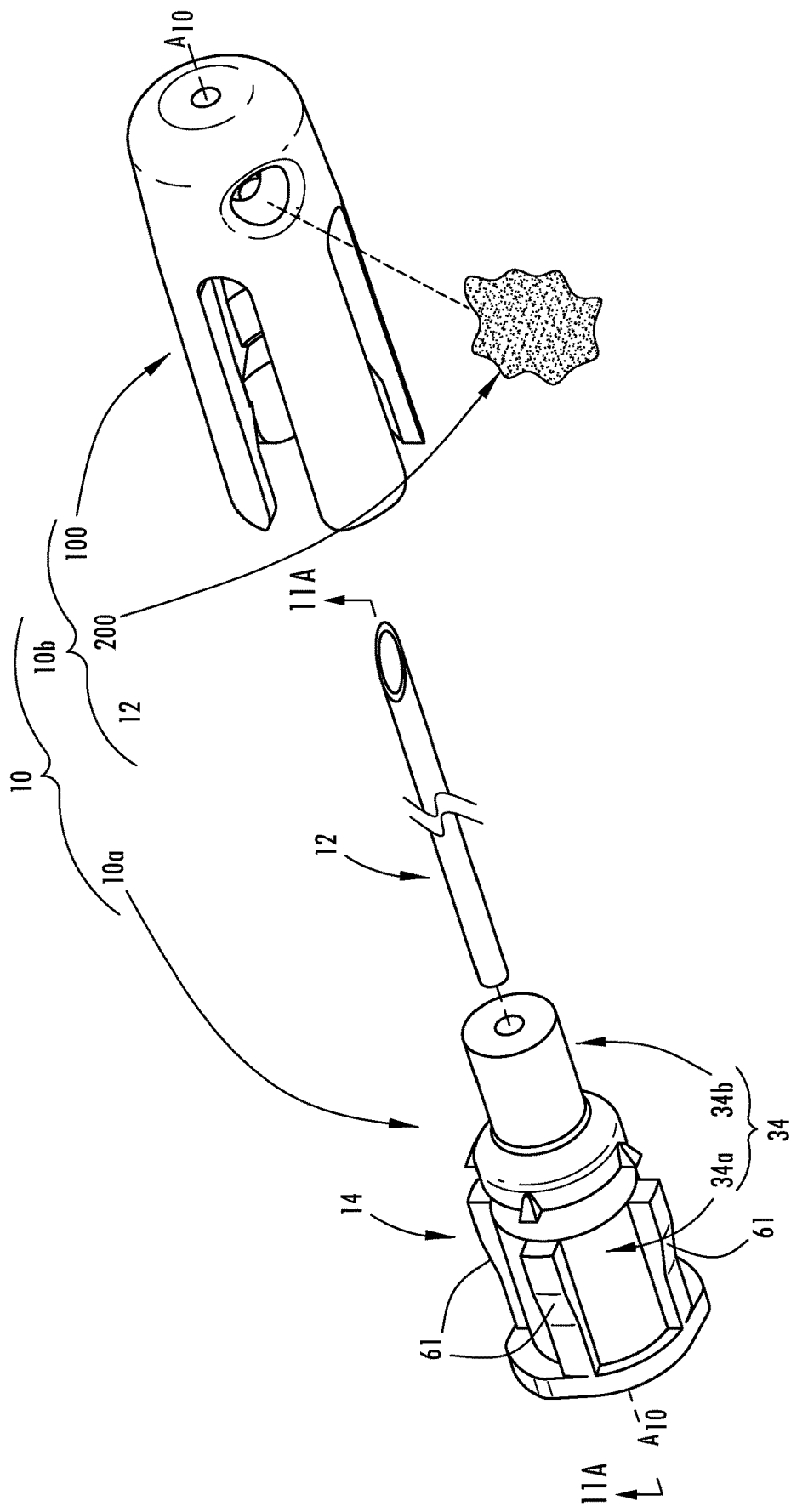
FIG. 1 is an exploded perspective view of an exemplary hypodermic interface assembly.

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

The figures illustrate exemplary implementations of hypodermic interface assemblies. Based on the foregoing, it is to be generally understood that the nomenclature used herein is simply for convenience and the terms used herein should be given the broadest meaning by one of ordinary skill in the art.

Referring to FIGS. 1 and 33-35B, a hypodermic interface assembly including a cannula 12 (see, e.g., FIGS. 1-2), a hub 14 (see, e.g., FIGS. 1 and 3-10), a cannula carrier 100 (see, e.g., FIGS. 18-27H), and an optional adhesive 200 (see, e.g., FIGS. 1 and 31-32) is shown generally at 10. Furthermore, a sub-assembly of the hypodermic interface assembly that is defined by the cannula 12 and the hub 14 is seen at FIGS. 11A-17. A central axis that extends through an axial center of each component (e.g., the cannula 12, the hub 14, and the cannula carrier 100) of the hypodermic interface assembly 10 is shown generally at $A_{10}$-$A_{10}$. As will be described in the following disclosure at FIGS. 31-32, the adhesive 200 is radially deposited through a radial passage (see, e.g., radial passage 122 of the cannula carrier 100) and the adhesive 200 surrounds a portion of the cannula 12 for optionally adhesively connecting the cannula 12 to at least the cannula carrier 100. Accordingly, the central axis $A_{10}$-$A_{10}$ may also extend though an axial center of the adhesive 200 after it surrounds the cannula 12. An exemplary alternative configuration of the hypodermic interface assembly 10 is also seen at, for example, FIGS. 38C and 39A-39C and functions in a similar manner as the hypodermic interface assembly 10.

As seen at FIGS. 40 and 41A-41G, the cannula 12 is configured to pierce an outer surface $S_S$ (e.g., the skin or hide) of a subject S (e.g., animalia, such as a human or non-human). The purpose of piercing the skin or hide $S_S$ of the animalia S may be directed to injecting a fluid F (e.g., a medicament, a pharmaceutical, a vaccine, an anesthetic, or the like) into the animalia S as seen at, for example, FIG. 41C. In other examples, the purpose of piercing the skin or hide $S_S$ of the animalia S may be directed to the purpose of drawing a fluid F (e.g., blood) from the animalia S. Accordingly, the cannula 12 may be referred to as a hypodermic cannula, and, as such, the assembly 10 may be referred to as a hypodermic interface assembly as a result of the cannula 12 being capable of injecting or drawing a fluid F into/from the animalia S.

Figure 39A:
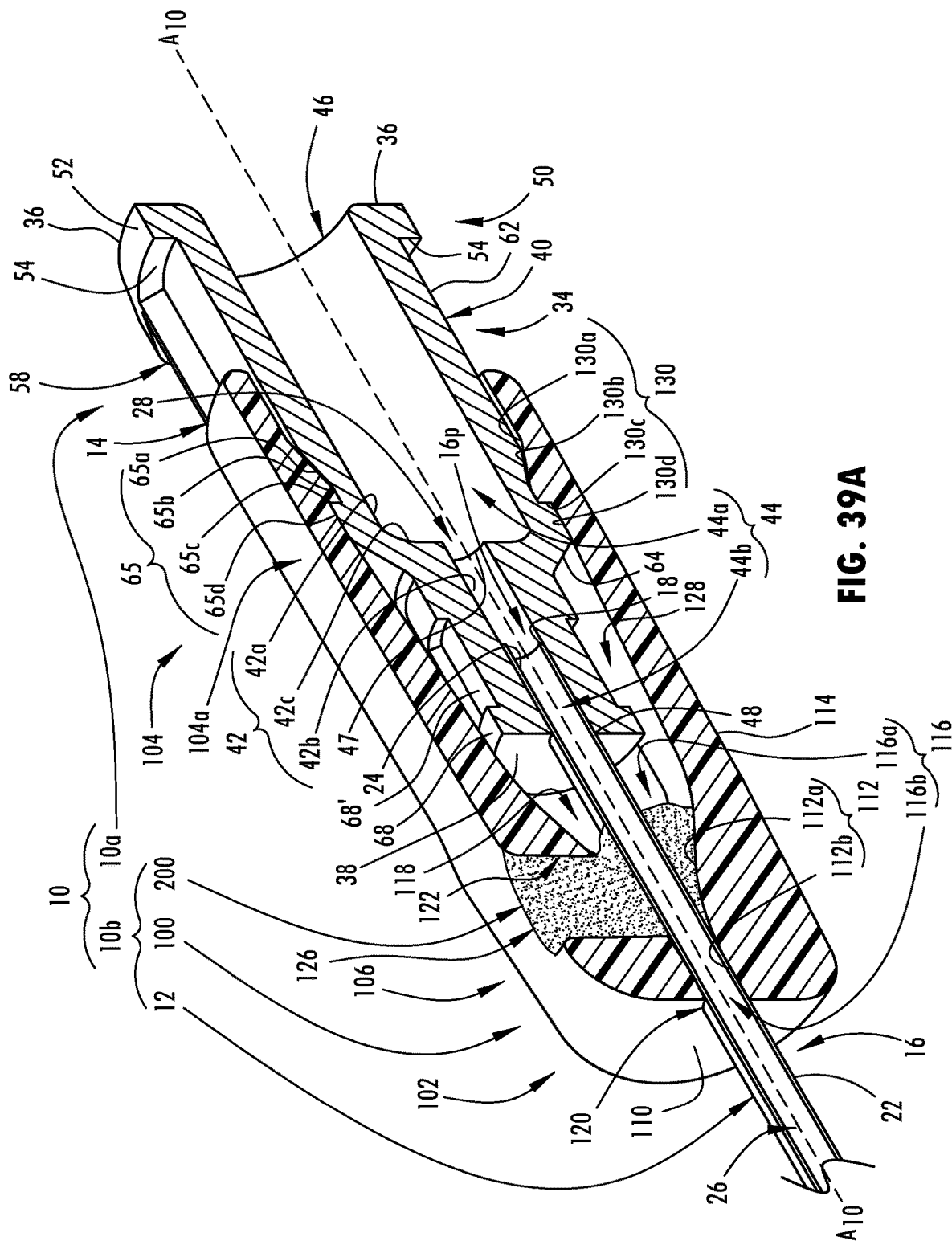
FIG. 39A is perspective cross-sectional view according to the side perspective view of the hypodermic interface assembly of FIG. 38C that is arranged in an at-rest orientation.
Figure 39B:
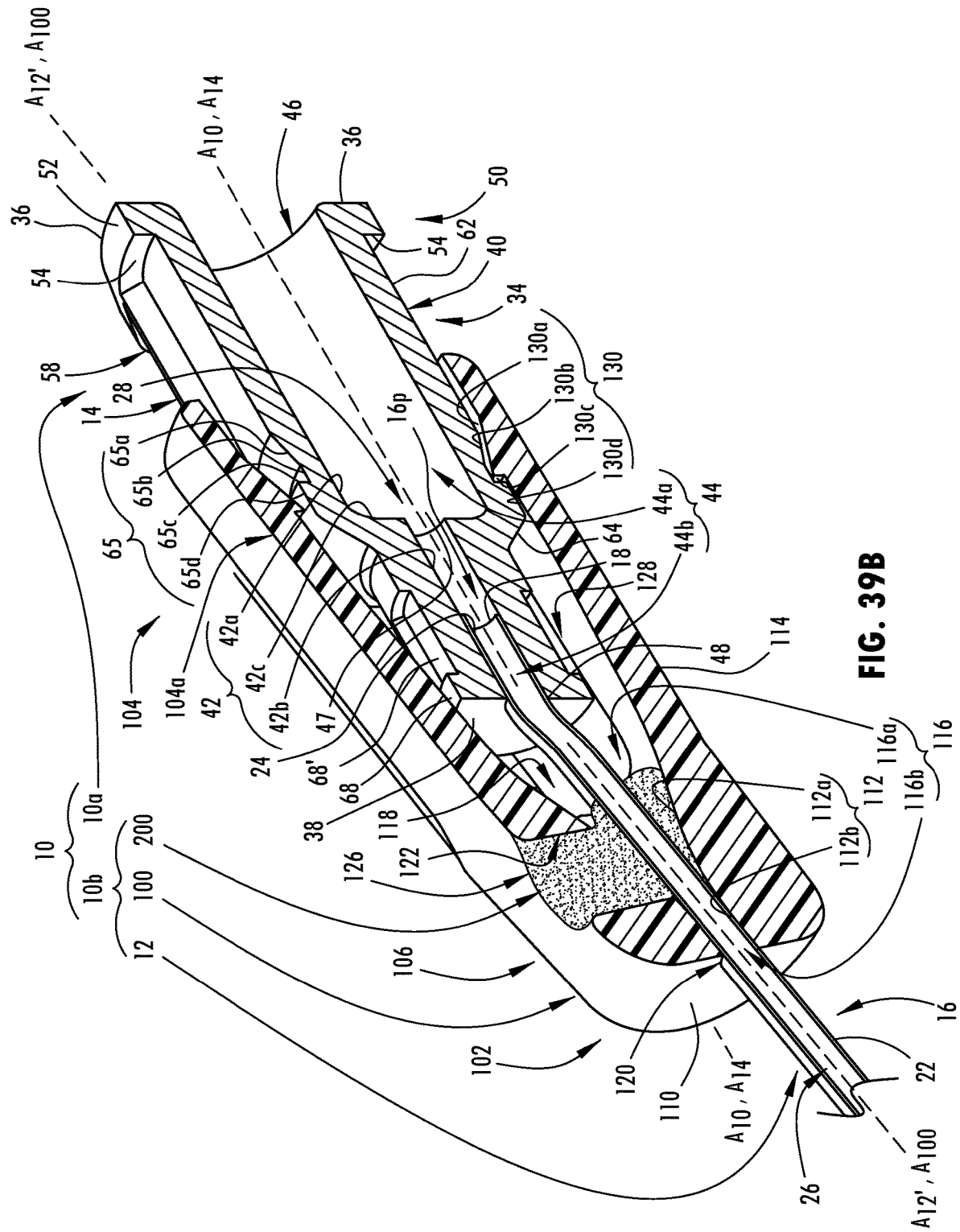
FIG. 39B is another perspective cross-sectional view according to the front perspective view of the hypodermic interface assembly of FIG. 39A that is arranged in a biased orientation.
Figure 39C:
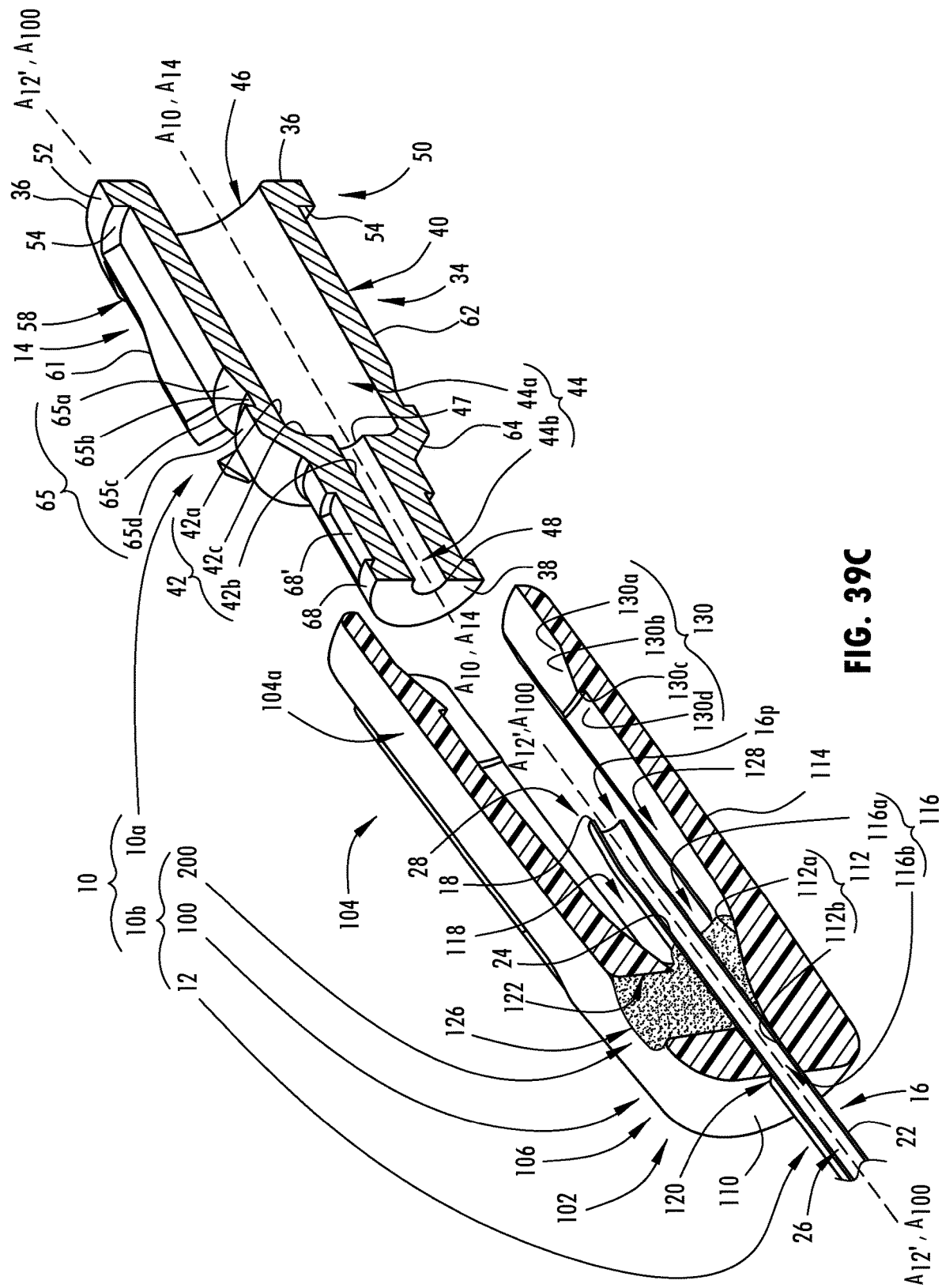
FIG. 39C is another perspective cross-sectional view according to the front perspective view of the hypodermic interface assembly of FIG. 39B that is arranged in a separated orientation.

The design of the hypodermic interface assembly 10 provides for: (1) a first portion (see, e.g., a first portion 10a at FIGS. 37A-37B and 41E-41G) of the hypodermic interface assembly 10 that is configured to remain attached to an injection gun I after the cannula 12 is subjected to one or more radial forces $X_R$ (see, e.g., FIG. 41D) relative to the central axis $A_{10}$-$A_{10}$ extending through the hypodermic interface assembly 10; and (2) a second portion (see, e.g., a second portion 10b at FIGS. 37A-37B and 41E-41G) of the hypodermic interface assembly 10 that is configured to controllably (and/or predictably) separate from the first portion 10a of the hypodermic interface assembly 10 after the cannula 12 is subjected to the one or more radial forces $X_R$ relative to the central axis $A_{10}$-$A_{10}$ extending through the hypodermic interface assembly 10. With reference to FIG. 39C, in some configurations, the second portion 10b of the hypodermic interface assembly 10 includes the entirety of a length (see, e.g., $L_{12}$ in FIG. 2) of the cannula 12. In some instances, controlled separation of the second portion 10b of the hypodermic interface assembly 10 from the first portion 10a of the hypodermic interface assembly 10 may occur after the cannula 12 pierces the subject S (see, e.g., FIGS. 40 and 41B-41D). The subject S may be, for example, animalia, such as a human or non-human (i.e., an animal, such as a pig or swine). In other examples, the subject S may be an inanimate object. The predicable and controlled separation of the second portion 10b of the hypodermic interface assembly 10 from the first portion 10a of the hypodermic interface assembly 10 mitigates separation of the cannula 12 alone from a non-separated, non-broken, or unitary configuration of the hub 14, which may otherwise result in the cannula 12 being broken-off from the injection gun I and subsequently being lost within the flesh of the animalia.

Figure 2:
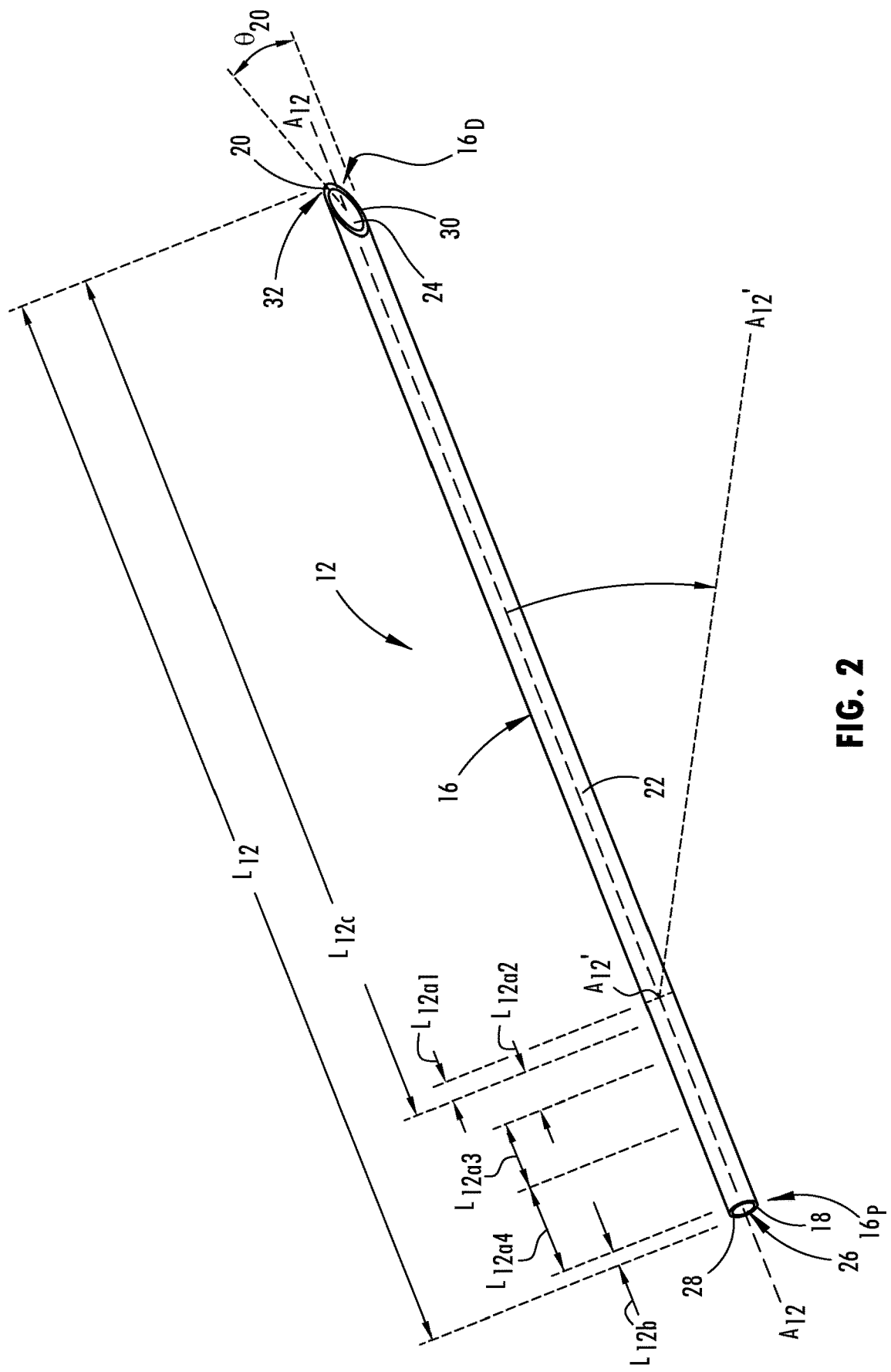
FIG. 2 is a perspective view of an exemplary cannula of the hypodermic interface assembly of FIG. 1.
Figure 3:
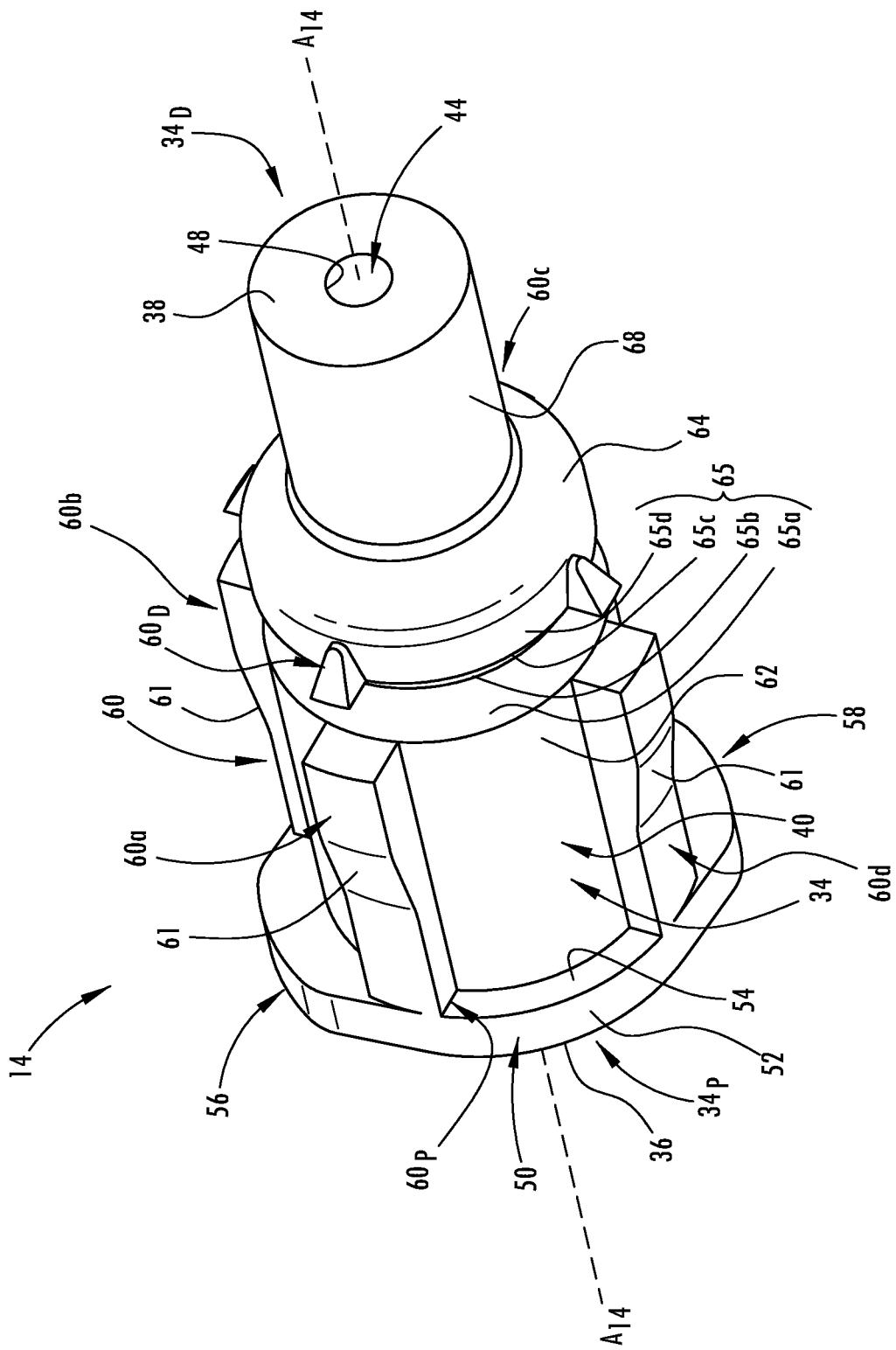
FIG. 3 is a front perspective view of an exemplary hub of the hypodermic interface assembly of FIG. 1.
Figure 4:
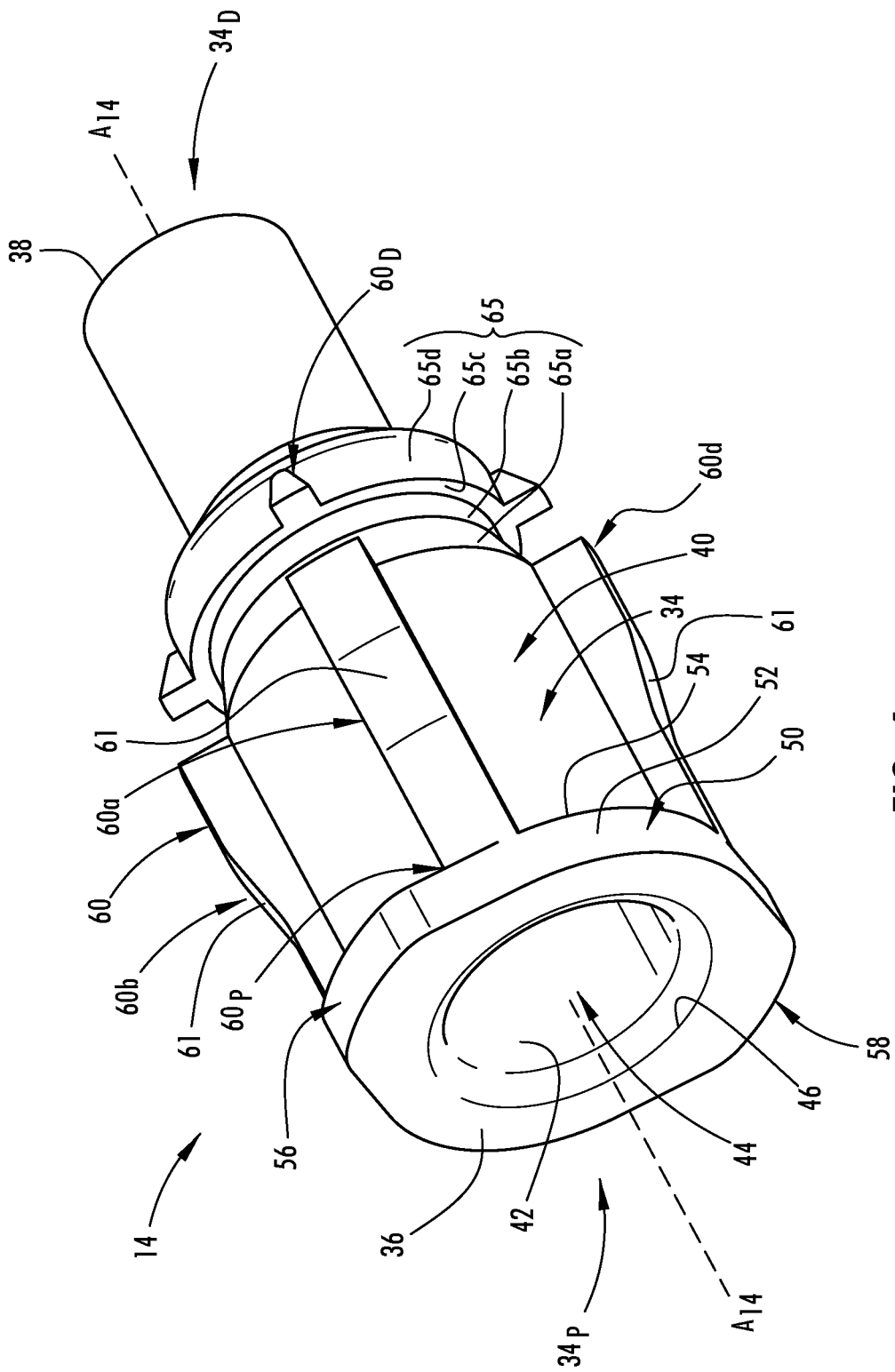
FIG. 4 is a rear perspective view of the hub of FIG. 2.
Figure 5:
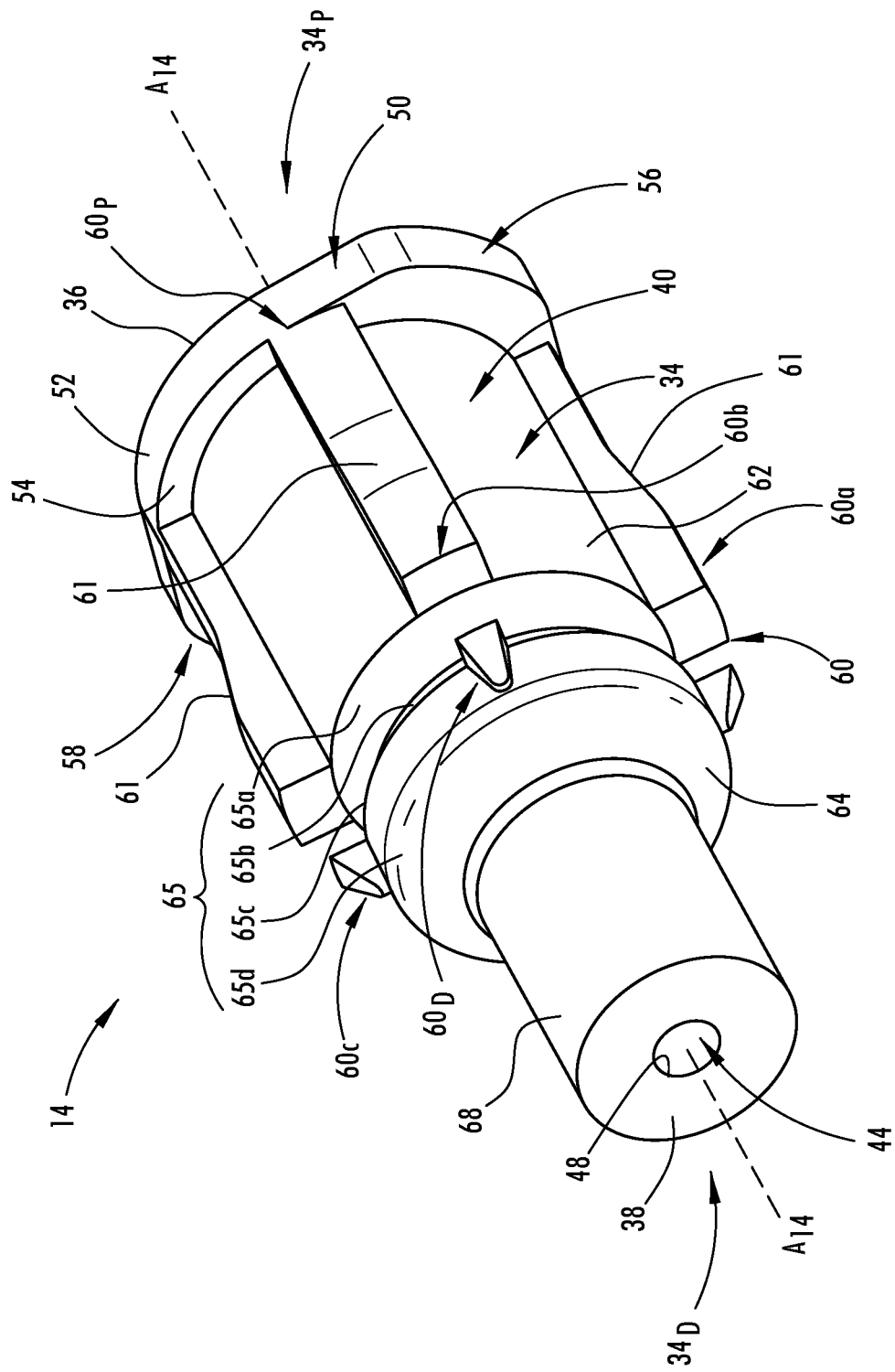
FIG. 5 is another front perspective view of the hub of FIG. 2.
Figure 10:
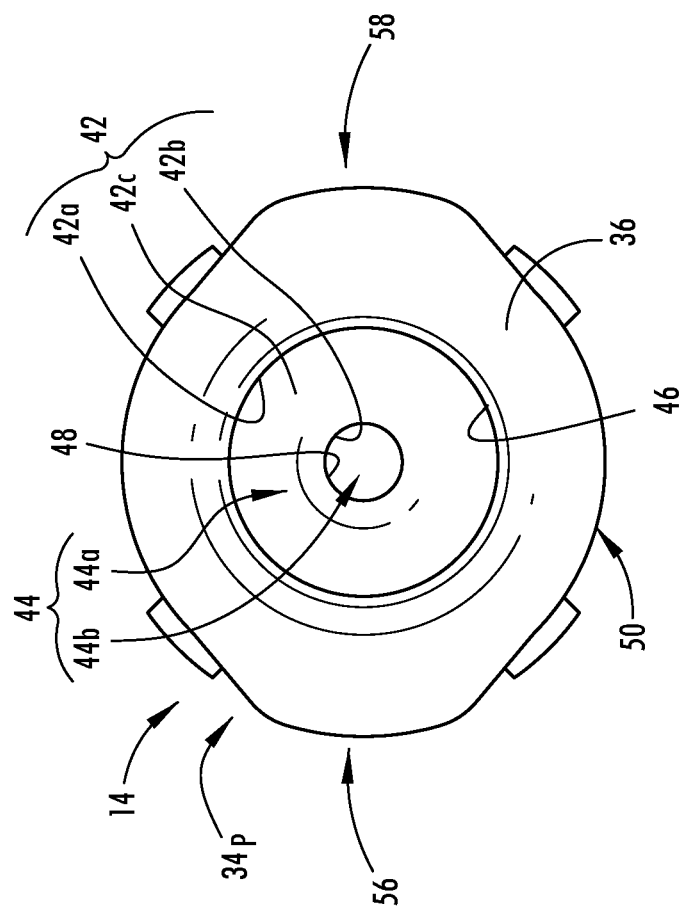
FIG. 10 is a bottom view of the hub according to arrow 10 of FIG. 8A or 9A.

As seen at FIG. 2, the cannula 12 is defined by a tube-shaped body 16 having a proximal end $16_P$ and a distal end $16_D$. The cannula 12 is defined by a length $L_{12}$ extending between the proximal end $16_P$ of the tube-shaped body 16 and the distal end $16_D$ of the tube-shaped body 16. The length $L_{12}$ of the cannula 12 is defined by a plurality of sub-lengths $L_{12a}$ (including sub-length portions $L_{12a1}$, $L_{12a2}$, $L_{12a3}$, and $L_{12a4}$), $L_{12b}$, and $L_{12c}$, which will be further described in the following disclosure.

The cannula 12 may be formed using any desirable manufacturing procedure such as, for example: a drawing procedure, a molding procedure; a casting procedure; a machining procedure; a lathing procedure; or a combination thereof. The cannula 12 made from any desirable material such as, for example: a metallic material; a plastic material; or a combination thereof. In some examples, the cannula 12 may be made from a stainless steel material. In other instances, the cannula 12 may be made from an aluminum material. In yet other examples, the cannula 12 may be made from a detectable material such as, for example, a detectable alloy, a ferromagnetic alloy, a magnetically-detectable material, a magnetic resonance imaging (MRI) detectable material, a material that absorbs X-rays, or the like.

The cannula 12 may be defined in terms of 'gauge size' that takes into consideration skid/hide thickness of the subject S and/or a depth of injection of the subject S. The gauge size of the cannula 12 may be defined in a series of industry standard numbers in which, for example, the lower the number, the wider the diameter of the cannula. Furthermore, the series of industry standard numbers defining gauge size of the cannula 12 may be defined in a manner such that, for example, a higher gauge number indicates a smaller width of the cannula 12. In some instances, the industry standard gauge sizes of the cannula 12 may range from, for example: 14-Gauge; 16-Gauge; 18-Gauge; and 20-Gauge. Accordingly, in the range of exemplary industry standard numbers described above, a 14-Gauge cannula may be said to have a relatively largest diameter and highest strength (in terms of bendability/flexibility to a point where the cannula 12 could potentially break/fail) whereas a 20-Gauge cannula may be said to have a relatively smallest diameter and lowest strength (in terms of bendability/flexibility to a point where the cannula 12 could potentially break/fail).

A central axis $A_{12}$-$A_{12}$ extends through an axial center of the tube-shaped body 16 and along the length $L_{12}$ of the tube-shaped body 16. As will be described in the following disclosure and shown at FIG. 41D and at FIG. 2, a portion of the length $L_{12}$ of the tube-shaped body 16 (see, e.g., the sub-length portion $L_{12c}$) may bend, flex, or deviate from the central axis $A_{12}$-$A_{12}$ that extends through an axial center of the tube-shaped body 16. The sub-length portion $L_{12c}$ of the length $L_{12}$ of the tube-shaped body 16 that may bend, flex, or deviate from the central axis $A_{12}$-$A_{12}$ extends generally along an axis $A_{12}'$-$A_{12}'$ that may be said to be not aligned with and to deviate away from the central axis $A_{10}$-$A_{10}$ extending through the hypodermic interface assembly 10 when the cannula 12 is arranged as a component of the hypodermic interface assembly 10.

The tube-shaped body 16 is further defined by a proximal end surface 18 at the proximal end $16_P$ of the tube-shaped body 16 and a distal end surface 20 at distal end $16_D$ of the tube-shaped body 16. The tube-shaped body 16 is further defined by an outer surface 22 extending between the proximal end surface 18 and the distal end surface 20. The tube-shaped body 16 is further defined by an inner surface 24 extending between the proximal end surface 18 and the distal end surface 20. The inner surface 24 further defines a passage 26 extending through the tube-shaped body 16. The proximal end surface 18 defines a proximal opening 28 that is in fluid communication with the passage 26. The distal end surface 20 defines a distal opening 30 that is in fluid communication with the passage 26.

Figure 38A:
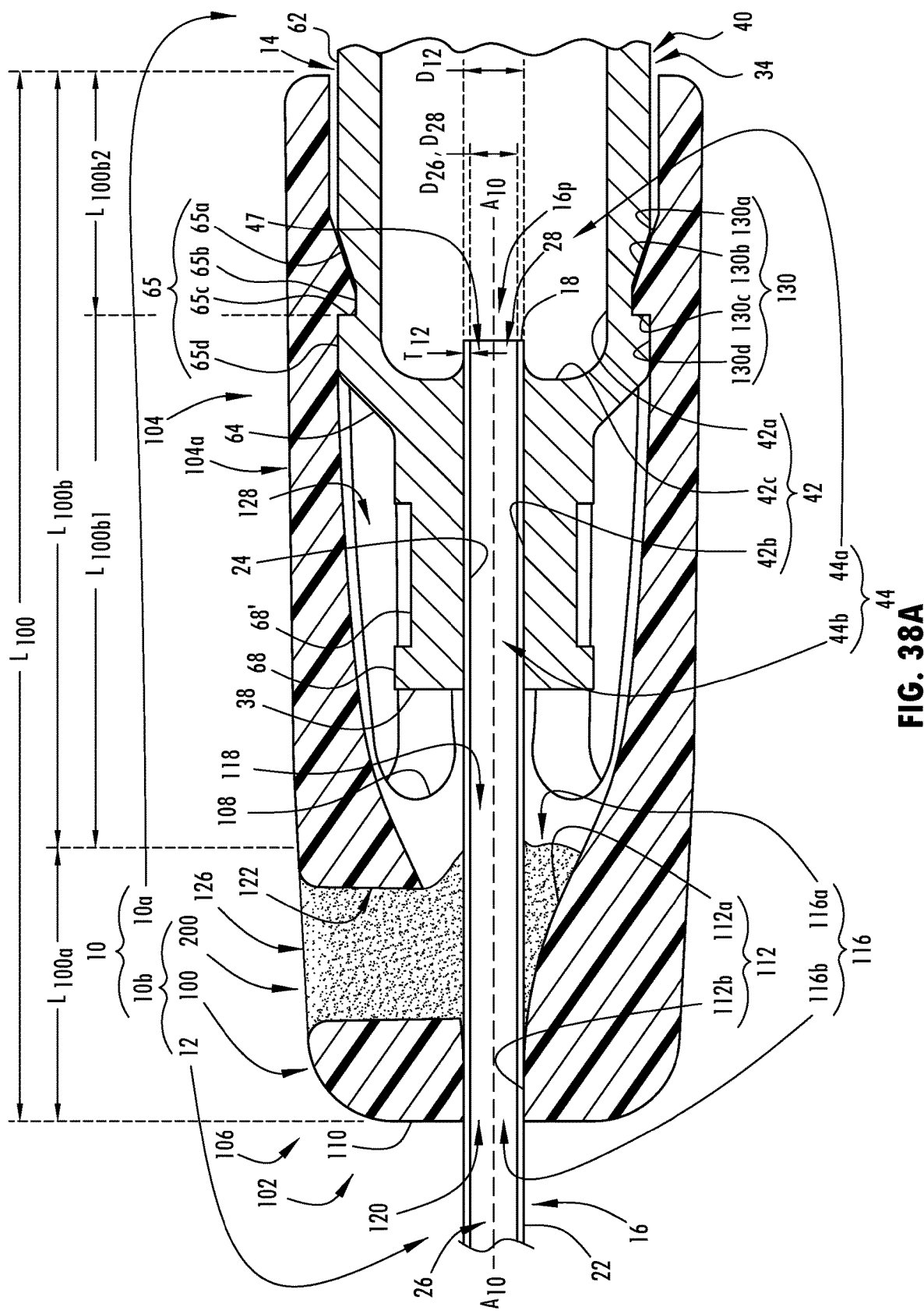
FIG. 38A is an enlarged view of the assembled hypodermic interface assembly according to line 38A of FIG. 35B.

With reference to FIG. 38A (which illustrates an enlarged cross-section view of an exemplary hypodermic interface assembly 10), the body 16 of the cannula 12 is defined by a thickness $T_{12}$ extending between the outer surface 22 of the body 16 and the inner surface 24 of the body 16. The outer surface 22 further defines an outer diameter $D_{12}$ of the cannula 12 that is referenced from the central axis $A_{12}$-$A_{12}$, which may be coincident with respective central axes $A_{10}$-$A_{10}$ and $A_{14}$-$A_{14}$ of each of the hypodermic interface assembly 10 and the hub 14. The inner surface 24 further defines the passage 26 to have a passage diameter $D_{26}$. The passage 26 is in fluid communication with the proximal opening 28 and the distal opening 30 in order to permit: (1) passage of a fluid F (see, e.g., FIG. 41C) into the tube-shaped body 16 at the proximal opening 28; (2) through the passage 26 in a direction from the proximal end $16_P$ of the tube-shaped body 16 and towards the distal end $16_D$ of the tube-shaped body 16; and (3) out of the distal opening 30.

With reference to FIGS. 2 and 38A, the proximal end surface 18 extends from the outer surface 22 substantially perpendicularly, and, as such, defines the proximal end surface 18 to be blunted or non-sharpened. Furthermore, the proximal opening 28 formed by the proximal end surface 18 may define a substantially circular-shaped geometry that is defined by a proximal opening diameter $D_{28}$ that is substantially similar to the passage diameter $D_{26}$ of the passage 26.

With reference to FIG. 2, the distal end surface 20 extends from the outer surface 22 at a beveled angle $\theta_{20}$, and, as such, the distal end surface 20 may be referred to as a beveled distal end surface that terminates at or defines a sharp piercing tip 32. The beveled distal end surface 20 may be defined by any desirable beveled angle $\theta_{20}$ that forms, for example, a "standard bevel," a "short bevel," or a "true short bevel." Because the beveled distal end surface 20 extends from the outer surface 22 at a beveled angle $\theta_{20}$, the distal opening 30 may be defined by an oval-shaped geometry. In one embodiment, the distal end surface 20 may be defined by three separate beveled cuts.

As seen at FIGS. 3-10, the hub 14 is defined by a substantially tube-shaped body 34 having a proximal end $34_P$ and a distal end $34_D$. The hub 14 is defined by a length $L_{14}$ (see, e.g., FIG. 7) extending between the proximal end $34_P$ of the substantially tube-shaped body 34 and the distal end $34_D$ of the substantially tube-shaped body 34. The length $L_{14}$ of the hub 14 is defined by a plurality of sub-lengths $L_{14a}$, $L_{14b}$, $L_{14c}$, and $L_{14d}$, which will be further described in the following disclosure.

The hub 14 may be formed using any desirable manufacturing procedure such as, for example: a molding procedure; a casting procedure; a machining procedure; a lathing procedure; or a combination thereof. The hub 14 made from any desirable material such as, for example: a metallic material; a plastic material; or a combination thereof. In some examples, the hub 14 may be made from a stainless steel material. In other instances, the hub 14 may be made from an aluminum material, brass, steel, or alloys. In other examples, the hub 14 may be made from plastic materials including but not limited to polypropylene (PP), polyethylene terephthalate (PET), polyamides (e.g., nylon 6, nylon 6, 6, thermosetting plastics such as polyester resins, epoxy resins, acrylics), and the like. Furthermore, in some instances, the hub 14 may be finished with an anodization, a polishing, an electro-polishing, a coating, a paint or the like with, for example, a highly visible finish (e.g., a dye, a fluorescent coating, a phosphorescent coating, a bright gloss, matt color finish, or the like that preferably is not similar to the flesh tone or color of the surface $S_S$ of the flesh of the animalia).

The substantially tube-shaped body 34 is further defined by a proximal end surface 36 at the proximal end $34_P$ of the substantially tube-shaped body 34 and a distal end surface 38 at distal end $34_D$ of the substantially tube-shaped body 34. The substantially tube-shaped body 34 is further defined by an outer surface 40 extending between the proximal end surface 36 and the distal end surface 38. The substantially tube-shaped body 34 is further defined by an inner surface 42 extending between the proximal end surface 36 and the distal end surface 38.

The inner surface 42 further defines a passage 44 extending through the substantially tube-shaped body 34. The proximal end surface 36 defines a proximal opening 46 (see, e.g., FIGS. 4, 7, and 10) that is in fluid communication with the passage 44. The distal end surface 38 defines a distal opening 48 (see, e.g., FIGS. 3, 5, 7, 8B, 9B) that is in fluid communication with the passage 44.

As seen at FIGS. 3-10, a ring portion 50 projects radially outwardly away from a central axis $A_{14}$-$A_{14}$ away from the outer surface 40 of the substantially tube-shaped body 34. The ring portion 50 may be alternatively referred to as a barrel-engaging portion that is configured to be connected to a barrel portion $I_B$ of an injection gun I (see, e.g., FIG. 40). The barrel-engaging portion 50 is defined by an outer side surface 52 that extends between the proximal end surface 36 and a distal shoulder surface 54. The barrel-engaging portion 50 may be defined by a thickness $T_{50}$ (see, e.g., FIGS. 6 and 7) extending between the proximal end surface 36 and the distal shoulder surface 54. The barrel-engaging portion 50 may generally define a Luer lock.

The outer surface 40 of the substantially tube-shaped body 34 may define a substantially circular-shaped geometry that defines a first outer diameter $D_{14-1}$ (see, e.g., FIG. 7) of the hub 14. The outer side surface 52 of the barrel-engaging portion 50 may define a substantially circular-shaped geometry that defines a second outer diameter $D_{14-2}$ (see, e.g., FIG. 7) of the hub 14. The second outer diameter $D_{14-2}$ of the hub 14 is greater than the first outer diameter $D_{14-1}$ of the hub 14. The outer surface 40 of the substantially tube-shaped body 34 may further define another substantially circular-shaped geometry that further defines a third outer diameter $D_{14-3}$ (see, e.g., FIG. 7) of the hub 14.

As seen at FIGS. 3-5, 8A-8B, 9A-9B, and 10, the substantially circular-shaped geometry of the outer side surface 52 of the barrel-engaging portion 50 is interrupted by a first radially-outward projection or ear 56 and a second radially-outward projection or ear 58 that extend beyond the second outer diameter $D_{14-2}$ of the hub 14. The first radially-outward projection or ear 56 may be arranged opposite of or offset approximately 180° from the second radially-outward projection or ear 58.

As seen at FIG. 7, the inner surface 42 of the substantially tube-shaped body 34 includes a first inner surface portion 42a, a second inner surface portion 42b, and a third inner surface portion 42c. Each of the first inner surface portion 42a and the second inner surface portion 42b generally circumscribe the central axis $A_{14}$-$A_{14}$ of the hub 14. The third inner surface portion 42c connects the first inner surface portion 42a to the second inner surface portion 42b; furthermore, the third inner surface portion 42c may be substantially orthogonal to the central axis $A_{14}$-$A_{14}$ of the hub 14. The third inner surface portion 42c may be substantially perpendicular with respect to each of the first inner surface portion 42a and the second inner surface portion 42b; in some implementations, the transition of each of the first inner surface portion 42a and the second inner surface portion 42b to the third inner surface portion 42c may be defines by a curved or arcuate segment. As will be seen in the following disclosure at FIGS. 11B-11C, after material deformation of at least a portion of, for example, the second portion 34b of the substantially tube-shaped body 34 of the hub 14 (e.g., by crimping a portion of, for example, the second portion 34b of the substantially tube-shaped body 34 of the hub 14 after the cannula 12 is interfaced with the hub 14 as seen as FIG. 11B), the curved or arcuate segment joining the second inner surface portion 42b to the third inner surface portion 42c may change in shape as a result of the material shifting or "flowing", and, as such, a portion of the third inner surface portion 42c that extends from the second inner surface portion 42b may define a frustoconical surface portion (see, e.g., FIG. 11C) surrounding the cannula 12.

The first inner surface portion 42a of the inner surface defines a first passage portion 44a of the passage 44. The second inner surface portion 42b defines a second passage portion 44b of the passage 44.

The first passage portion 44a defines a first passage diameter $D_{44-1}$ (see, e.g., FIG. 7) of the passage 44. The second passage portion 44b defines a second passage diameter $D_{44-2}$ (see, e.g., FIG. 7) of the passage 44. The first passage diameter $D_{44-1}$ is greater than the second passage diameter $D_{44-2}$. The second passage diameter $D_{44-2}$ is approximately equal to but slightly greater than the outer diameter $D_{12}$ of the cannula 12.

The first passage portion 44a of the passage 44 is in fluid communication with the proximal opening 46, and the second passage portion 44b of the passage 44 is in fluid communication with the distal opening 48. Furthermore, the first passage portion 44a is in fluid communication with the second passage portion 44b by way of an intermediate opening 47. Accordingly, the passage 44 permits: (1) passage of a fluid F (see, e.g., FIG. 41C) into the substantially tube-shaped body 34 at the proximal opening 46; (2) through the first passage portion 44a of the passage 44 in a direction from the proximal end $34_P$ of the substantially tube-shaped body 34 and towards the intermediate opening 47 defined by the third inner surface portion 42c; (3) through the intermediate opening 47 that defines a proximal opening of the second passage portion 44b of the passage 44; (4) through the second passage portion 44b of the passage 44 in a direction from the intermediate opening 47 and towards the distal end $34_D$ of the substantially tube-shaped body 34; and (5) out of the distal opening 48.

The proximal opening 46 formed by the proximal end surface 36 may define a substantially circular-shaped geometry that is defined by a proximal opening diameter $D_{46}$ (see, e.g., FIG. 7) that is substantially similar to the first passage diameter $D_{44-1}$ of the first passage portion 44a. The intermediate opening 47 formed by the third inner surface portion 42c of the inner surface 42 of the substantially tube-shaped body 34 may define a substantially circular-shaped geometry that is defined by an intermediate opening diameter $D_{47}$ (see, e.g., FIG. 7) that is substantially equal to the second passage diameter $D_{44-2}$. The distal opening 48 formed by the distal end surface 38 may define a substantially circular-shaped geometry that is defined by a distal opening diameter $D_{48}$ (see, e.g., FIG. 7) that is substantially similar to the second passage diameter $D_{44-2}$. Although some of the dimensions/diameters/geometries are descried above to be substantially similar or the same, the view of the hub 14 in the Figures (e.g., at FIG. 7) are exemplary and are not to scale. In some instances, the first passage portion 44a may be formed to include a draft angle (e.g., a 1° draft angle) that, for example, may assist in the removal of the hub 14 from tooling when the hub 14 is formed. Accordingly, the first passage diameter $D_{44-1}$ of the first passage portion 44a may progressively decrease in diameter as the first passage diameter $D_{44-1}$ of the first passage portion 44a extends in a direction from the proximal end surface 36 of the hub 14 toward the distal end surface 38 of the hub 14.

Referring to FIGS. 3-6, 8A, 8B, 9A, and 9B, one or more ribs 60 may project radially outwardly away from a central axis $A_{14}$-$A_{14}$ away from an outer body surface portion 62 defined by the outer surface 40 of the substantially tube-shaped body 34. The one or more ribs 60 may include, for example, a first rib 60a, a second rib 60b, a third rib 60c, and a fourth rib 60d.

The one or more ribs 60 may increase the structural integrity of the substantially tube-shaped body 34 of the hub 14. In some configurations, the one or more ribs 60 may arise from mold relief features during the manufacturing process of the substantially tube-shaped body 34 of the hub 14. Furthermore, the one or more ribs 60 may be configured to engage packaging (not shown). Engagement of the one or more ribs 60 with the packaging may assist in containing the cannula 12 and the hub 14 during shipping and/or assist in engagement/disengagement of the hub 14 with/from the injection gun I. As seen throughout the Figures, an outer surface portion of each rib 60a, 60b, 60c, 60d may extend radially outwardly, defining a lug portion; the lug portion may, for example be defined by an inclined or beveled surface 61. Each lug portion may be sized for engagement with the packaging.

Each rib 60a, 60b, 60c, 60d of the one or more ribs 60 includes a distal end $60_D$ and a proximal end $60_P$. The proximal end $60_P$ of each rib 60a, 60b, 60c, 60d of the one or more ribs 60 extends from the distal shoulder surface 54 of the barrel-engaging portion 50. The distal end $60_D$ of each rib 60a, 60b, 60c, 60d of the one or more ribs 60 extends in a direction toward the distal end surface 38 of the substantially tube-shaped body 34 and terminates at, before, or near an outer shoulder surface portion 64 (see, e.g., FIGS. 3-9) defined by the outer surface 40 of the substantially tube-shaped body 34. Each rib 60a, 60b, 60c, 60d of the one or more ribs 60 may define a substantially rectangular body that terminates with a substantially triangular body portion defined by the distal end $60_D$ of each rib 60a, 60b, 60c, 60d of the one or more ribs 60.

The outer shoulder surface portion 64 extends from a distal-most end of the outer body surface portion 62 of the outer surface 40 of the substantially tube-shaped body 34. In some configurations, the outer shoulder surface portion 64 may define a dome-shaped or curved outer shoulder surface portion.

Referring to FIGS. 3-7, 8A, and 9A a distal-most end of the outer shoulder surface portion 64 terminates at an outer head surface portion 68. The outer head surface portion 68 generally circumscribes the central axis $A_{14}$-$A_{14}$ of the hub 14.

As seen at FIG. 7, the outer head surface portion 68 of the outer surface 40 of the substantially tube-shaped body 34 defines the third outer diameter $D_{14-3}$ of the hub 14. As seen at FIG. 7, the second outer diameter $D_{14-2}$ is greater than the third outer diameter $D_{14-3}$.

Figure 28:
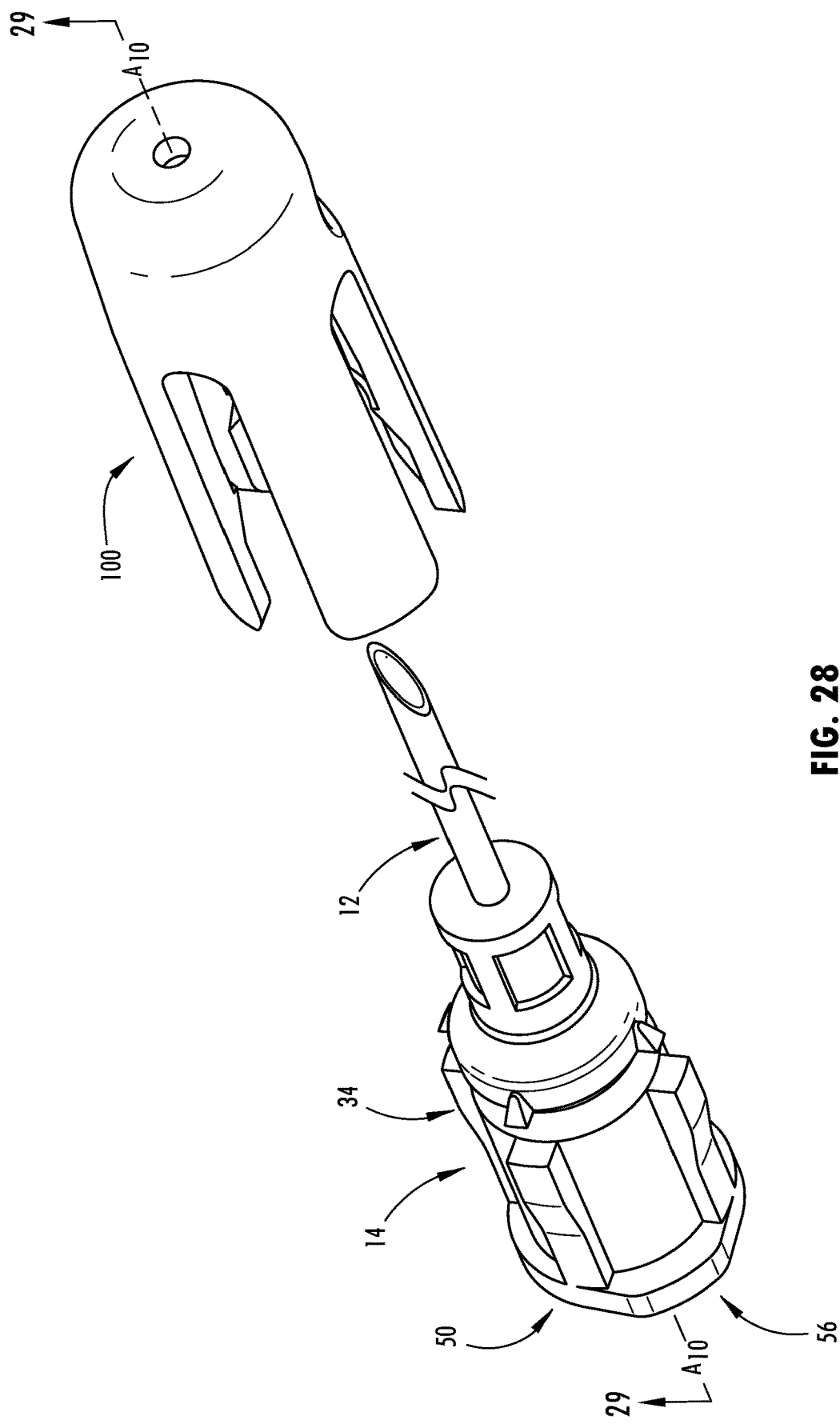
FIG. 28 is an exploded front perspective view of portions of the hypodermic interface assembly of FIG. 1 including the cannula of FIG. 2, the hub of FIGS. 3-10, and the cannula carrier of FIGS. 18-27H.
Figure 29:
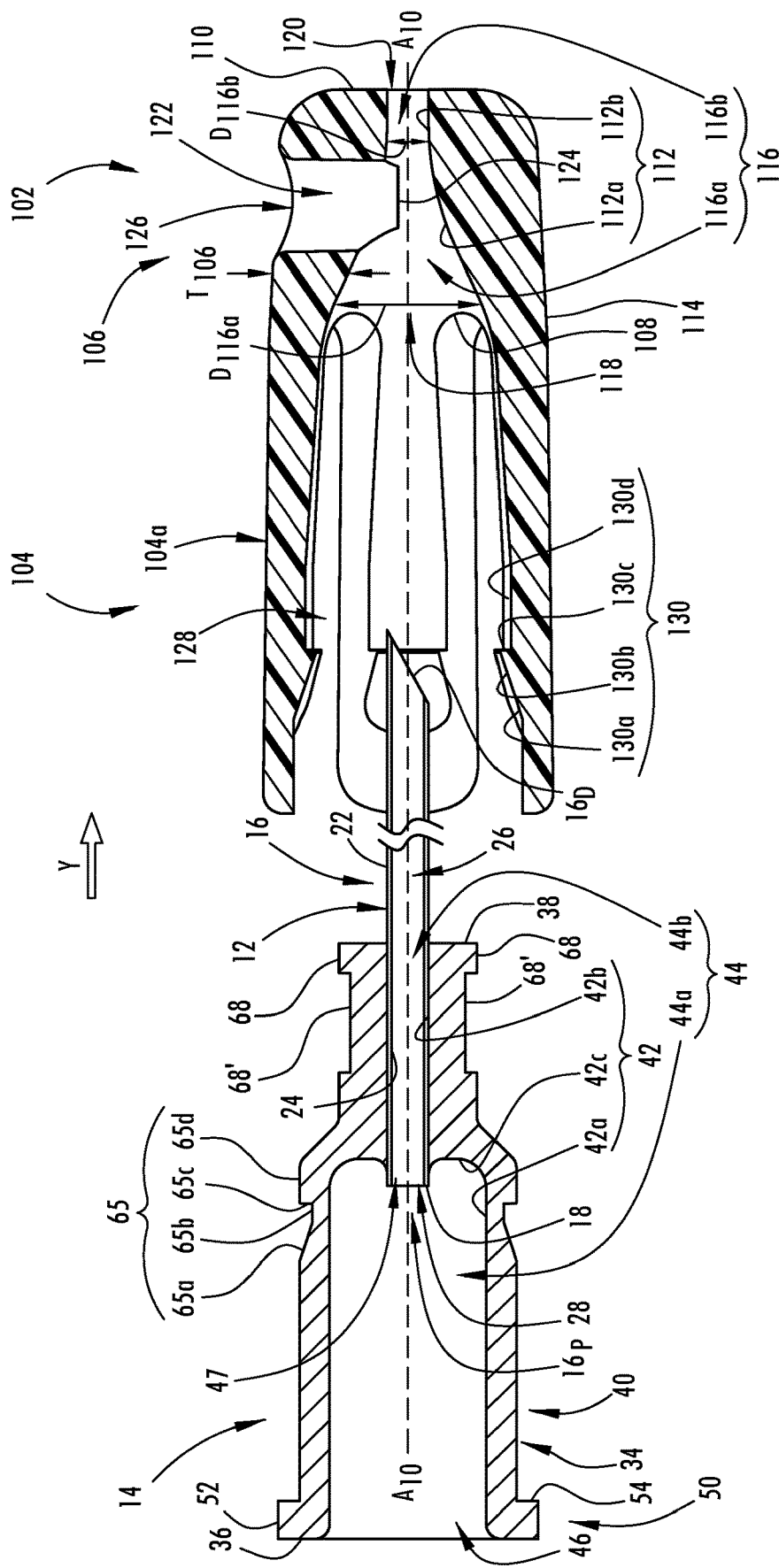
FIG. 29 is a cross-sectional view according to line 29-29 of FIG. 28.
Figure 30:
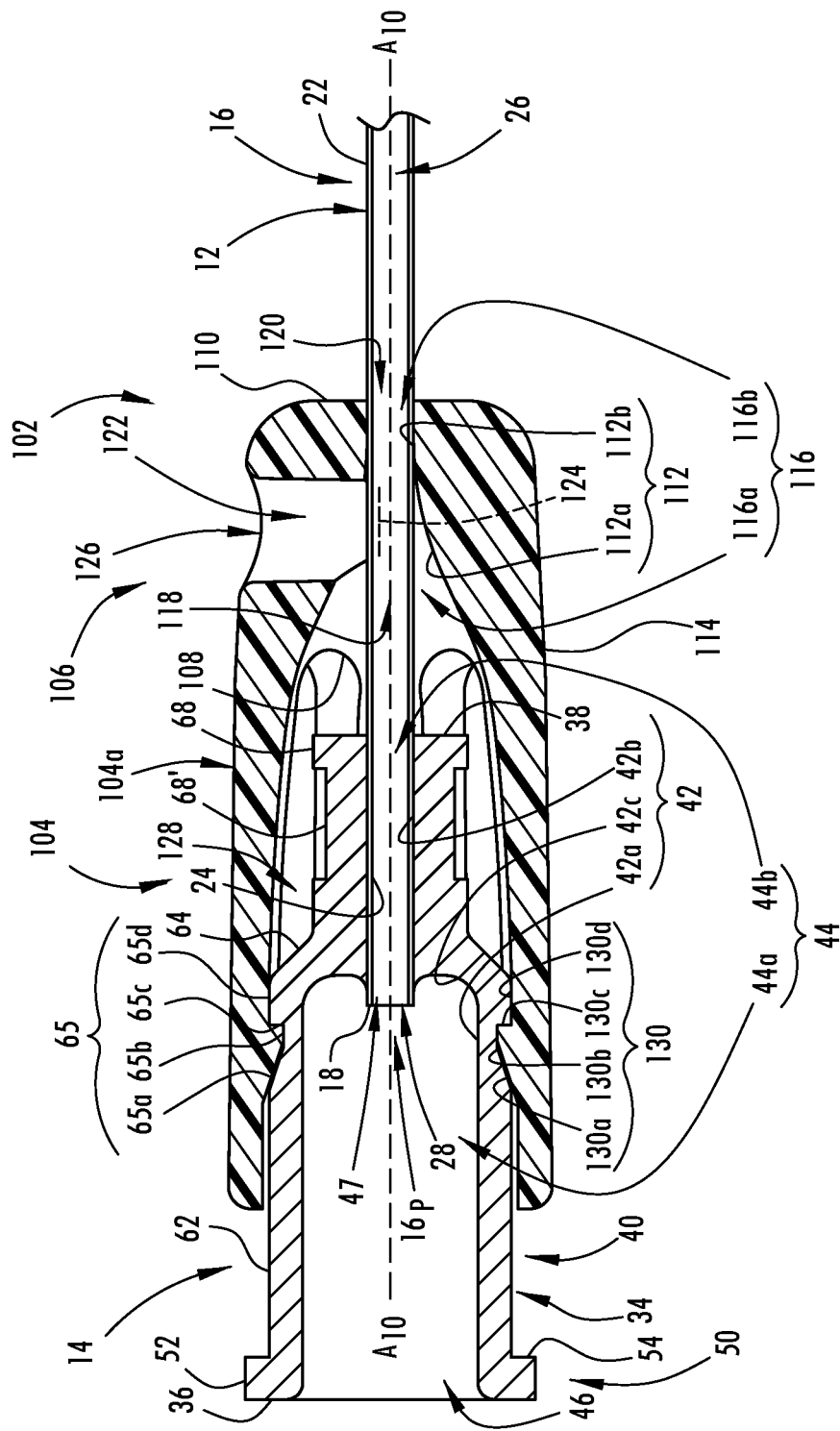
FIG. 30 is another cross-sectional view according to FIG. 29 illustrating the cannula carrier disposed about the hypodermic interface sub-assembly of FIGS. 11C-17.

With reference to FIGS. 6-7, the hypodermic interface assembly 10 also includes a circumferential notch or groove 65 that is configured to receive one or more portions of the cannula carrier 100 (see, e.g., FIGS. 28-30). The circumferential notch or groove 65 may extend into the outer body surface portion 62 of the outer surface 40 of the substantially tube-shaped body 34 of the hub 14 at a distance (see, e.g., the sub-length $L_{14a}$) away from the distal end surface 38 of the hub 14. In some configurations, the circumferential notch or groove 65 may extend into the outer surface 40 of the substantially tube-shaped body 34 near a proximal-most end of the outer shoulder surface portion 64. The circumferential notch or groove 65 may be defined by a plurality of surface portions (see, e.g., surface portions 65a, 65b, 65c, 65d at FIG. 29) of the outer surface 40 of the substantially tube-shaped body 34. The surface portions 65a, 65b, 65c, 65d that define the circumferential notch or groove 65 may be shaped to matingly-receive one or more corresponding surface portions (see, e.g., barb surface portions 130a, 130b, 130c, 130d) of the cannula carrier 100.

With reference to FIG. 7, the sub-length $L_{14a}$ defines the length of the outer shoulder surface portion 64 and the outer head surface portion 68 of the outer surface 40 of the substantially tube-shaped body 34. The sub-length $L_{14b}$ defines the length circumferential notch or groove 65 that is defined by the outer body surface portion 62 of the outer surface 40 of the substantially tube-shaped body 34. The sub-length $L_{14c}$ defines the length of the outer body surface portion 62 of the outer surface 40 of the substantially tube-shaped body 34 that extends between a proximal-most end of the circumferential notch or groove 65 and the distal shoulder surface 54 of the barrel-engaging portion 50. The sub-length $L_{14d}$ defines a thickness of the barrel-engaging portion 50 that extends between the proximal end surface 36 of the substantially tube-shaped body 34 and the distal shoulder surface 54 of the barrel-engaging portion 50.

As will be described in the following disclosure, the substantially tube-shaped body 34 of the hub 14 may define first portion 10a of the hypodermic interface assembly 10 that is configured to remain attached to the injection gun I after the cannula 12 is subjected to one or more radial forces $X_R$ relative to the central axis $A_{10}$-$A_{10}$ extending through the hypodermic interface assembly 10. The cannula carrier 100, which is removably-connected to the hub 14 at, for example, the circumferential notch or groove 65 defined by the outer body surface portion 62 of the outer surface 40 of the substantially tube-shaped body 34 of the hub 14, may define a first component portion of a second portion 10b of the hypodermic interface assembly 10 (with a second component portion of the second portion 10b of the hypodermic interface assembly 10 being the cannula 12 and a third component being the optional adhesive 200) that is configured to controllably separate from the first portion 10a of the hypodermic interface assembly 10 after the cannula 12 is subjected to the one or more radial forces $X_R$ relative to the central axis $A_{10}$-$A_{10}$ extending through the hypodermic interface assembly 10. Accordingly, as will be explained in the following disclosure, upon predictably separating the cannula carrier 100 and the cannula 12 from the substantially tube-shaped body 34 of the hub 14, a user may easily locate and grasp (see, e.g., FIG. 41F) the cannula carrier 100 (that is non-removably-connected to the cannula 12) in order to remove the cannula 12 (see, e.g., FIG. 41G) from the flesh of the animalia S such that the cannula 12 is not lost within the flesh of the animalia S (should the one or more radial forces $X_R$ relative to the central axis $A_{10}$-$A_{10}$ extending through the hypodermic interface assembly 10 be imparted to the cannula 12 during the course of utilizing the hypodermic interface assembly 10, which may otherwise undesirably result in the cannula 12 being separated from the injection gun I).

Figure 11A:
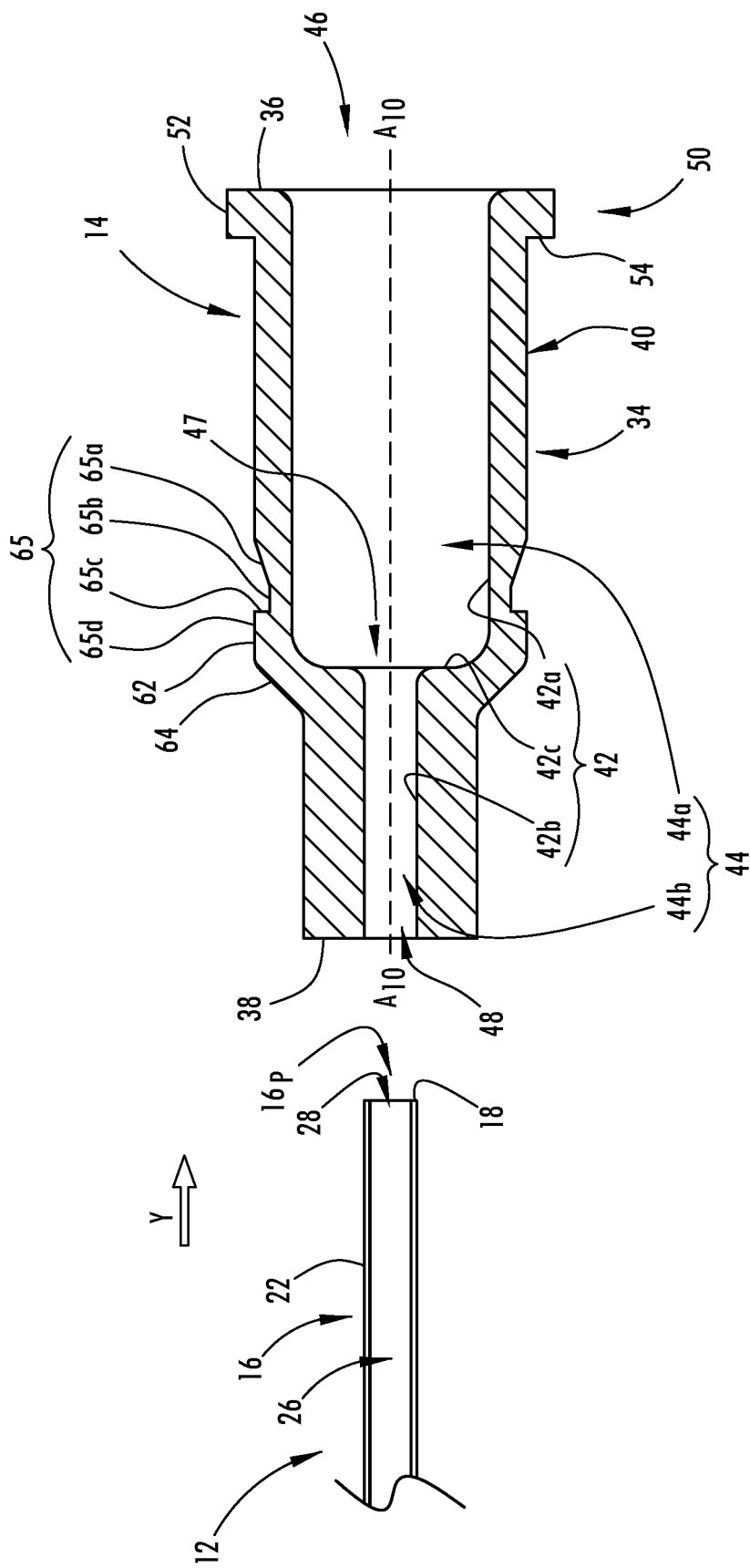
FIG. 11A is a cross-sectional view of a sub-assembly of the hypodermic interface assembly arranged in a first partially assembled state according to line 11A-11A of FIG. 1.
Figure 11B:
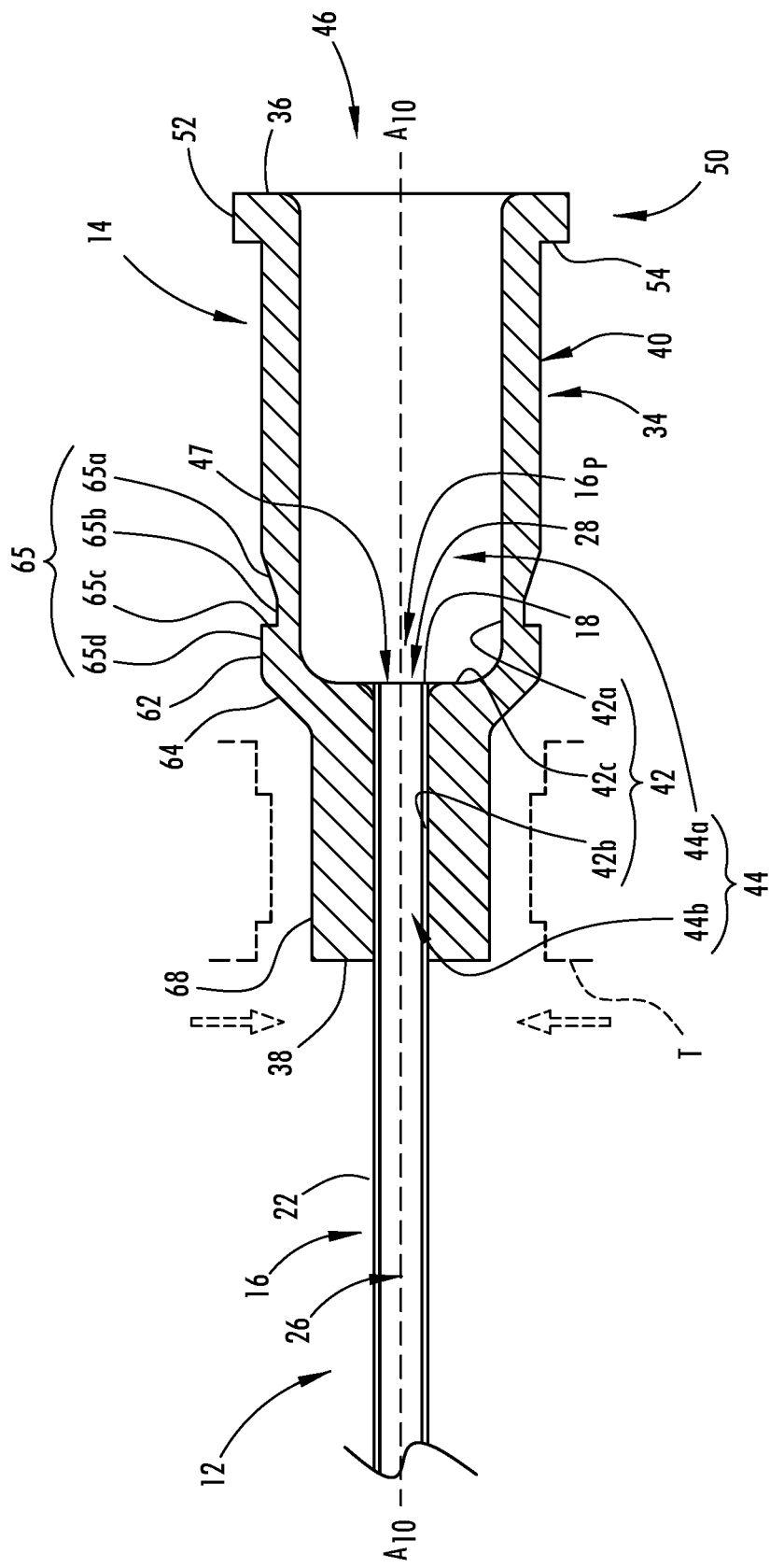
FIG. 11B is a cross-sectional view of a partially assembled hypodermic interface sub-assembly of FIG. 11A arranged in a second partially assembled state.
Figure 11C:
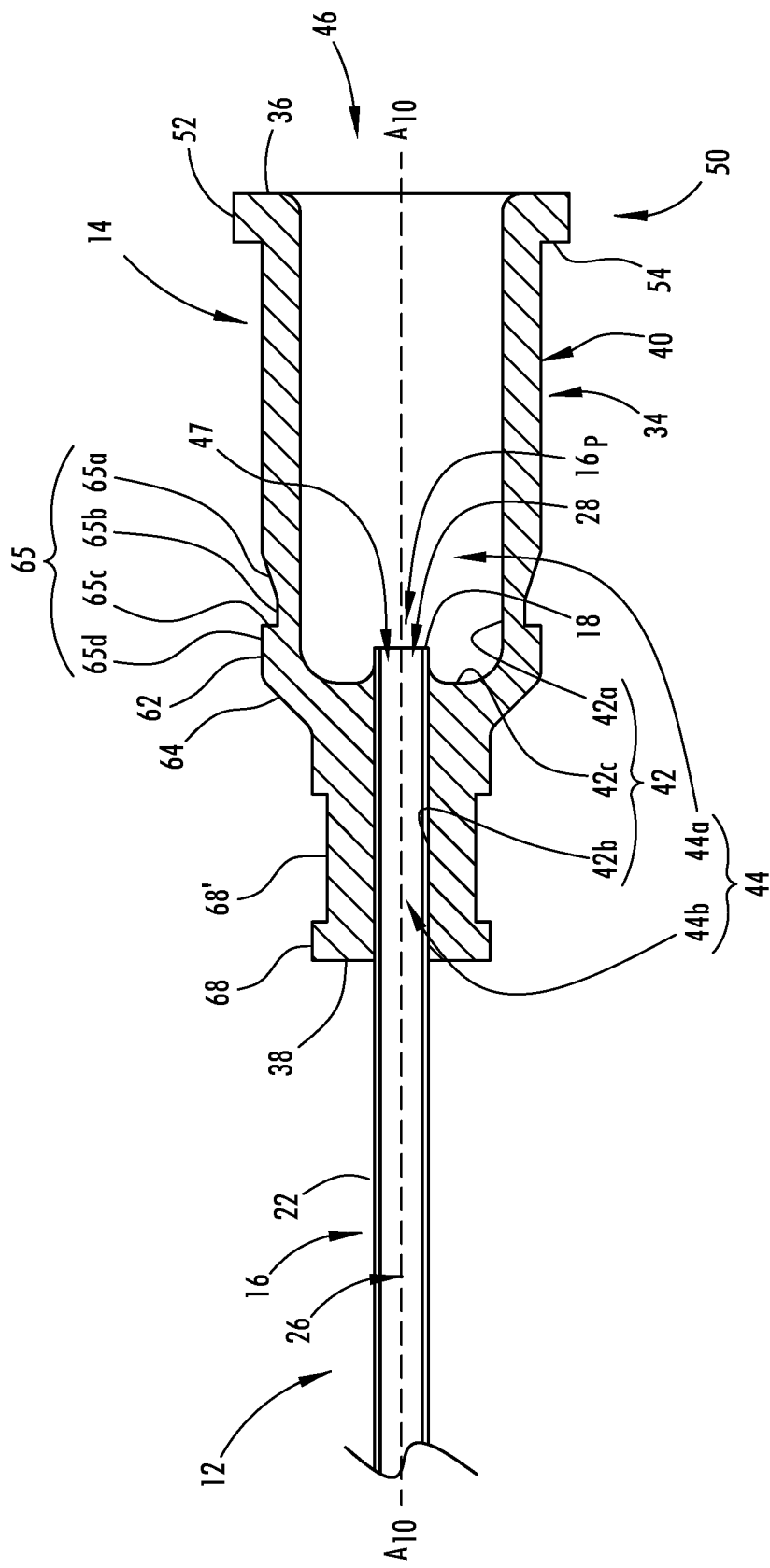
FIG. 11C is a cross-sectional view of an assembled hypodermic interface sub-assembly of FIG. 11B according to line 11'-11' of any of FIG. 12.
Figure 12:
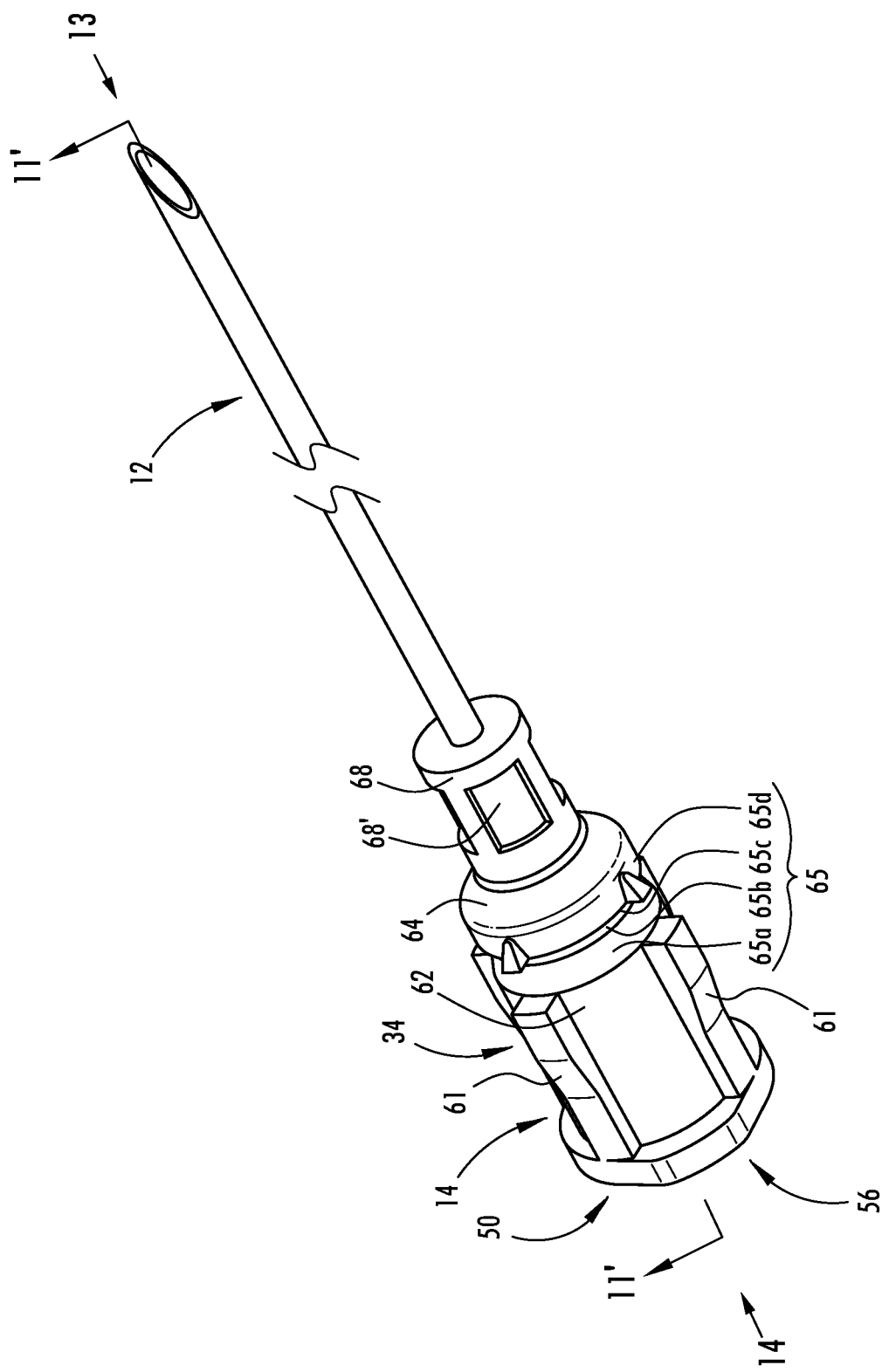
FIG. 12 is an assembled front perspective view of the hypodermic interface sub-assembly of FIG. 11C.
Figure 15:
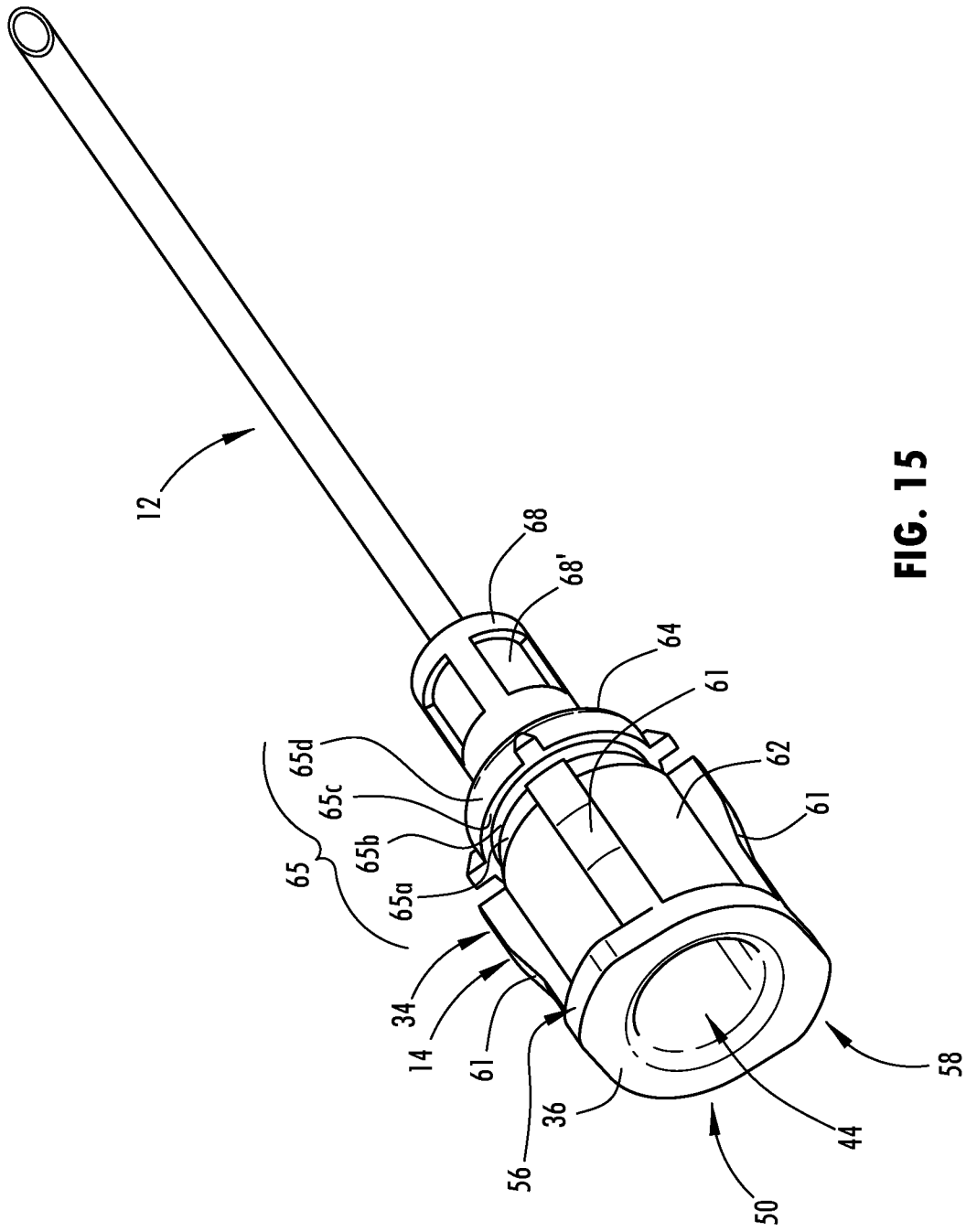
FIG. 15 is an assembled rear perspective view of the hypodermic interface sub-assembly of FIG. 11C.
Figure 16:
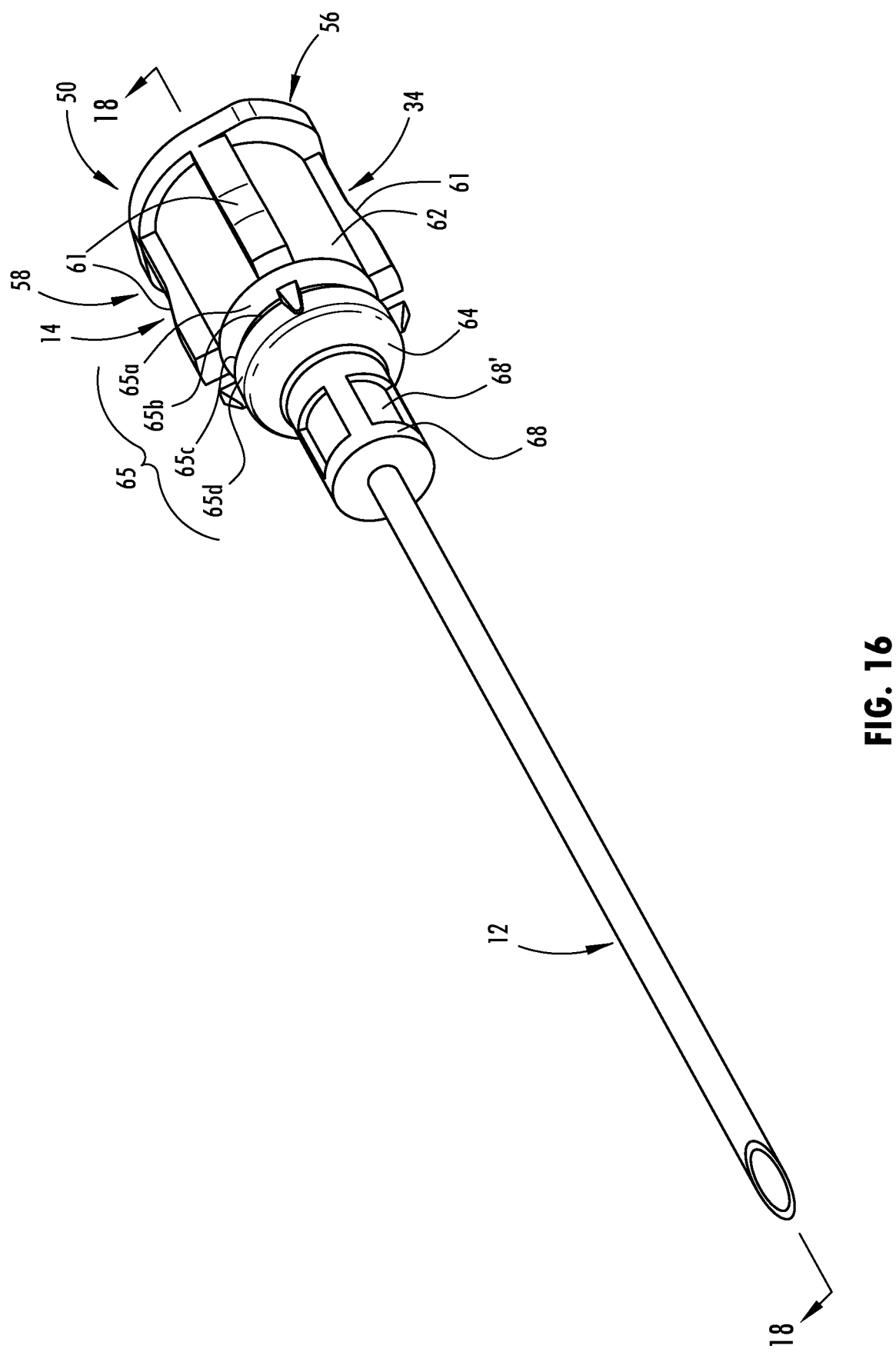
FIG. 16 is another assembled front perspective view of the hypodermic interface sub-assembly of FIG. 11C.
Figure 17:
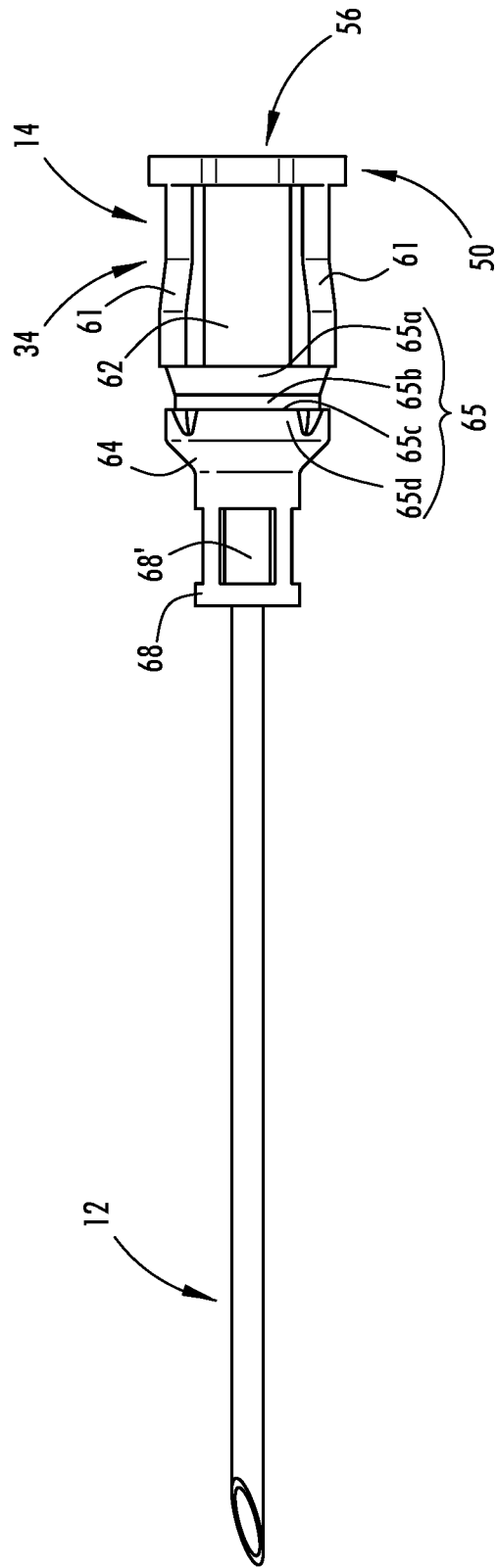
FIG. 17 is a side view of the hypodermic interface sub-assembly of FIG. 11C.
Figure 18:
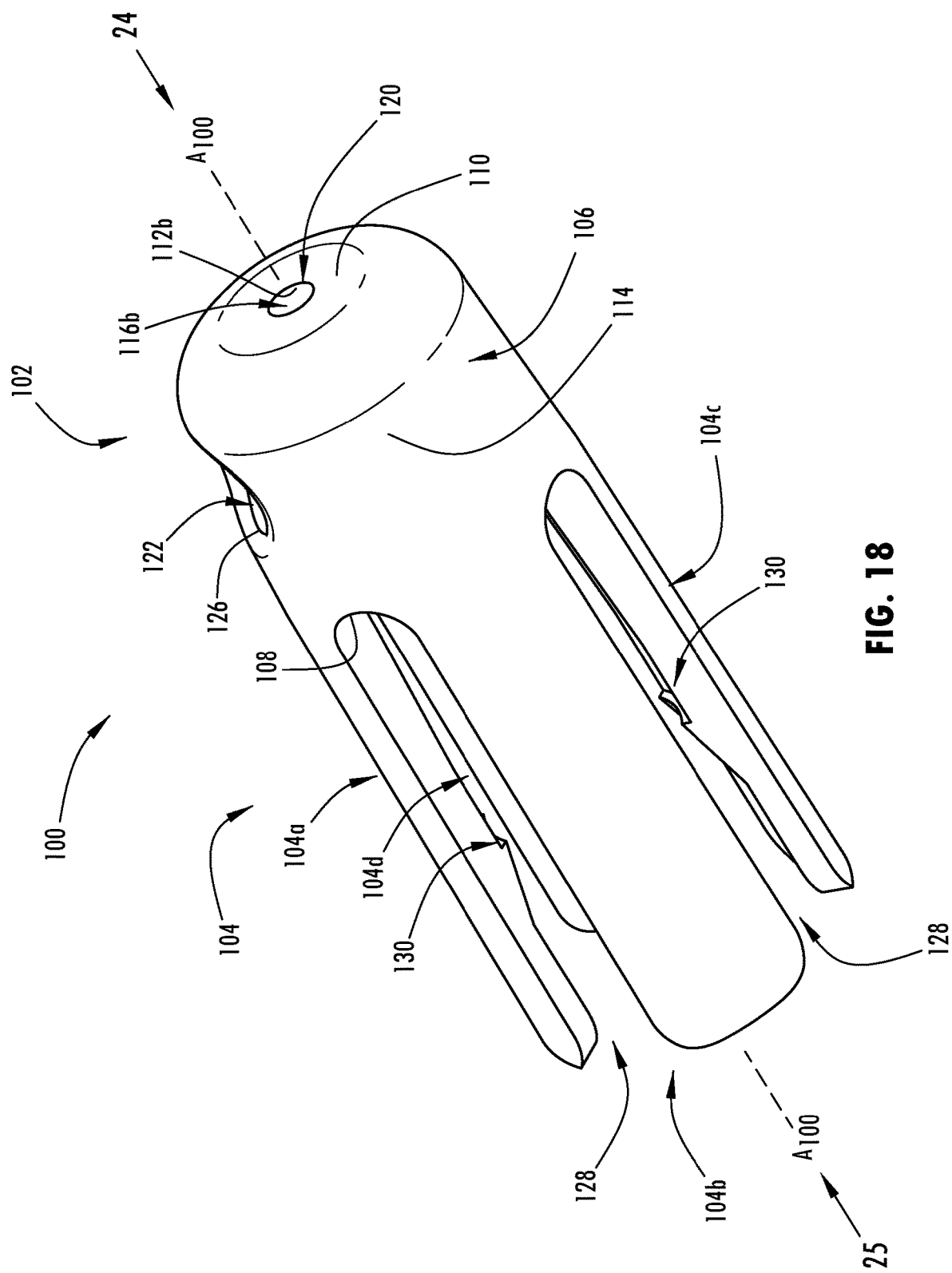
FIG. 18 is a front perspective view of an exemplary cannula carrier of the hypodermic interface assembly of FIG. 1.
Figure 19:
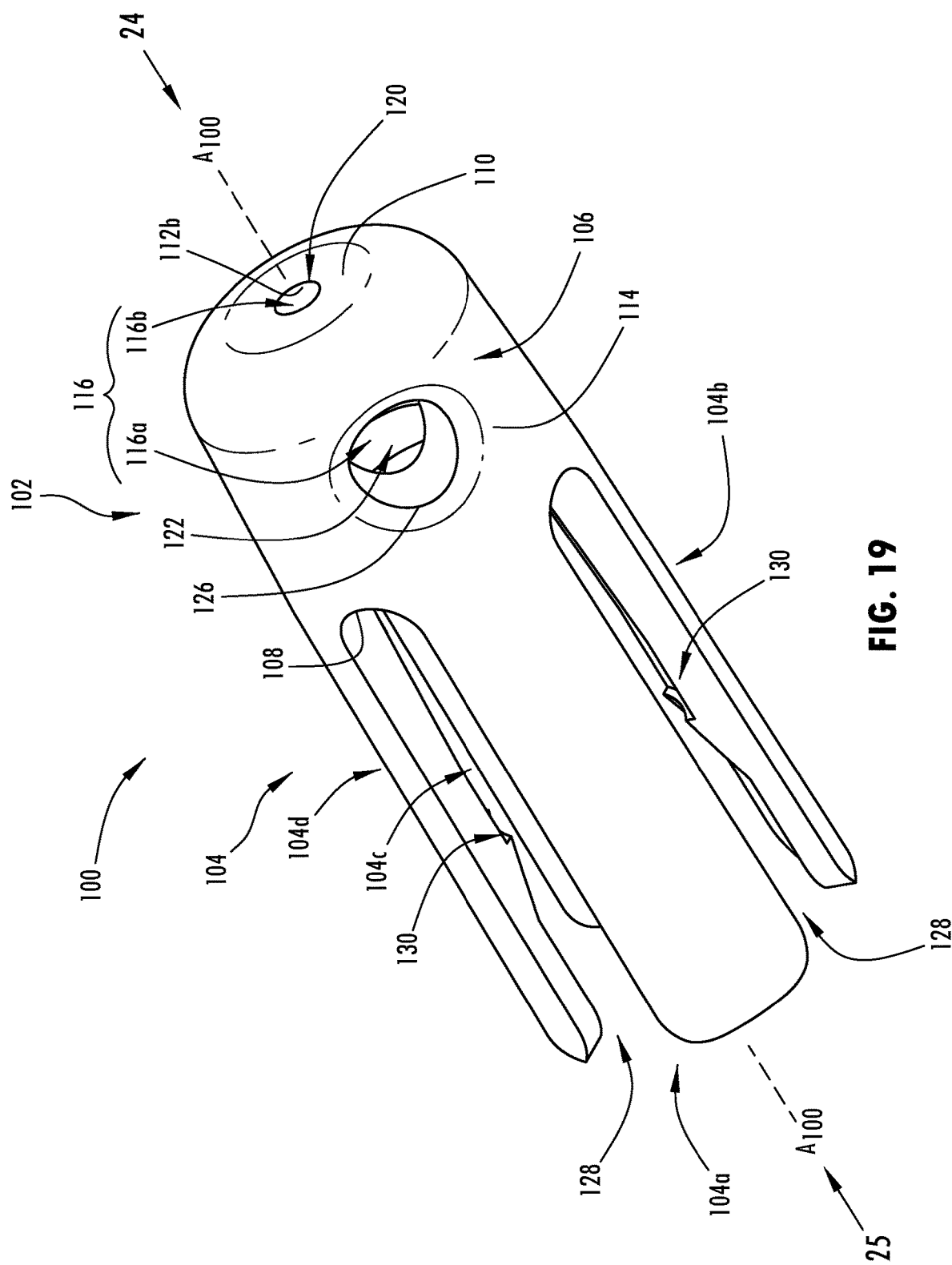
FIG. 19 is another front perspective view of an exemplary cannula carrier of FIG. 18 rotated 90°.

Referring to FIGS. 11A-11C, a method for assembling a sub-assembly (defined by the cannula 12 and the hub 14) of the hypodermic interface assembly 10 (the sub-assembly of which is shown in assembled form at FIGS. 12-17, 28 and 29) is described. Firstly, at FIG. 11A, the components (i.e., the cannula 12 and the hub 14 of the sub-assembly are axially aligned about a central axis $A_{10}$-$A_{10}$ (see also FIG. 1). The central axis $A_{10}$-$A_{10}$ corresponds to, for example, the central axes $A_{12}$-$A_{12}$, $A_{14}$-$A_{14}$ of each of the cannula 12 and the hub 14.

As will be described in the following disclosure, the cannula 12 is mechanically joined to any portion of the hub 14 as a result of, for example, material deformation of at least a portion of, for example, the outer head surface portion 68 of the outer surface 40 of the substantially tube-shaped body 34 of the hub 14 (e.g., by crimping a portion of, for example, outer head surface portion 68 of the outer surface 40 of the substantially tube-shaped body 34 of the hub 14 as seen as FIGS. 11B and 11C). Although the sub-assembly of the hypodermic interface assembly 10 is formed by a mechanical connection, the cannula 12 may alternatively or additionally be joined to any portion of the hub 14, such as, for example, with an adhesive (not shown), such as, for example: an acrylic adhesive, a cyanoacrylate adhesive, a ultra-violet (UV) curable adhesive, or the like. In other configurations the hub 14 may be attached to the cannula 12 by over-molding a material defining the hub 14 relative the cannula 12 (e.g., when the hub 14 is formed from a moldable material such as a plastic material).

As seen at FIG. 11A, a portion of the cannula 12 including the proximal end surface 18 at the proximal end $16_P$ of the tube-shaped body 16 is shown arranged near the distal opening 48 (that is in fluid communication with the second passage portion 44b of the passage 44 of the hub 14) formed by the distal end surface 38 of the hub 14. The central axis $A_{12}$-$A_{12}$ (see, e.g., FIG. 2) of the cannula 12 is axially aligned with the central axis $A_{14}$-$A_{14}$ of the hub 14. The central axes $A_{12}$-$A_{12}$ and $A_{14}$-$A_{14}$ of each of the cannula 12 and the hub 14 correspond to the central axis $A_{10}$-$A_{10}$ (see FIG. 1) of the hypodermic interface assembly 10.

As described above, the outer surface 22 of the tube-shaped body 16 of the cannula 12 defines an outer diameter $D_{12}$ of the cannula 12, and the second passage diameter $D_{44\text{-}2}$ (that defines the second passage portion 44b of the passage 44) is approximately equal to but slightly greater than the outer diameter $D_{12}$ of the cannula 12 so that at least a portion of the second passage portion 44b of the passage 44 is configured to receive the cannula 12. Then, as seen at FIGS. 11B-11C, the proximal end $16_P$ of the tube-shaped body 16 of the cannula 12 is inserted (according to the direction of the arrow Y as seen at FIG. 11A) through the distal opening 48 formed by the distal end surface 38 of the hub 14 and then disposed within at least a portion of the second passage portion 44b of the passage 44 of the hub 14. In some configurations as seen at, for example, FIGS. 11C and 38A-38B, the cannula 12 may be arranged relative the hub 14 such that the proximal end $16_P$ of the tube-shaped body 16 of the cannula 12 is located beyond the third inner surface portion 42c (see, e.g., dashed line P1 at FIG. 38B) of the inner surface 42 of the substantially tube-shaped body 34. As such, a portion of the cannula 12 is arranged within and entirely occupies the second passage portion 44b of the passage 44 of the hub 14 while also being partially disposed within the first passage portion 44a of the passage 44 of the hub 14.

Thereafter, as seen at FIG. 11B, the cannula 12 is arranged within the passage 44 of the hub 14 in order to subsequently, for example, mechanically join the cannula 12 to the hub 14 by, for example, arranging the head surface portion 68 of the outer surface 40 of the substantially tube-shaped body 34 of the hub 14 within, for example, a crimping tool T. The crimping tool T may punch, crimp, swage or materially deform, for example, all or a portion of the head surface portion 68 of the outer surface 40 of the substantially tube-shaped body 34 of the hub 14 in order to mechanically connect all or a portion of the second inner surface portion 42b of the inner surface 42 of the substantially tube-shaped body 34 of the hub 14 to a portion of the length (see, e.g., sub-length $L_{12a2}$ at FIG. 2) of the outer surface 22 of the tube-shaped body 16 of the cannula 12 in a friction-fit relationship, an interference-fit relationship, or a mechanically-coupled relationship.

Accordingly, as seen at FIG. 11C, the cannula 12 may be mechanically joined to the hub 14 as a result of the material deformation of the portion of the hub 14 by the crimping tool T. In some configurations as seen at FIG. 11C and FIGS. 12 and 15-17 and 28, the crimping tool T may punch, crimp, swage or materially deform, for example, a portion of the outer surface 40 of the substantially tube-shaped body 34. In some implementations, for example, the crumping tool T may punch, crimp, swage or materially deform (see, e.g., reference numeral 68'), for example, a portion or all of the outer head surface portion 68 of the outer surface 40 of the substantially tube-shaped body 34. Accordingly, in such implementations, the outer head surface portion 68 of the outer surface 40 of the substantially tube-shaped body 34 may define crimping pockets (see, e.g., reference numeral 68') that infer material deformation of the outer head surface portion 68 of the outer surface 40 of the substantially tube-shaped body 34, and, as a result, distinguishes a "deformed" hub 14 that is mechanically connected to the cannula 12 from a virgin or "non-deformed" hub 14 (see, e.g., FIGS. 3-10) having an outer head surface portion 68 of the outer surface 40 of the substantially tube-shaped body 34 that does not define crimping pockets 68'.

As described above, a portion of the length (e.g., sub-length $L_{12a2}$) of the outer surface 22 of the tube-shaped body 16 of the cannula 12 may be disposed within the second passage portion 44b of the passage 44 of the hub 14 and may be mechanically secured (see, e.g., FIG. 11C) to at least a portion of the second inner surface portion 42b of the inner surface 42 of the substantially tube-shaped body 34 of the hub 14, which may extend along a sub-length of the hub 14 defined by the length $L_{14a}$ (see, e.g., FIG. 7) of the outer head surface portion 68 of the outer surface 40 of the substantially tube-shaped body 34 of the hub 14. Additionally, with reference to FIGS. 11C and 38A, a further portion of the length (e.g., sub-length $L_{12a3}$ at FIG. 2) of the outer surface 22 of the tube-shaped body 16 of the cannula 12 may be disposed within the second passage portion 44b of the passage 44 of the hub 14, and may extend along the sub-length of the hub 14 defined by the length $L_{14a}$ the head surface portion 68 of the outer surface 40 of the substantially tube-shaped body 34 of the hub 14. As such, in some implementations, a portion of the sub-length $L_{14a}$ of the length $L_{14}$ of the hub 14 may not be materially deformed by the crimping tool T. For example, the sub-length $L_{12a3}$ of the cannula 12 may not be mechanically coupled to the hub 14 along the portion of the sub-length $L_{14a}$ of the head surface portion 68 of the outer surface 40 of the substantially tube-shaped body 34 of the hub 14.

Furthermore, as seen at FIGS. 11C and 38A, a portion of the length (see, e.g., length portion $L_{12a4}$) of the outer surface 22 of the tube-shaped body 16 of the cannula 12 may be disposed within the second passage portion 44b of the passage 44 of the hub 14, which may extend along a sub-length of the hub 14 defined by a portion of the length $L_{14a}$ of the outer shoulder surface portion 64 of the outer surface 40 of the substantially tube-shaped body 34 of the hub 14. With reference to FIGS. 2, 11C, and 38A a remainder/length portion (see, e.g., length portion $L_{12c}$) of the outer surface 22 of the tube-shaped body 16 of the cannula 12 extends beyond the distal end surface 38 of the hub 14 and is not contained within the passage 44 of the hub 14.

With reference to FIGS. 28-32, in addition to the cannula 12 being joined to the hub 14 to define the sub-assembly (defined by the cannula 12 and the hub 14), the subassembly may be joined to the cannula carrier 100 to further define the hypodermic interface assembly 10 (and the adhesive 200 may be deposited and then cured). The hypodermic interface assembly 10 may be joined to an injection gun I (see, e.g., FIG. 40). As will be described in the following disclosure at FIGS. 41A-41G, the second portion 10b of the hypodermic interface assembly 10 is configured to controllably separate from the first portion 10a of the hypodermic interface assembly 10 (see, e.g., FIGS. 35A-35B, 36A-36B, and 37A-37B). With reference to FIGS. 18-27H, an exemplary cannula carrier 100 is now described.

Figure 20:
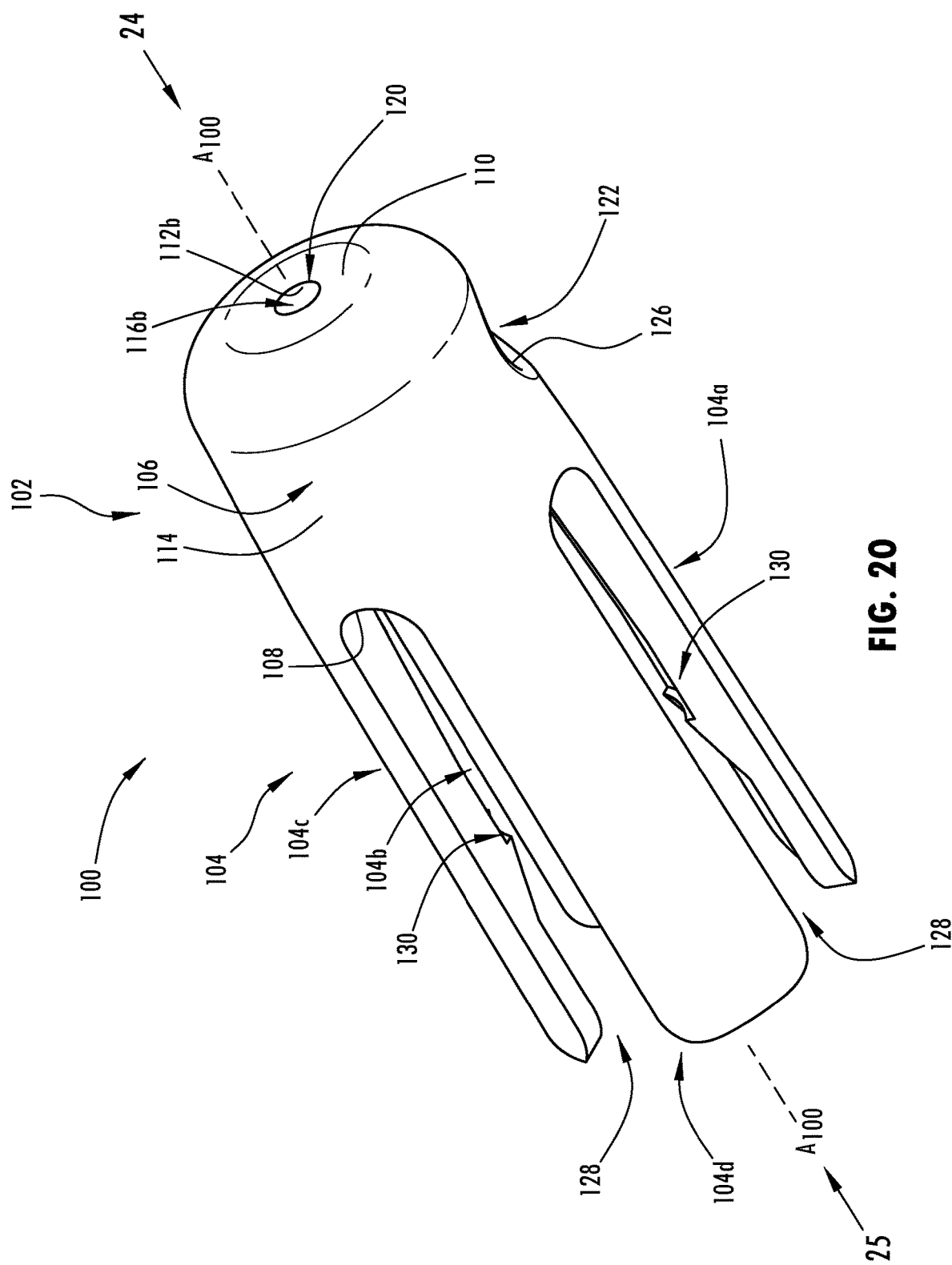
FIG. 20 is another front perspective view of an exemplary cannula carrier of FIG. 19 rotated 90°.
Figure 21:
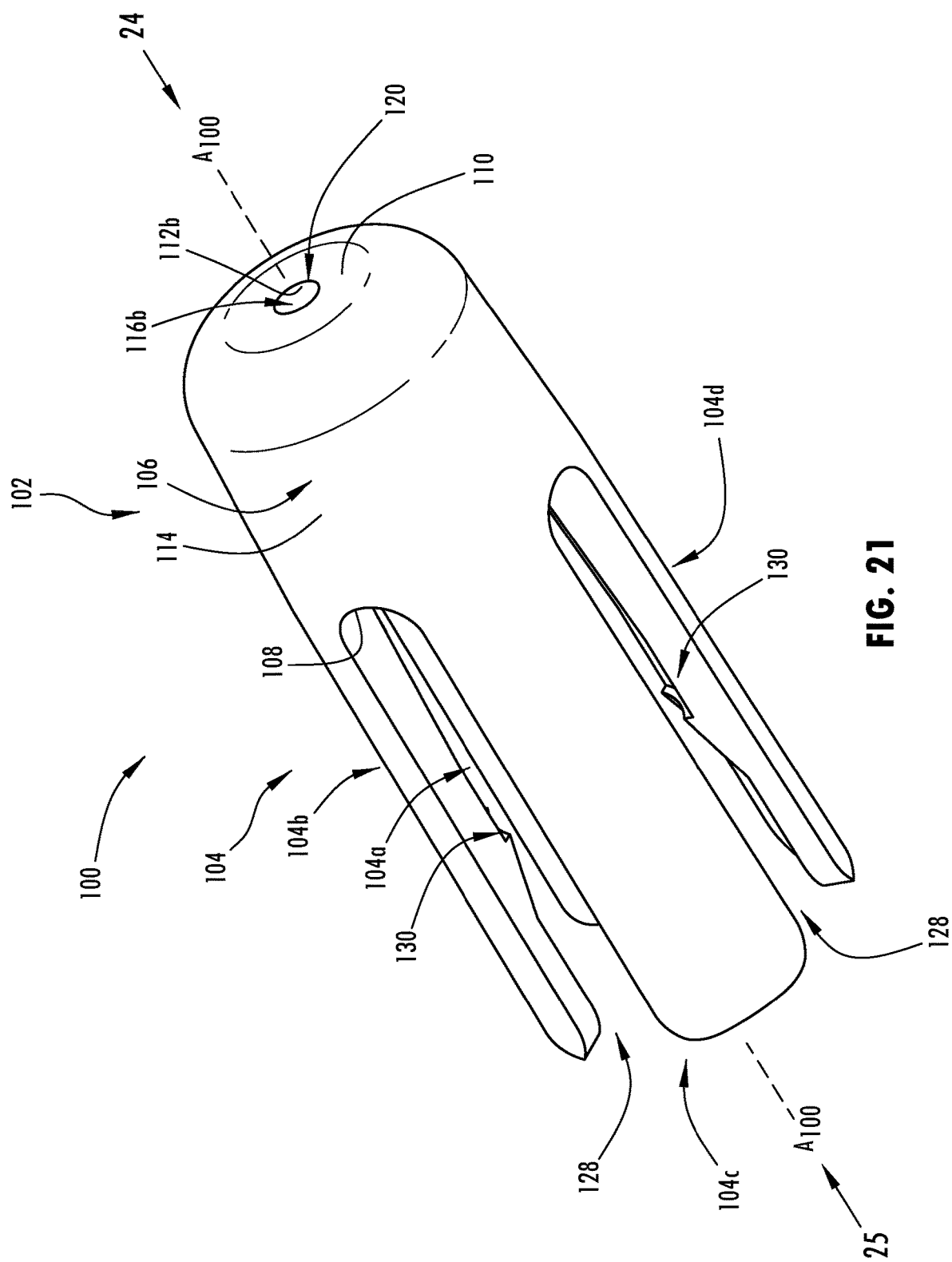
FIG. 21 is another front perspective view of an exemplary cannula carrier of FIG. 20 rotated 90°.
Figure 22:
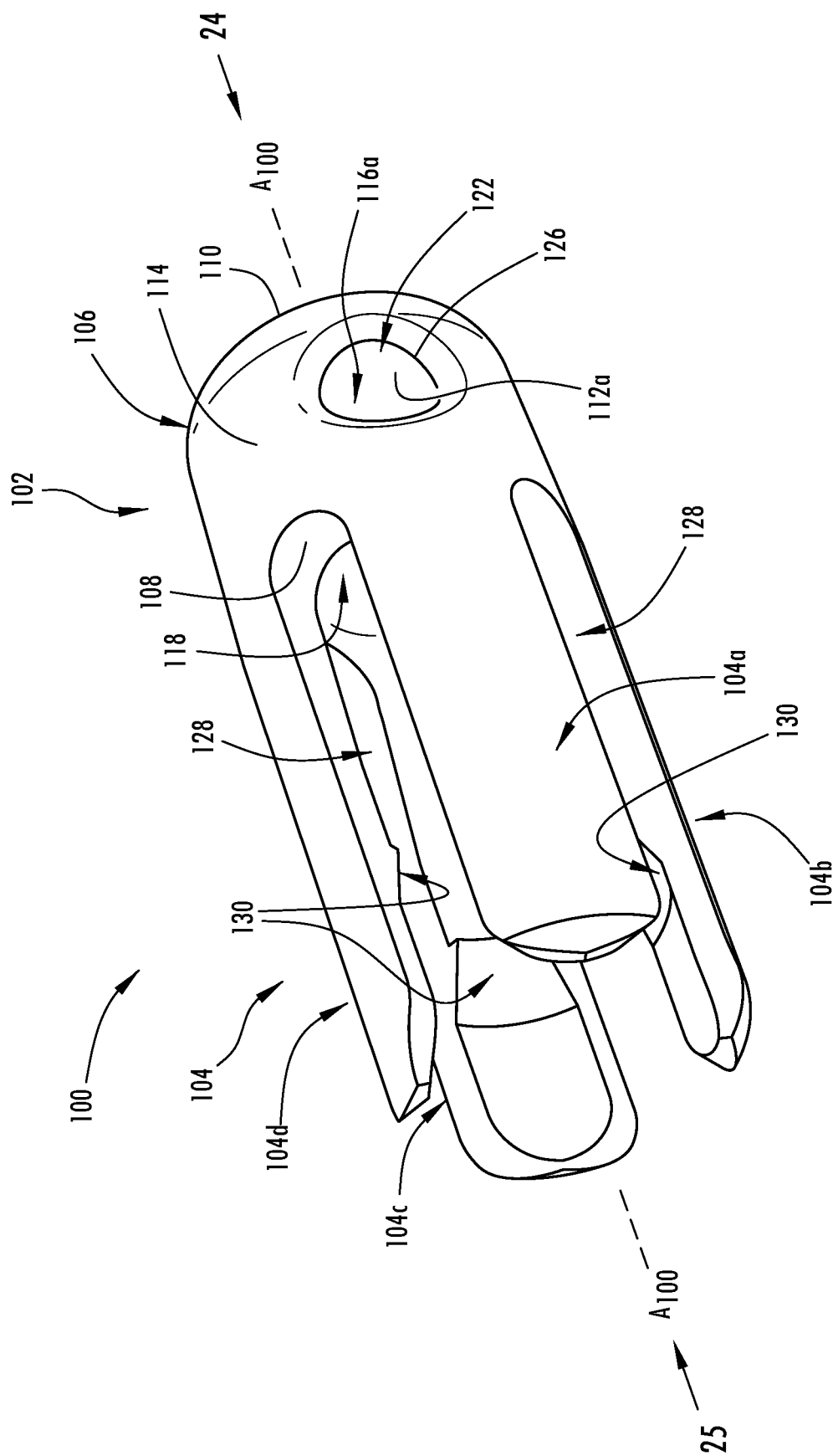
FIG. 22 is a rear perspective view of the cannula carrier of FIG. 18.
Figure 23:
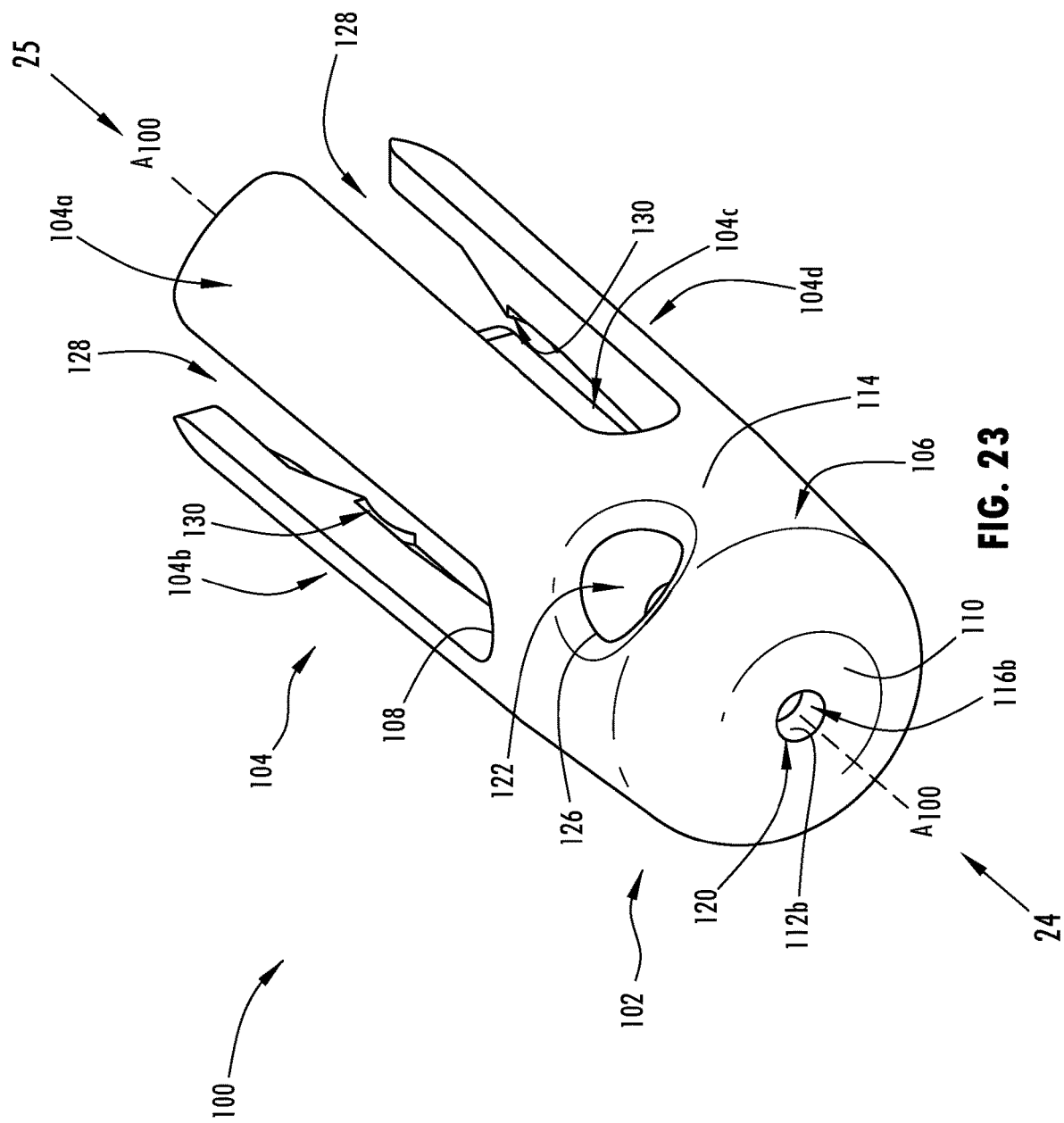
FIG. 23 is another front perspective view of the cannula carrier of FIG. 18.
Figure 26A:
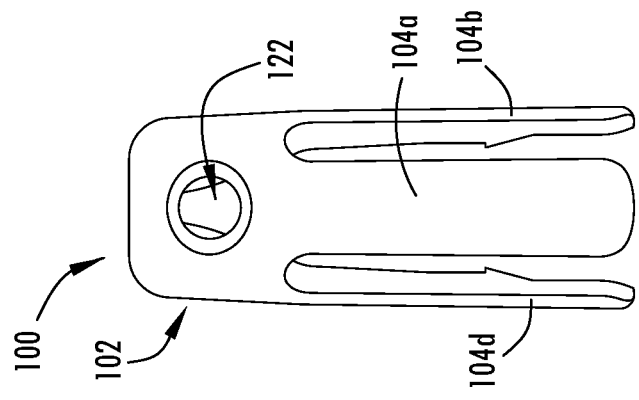
FIG. 26A is a side view of the cannula carrier of FIG. 18.
Figure 26B:
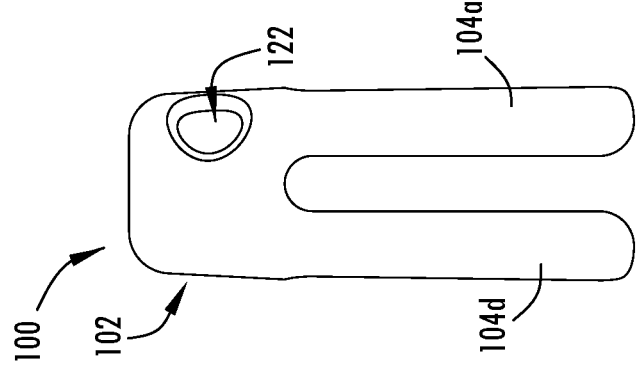
FIG. 26B is a side view of the cannula carrier of FIG. 26A rotated 45°.
Figure 26C:
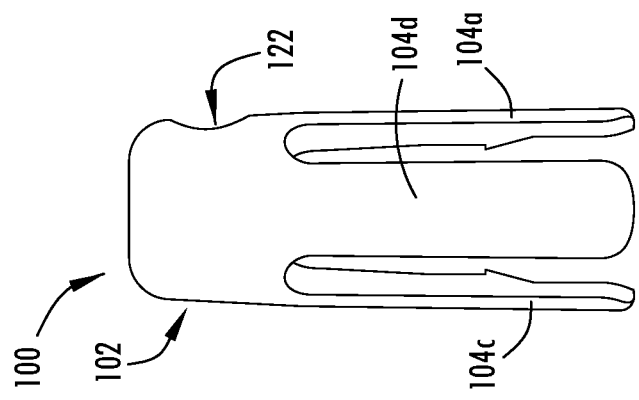
FIG. 26C is a side view of the cannula carrier of FIG. 26B rotated 45°.
Figure 26D:
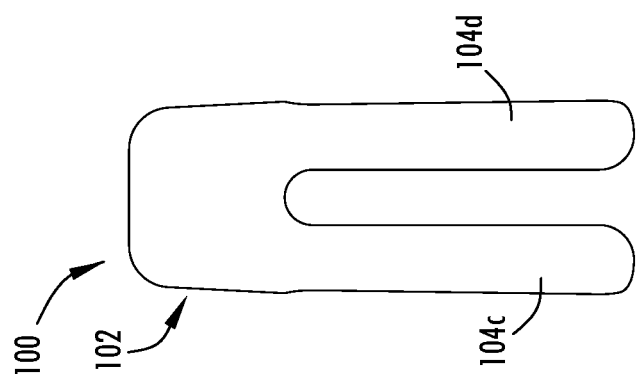
FIG. 26D is a side view of the cannula carrier of FIG. 26C rotated 45°.
Figure 27A:
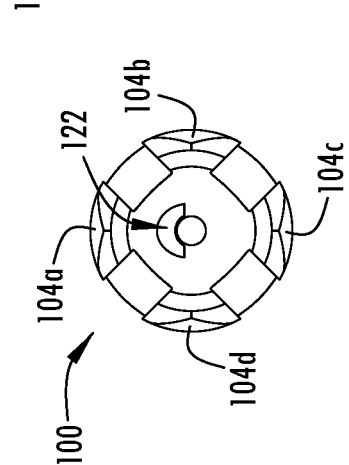
FIG. 27A is a bottom view of the cannula carrier corresponding to FIG. 26A.
Figure 27B:
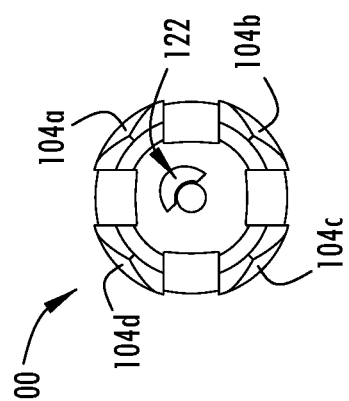
FIG. 27B is a bottom view of the cannula carrier corresponding to FIG. 26B.
Figure 27C:
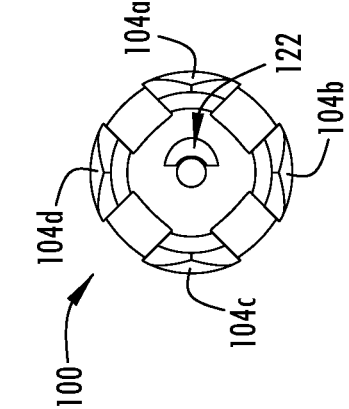
FIG. 27C is a bottom view of the cannula carrier corresponding to FIG. 26C.
Figure 27D:
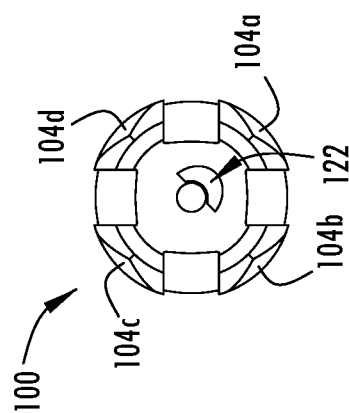
FIG. 27D is a bottom view of the cannula carrier corresponding to FIG. 26D.

Referring to FIGS. 18-21, an exemplary cannula carrier 100 includes a head portion 102 and a plurality of leg portions 104 defined by, for example, four leg portions including a first leg portion 104a (see, e.g., FIG. 19), a second leg portion 104b (see, e.g., FIG. 18), a third leg portion 104c (see, e.g., FIG. 21), and a fourth leg portion 104d (see, e.g., FIG. 20). The head portion 102 includes a body 106 extending between a proximal end surface 108 and a distal end surface 110. The body 106 is also defined by a thickness $T_{106}$ (see, e.g., FIG. 29) extending between an inner surface 112 (see, e.g., FIG. 29) and an outer surface 114. The cannula carrier 100 may be formed using any desirable manufacturing procedure such as, for example: a molding procedure; a casting procedure; a machining procedure; or a combination thereof. The cannula carrier 100 may be made from any desirable material such as, for example: a metallic material; a plastic material; or a combination thereof. In some examples, the cannula carrier 100 may be made with a high visibility dye or pigment such as, for example, a brightly colored pigment, a fluorescent pigment, a phosphorescent pigment, retroreflective partially mirrored glass beads, metallic flake pigment, or the like that preferably is not similar to the flesh tone or color of the surface $S_S$ of the flesh of the animalia. Furthermore, when the cannula carrier 100 is formed, the cannula carrier 100 may include an over-molded RFID component (not shown) embedded in the material or an RFID sticker (not shown) or other identifying information disposed upon one or more of the inner surface 112 and the outer surface 114 of the cannula carrier 100 in order to determine the location and/or serial number or other identifier associated with the cannula carrier 100.

With reference to FIG. 29, the inner surface 112 of the body 106 of the head portion 102 of the cannula carrier 100 defines an axial passage 116. Access to the axial passage 116 is permitted by a proximal opening 118 (see, e.g., FIGS. 22, 25, and 27A-27H) and a distal opening 120 (see, e.g., FIGS. 18-21, 23, and 24). Furthermore, the inner surface 112 includes a first inner surface portion 112a defining a first passage portion 116a. The inner surface 112 also includes a second inner surface portion 112b defining a second passage portion 116b that is in fluid communication with the first passage portion 116a. The first inner surface portion 112a extends from the proximal end surface 108 and defines the proximal opening 118. The second inner surface portion 112b extends from the distal end surface 110 and defines the distal opening 120.

The first passage portion 116a is defined by a first passage diameter $D_{116a}$ (see, e.g., FIG. 29) and the second passage portion 116b is defined by a second passage diameter $D_{116b}$ (see, e.g., FIG. 29). The first passage diameter $D_{116a}$ is greater than the second passage diameter $D_{116b}$. The second passage diameter $D_{116b}$ is approximately equal to but slightly greater than the outer diameter $D_{12}$ of the cannula 12 so that at least a portion of the second passage portion 116b defined by the second inner surface portion 112b of the inner surface 112 of the body 106 of the head portion 102 of the cannula carrier 100 is configured to receive the cannula 12. As will be described in the following disclosure at FIGS. 28-31, upon arranging the cannula 12 within the second passage portion 116b, a portion $L_{12a1}$ of the length $L_{12}$ of the cannula 12 see, FIG. 2) may be arranged within the second passage portion 116b of the head portion 102 of the cannula carrier 100 such that the outer surface 22 of the tube-shaped body 16 of cannula 12 may be friction-fit-coupled to the second inner surface portion 112b of the inner surface 112 of the body 106 of the head portion 102 of the cannula carrier 100 in order to "plug" or "fluidly seal" the distal opening 120 of the cannula carrier (100).

Referring to FIGS. 18-20, 22, 23, 26A-26C, and 26G-26H, the body 106 of the head portion 102 of the cannula carrier 100 also defines a radial passage 122 that extends through the thickness $T_{106}$ body 106 of the head portion of the cannula carrier 100. As seen at FIG. 29, access to the radial passage 122 is provided by an inner surface opening 124 defined by the inner first inner surface portion 112a of the inner surface 112 of the body 106 of the cannula carrier 100 (i.e., the radial passage 122 is in direct fluid communication with the first passage portion 116a. With reference to any of FIGS. 18-20, 22, 23, 26A-26C, and 26G-26H, access to the radial passage 122 is also provided by an outer surface opening 126 defined by the outer surface 114 of the body 106 of the head portion 102 of the cannula carrier 100. As seen at, for example, FIG. 19, the radial passage 122 may be axially aligned with a leg portion 104, e.g., the first leg portion 104a of the plurality of leg portions 104, of the cannula carrier 100.

Each leg portion 104a, 104b, 104c, 104d axially extends from the proximal end surface 108 of the body 106 of the head portion 102 of the cannula carrier 100. Collectively, the leg portions 104a, 104b, 104c, 104d circumscribe a central axis $A_{100}$-$A_{100}$ extending through an axial center of the cannula carrier 100 and each may be circumferentially offset approximately 90° from an adjacent leg portion 104a, 104b, 104c, 104d, defining an axial gap 128 between each adjacent leg portion 104a, 104b, 104c, 104d.

Furthermore, with reference to, for example, FIGS. 18-23, each leg portion 104a, 104b, 104c, 104d is defined by a proximal barb portion 130. As seen at FIG. 29, each proximal barb portion 130 is defined by a plurality of barb surface portions 130a, 130b, 130c, 130d that may be configured to matingly-couple with the surface portions 65a, 65b, 65c, 65d that define the circumferential notch or groove 65 that extends into the outer body surface portion 62 of the outer surface 40 of the substantially tube-shaped body 34 of the hub 14. Each leg portion 104a, 104b, 104c, 104d may extend in a proximal direction beyond each barb surface portion 130a, 130b, 130c, 130d such that each leg portion 104a, 104b, 104c, 104d provides additional engagement with each rib 60a, 60b, 60c, 60d in order to transmit torque between the needle carrier 100 and the hub 14 (e.g., in order to engage and disengage the Luer lock mechanism).

As seen at FIGS. 28 and 29, a portion of the cannula 12 including the proximal end surface 18 at the proximal end $16_P$ of the tube-shaped body 16 is shown arranged near the distal opening 120 formed by the distal end surface 110 of the body 106 of the head portion 102 of the cannula carrier 100. The central axis $A_{12}$-$A_{12}$ (see, e.g., FIG. 2) of the cannula 12 is axially aligned with the central axis $A_{100}$-$A_{100}$ of the cannula carrier 100. The central axes $A_{12}$-$A_{12}$ and $A_{100}$-$A_{100}$ of each of the cannula 12 and the cannula carrier 100 correspond to the central axis $A_{10}$-$A_{10}$ (see FIG. 1) of the hypodermic interface assembly 10.

As described above, the outer surface 22 of the tube-shaped body 16 of the cannula 12 defines an outer diameter $D_{12}$ of the cannula 12, and the second passage diameter $D_{116b}$ that defines the second passage portion 116b of the passage 116 is approximately equal to but slightly greater than the outer diameter $D_{12}$ of the cannula 12 so that at least a portion of the second passage portion 116b of the passage 116 defined by the body 106 of the cannula carrier 100 that is configured to receive the cannula 12 may result in the portion $L_{12a1}$ of the length $L_{12}$ tube-shaped body 16 of the cannula 12 "plugging" or "fluidly sealing" the distal opening 120 of the cannula carrier 100. Accordingly, as seen at FIGS. 29-30, the distal end $16_D$ of the tube-shaped body 16 of the cannula 12 is inserted (according to the direction of the arrow Y as seen at FIG. 29) through the proximal opening 118 formed by the proximal end surface 108 of the body 106 of the head portion 102 of the cannula carrier 100 and into the first passage portion 116a of the passage 116 for subsequent disposal within the second passage portion 116b of the passage 116.

Thereafter, the distal end $16_D$ of the tube-shaped body 16 of the cannula 12 is inserted through the distal opening 120 of the cannula carrier 100 such that a portion $L_{12c}$ of the length $L_{12}$ of the tube-shaped body 16 of the cannula 12 extends beyond the distal end surface 110 of the body 106 of the head portion 102 of the cannula carrier 100. Advancement of the tube-shaped body 16 of the cannula 12 through the distal opening 120 of the cannula carrier 100 continues until the proximal barb portion 130 of each leg portion 104a, 104b, 104c, 104d of the plurality of leg portions 104 slides and flexes over the outer shoulder surface portion 64 of the outer surface 40 of the substantially tube-shaped body 34 of the hub 14 and then slides past and then flexes into for subsequent registration within the circumferential notch or groove 65. Once each leg portion 104a, 104b, 104c, 104d of the plurality of leg portions 104 is registered within the circumferential notch or groove 65, the plurality of barb surface portions 130a, 130b, 130c, 130d of each proximal barb portion 130 of each leg portion 104a, 104b, 104c, 104d of the plurality of leg portions 104 are disposed adjacent and matingly-coupled with the surface portions 65a, 65b, 65c, 65d that define the circumferential notch or groove 65 in order to mechanically couple the cannula carrier 100 to the hub 14.

Figure 31:
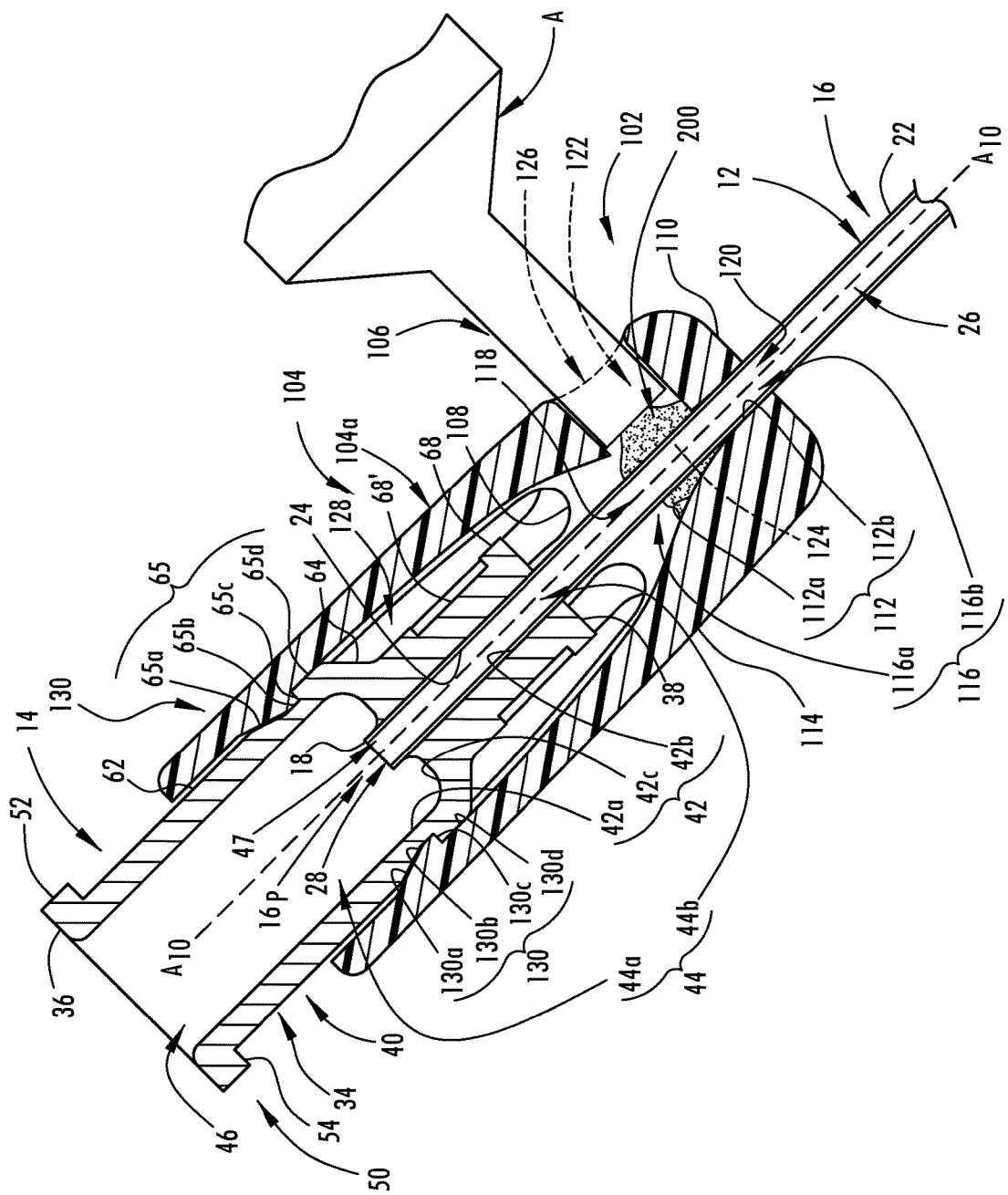
FIG. 31 is another cross-sectional view according to FIG. 30 illustrating an adhesive being metered into a passage portion of the cannula carrier for non-removably-joining the cannula carrier to the cannula of the hypodermic interface sub-assembly.

With reference to FIG. 31, after the cannula carrier 100 is mechanically coupled to the hub 14, an amount of adhesive 200 is disposed within the first passage portion 116a of the passage 116 defined by the body 106 of the cannula carrier 100 for non-removably-coupling the cannula 12 to the cannula carrier 100. The adhesive 200 may be deposited or injected into the first passage portion 116a of the passage 116 defined by the body 106 of the cannula carrier 100 by way of the radial passage 122 that extends through the thickness $T_{106}$ body 106 of the head portion of the cannula carrier 100. In some instances, the radial passage 122 may be sized to receive a nozzle of an adhesive applicator A (as seen at, e.g., FIG. 31). Although the cannula carrier 100 is described above to be adhesively coupled to the cannula 12 with the adhesive 200, the cannula 100 could alternatively and/or additionally mechanically coupled to the cannula 12 by way of, for example, a material deformation process associated with, for example, swaging, crimping, welding, or the like. Exemplary welding procedures may include electron beam welding, ultrasonic welding, or the like.

Figure 32:
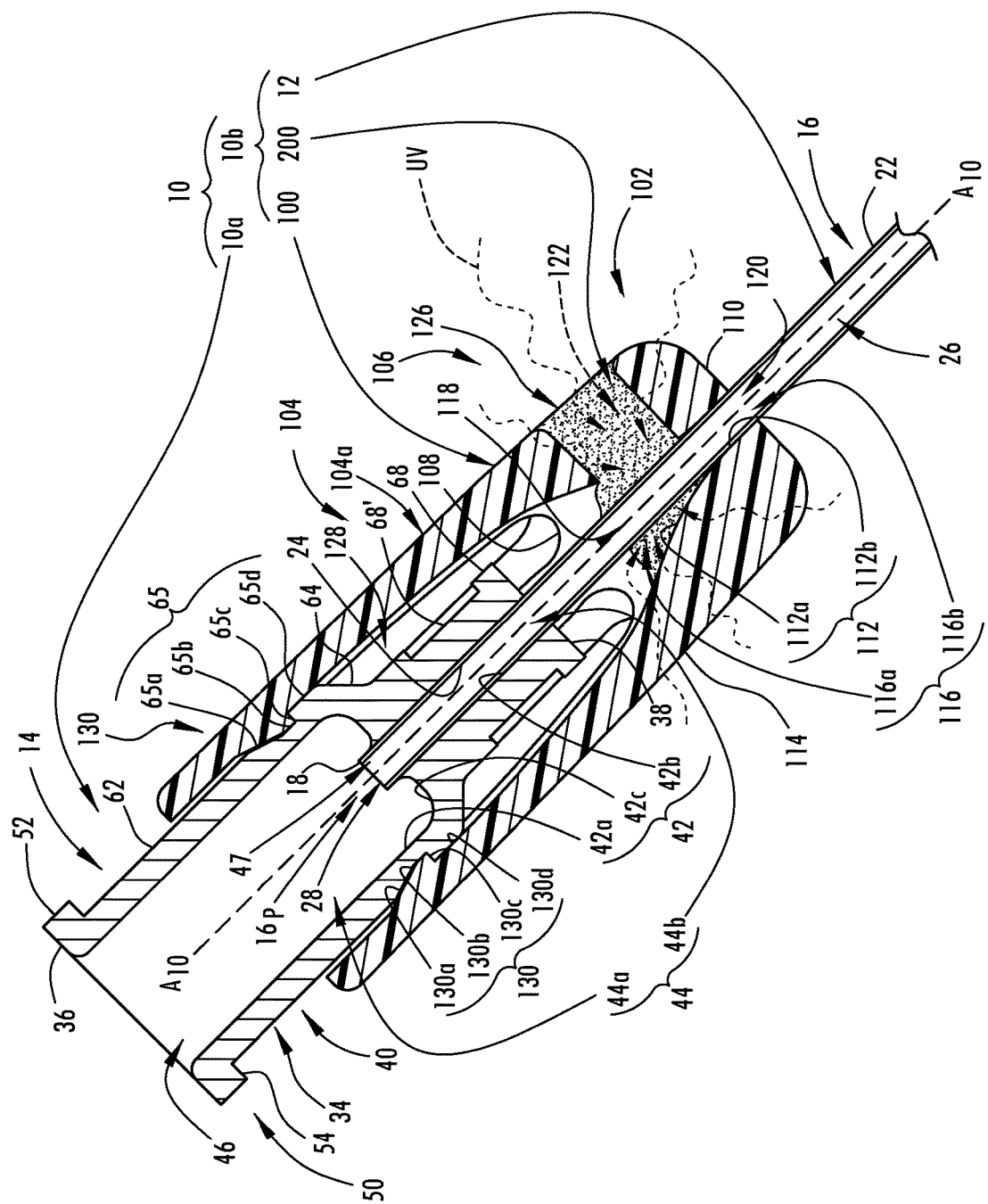
FIG. 32 is another cross-sectional view according to FIG. 31 illustrating light that cures the adhesive that non-removably-joins the cannula carrier to the cannula of the hypodermic interface sub-assembly.
Figure 33:
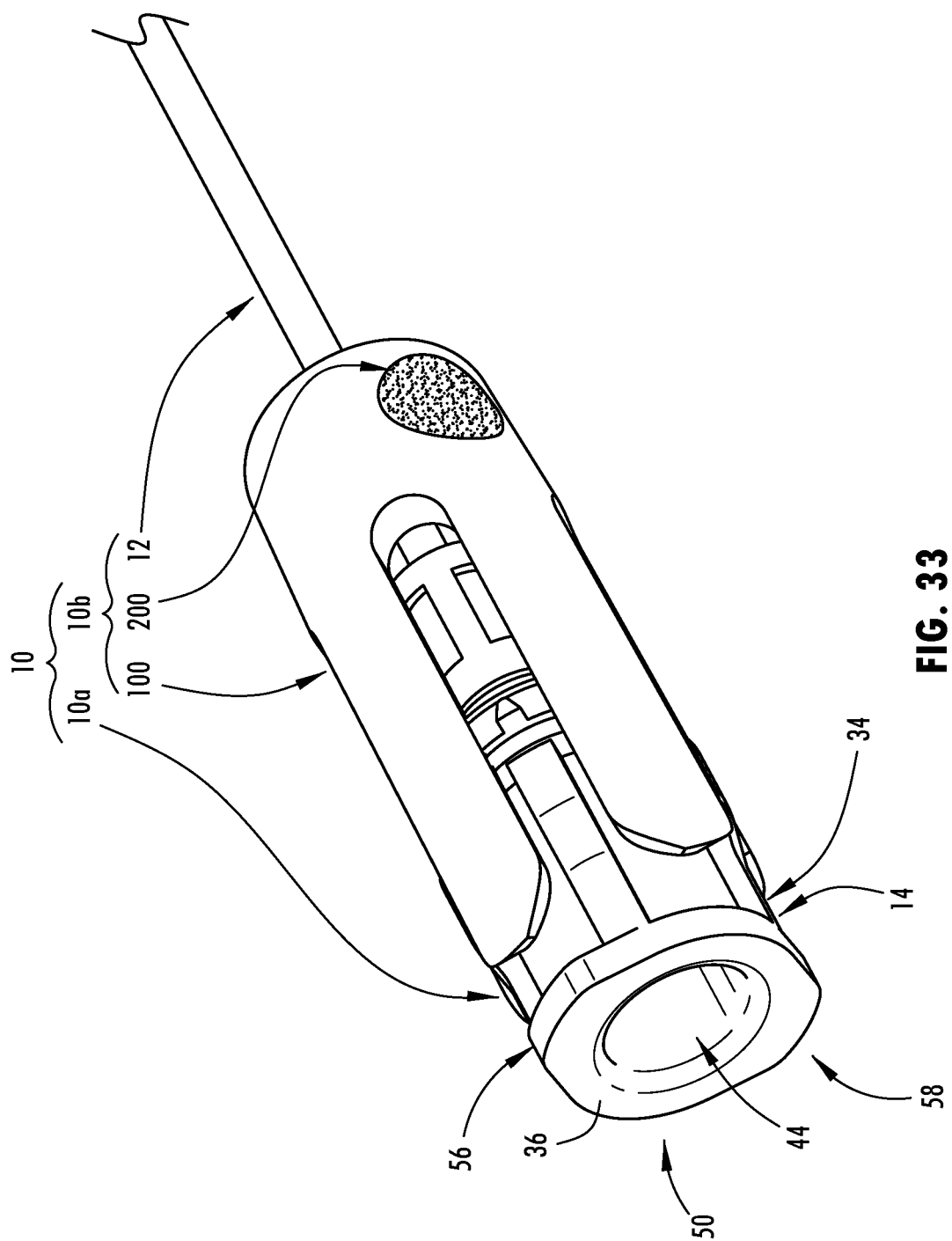
FIG. 33 is an assembled rear perspective view of the hypodermic interface assembly of FIG. 1.

As seen at FIG. 32, the adhesive 200 may fill at least a portion of, or all of, the first passage portion 116a of the passage 116 defined by the body 106 of the cannula carrier 100. In other configurations, the adhesive 200 may also fill at least a portion or all of the radial passage 122.

Once the desired amount of adhesive 200 is deposited into the first passage portion 116a, the adhesive 200 may surround and be disposed adjacent: (1) a portion $L_{12a1}$ of the length $L_{12}$ defined by the outer surface 22 of the tube-shaped body 16 of the cannula 12 that is arranged within the first passage portion 116a; and (2) at least a portion of the first inner surface portion 112a that defines the first passage portion 116a for non-removably and adhesively joining the cannula 12 to the cannula carrier 100. In some configurations, the adhesive 200 is an acrylic adhesive, a cyanoacrylate adhesive, a ultra-violet (UV) curable adhesive, or the like. As seen at FIG. 32, if the adhesive 200 is a UV curable adhesive, a UV light source (not shown) may be utilized for directing ultra violet light UV toward the adhesive 200 for curing the adhesive 200. Once the adhesive 200 has cured, the hypodermic interface assembly 10 may be said to be formed as seen at FIGS. 33-35B.

Although the exemplary design of the hypodermic interface assembly 10 utilizes both of: (1) the proximal barb portion 130 of each leg portion 104a, 104b, 104c, 104d to mechanically-join the cannula carrier 100 to the hub 14; and (2) adhesive 200 for adhesively-joining cannula carrier 100 to the cannula 12, some implementations of the hypodermic interface assembly 10 may include one of a mechanical coupling and/or an adhesive coupling. For example, the hypodermic interface assembly 10 may be only mechanically-joined by friction-fit connecting the cannula 12 to the cannula carrier 100 (i.e., the adhesive 200 may be excluded from such an exemplary implementation of a hypodermic interface assembly) and the proximal barb portion 130 of each leg portion 104a, 104b, 104c, 104d.

Figure 34:
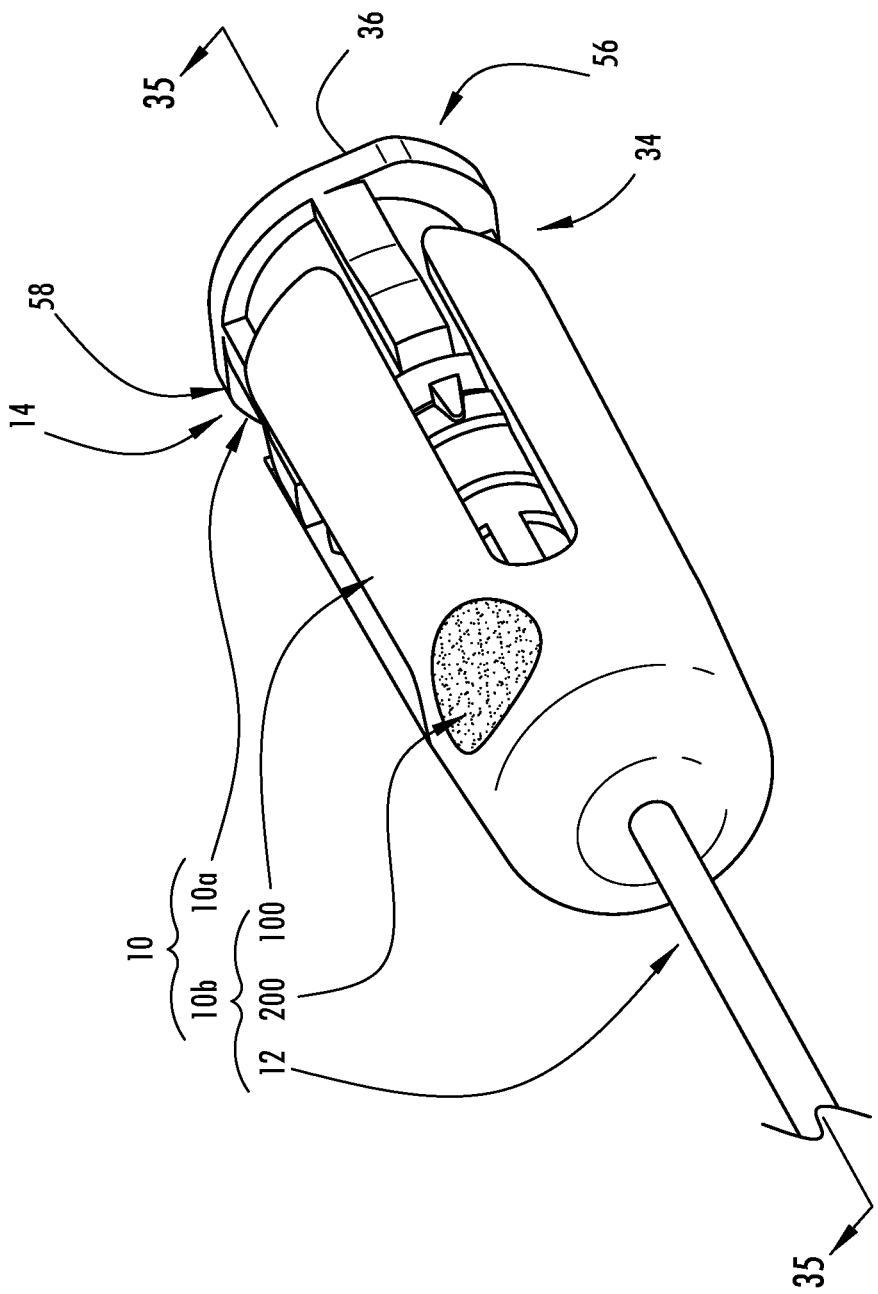
FIG. 34 is another assembled front perspective view of the hypodermic interface assembly of FIG. 1.
Figure 35A:
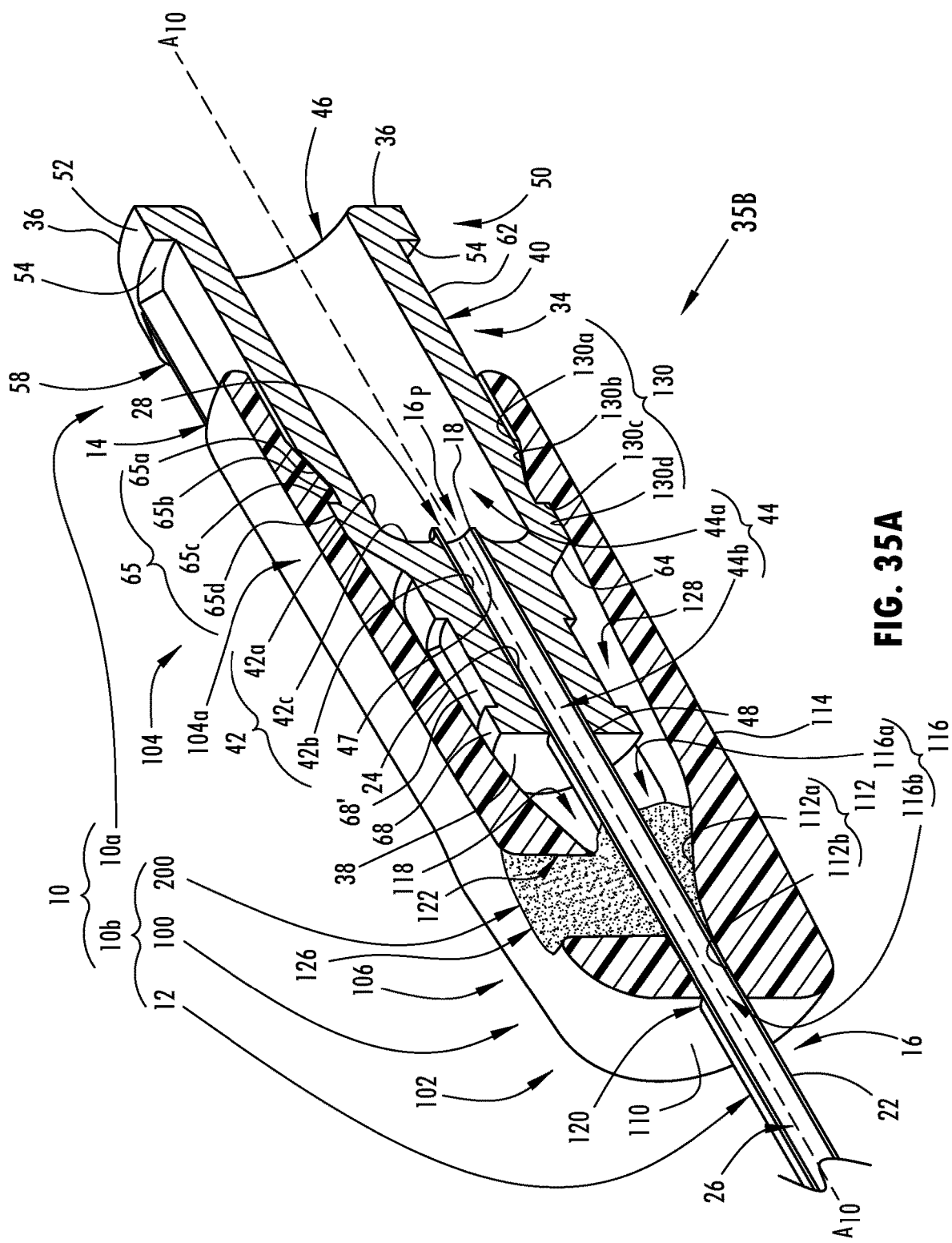
FIG. 35A is perspective cross-sectional view according to line 35-35 of the front perspective view of the hypodermic interface assembly of FIG. 34 that is arranged in an at-rest orientation.
Figure 35B:
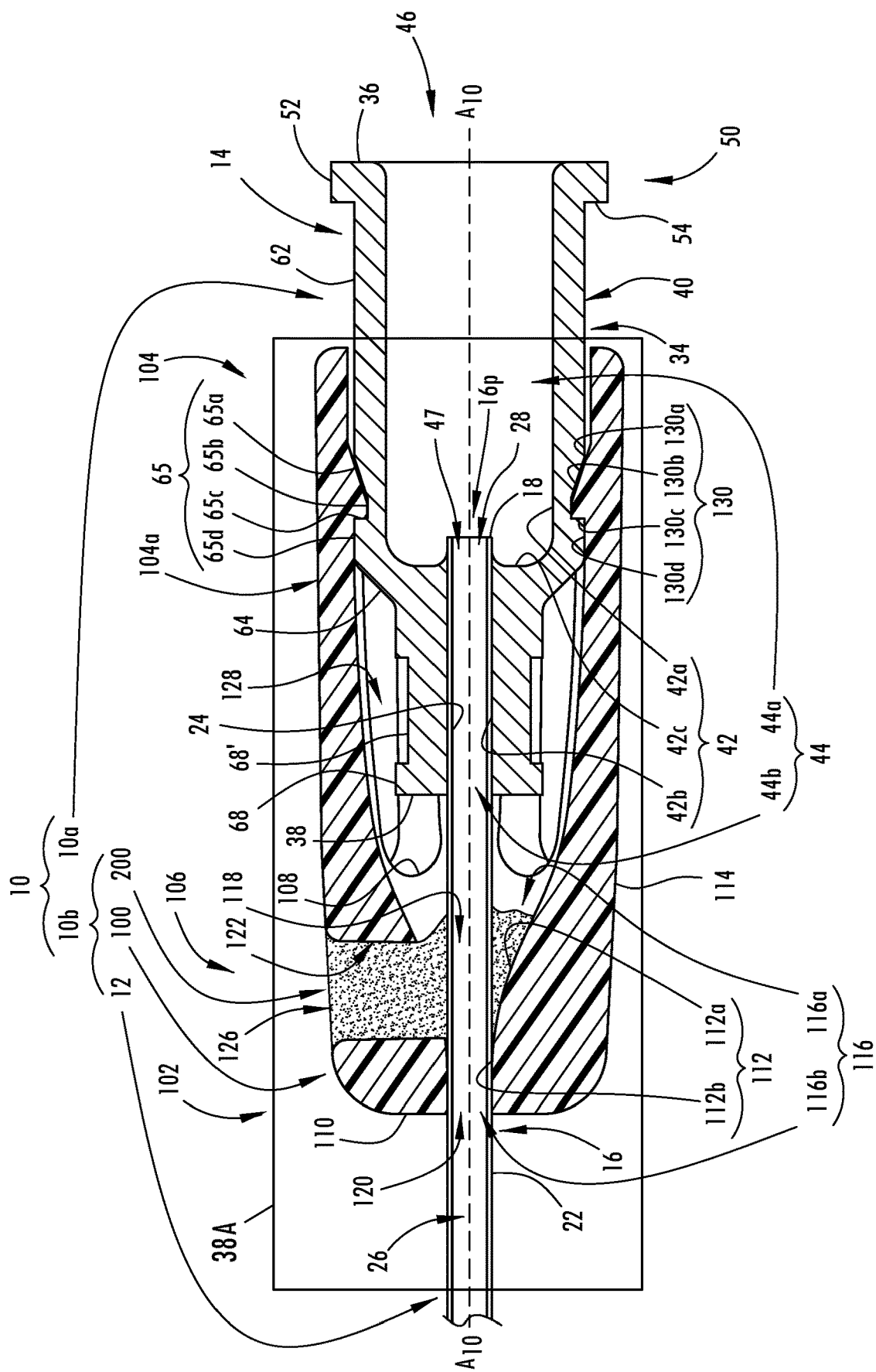
FIG. 35B is side cross-sectional view of the assembled hypodermic interface assembly according to arrow 35B of FIG. 35A.
Figure 36A:
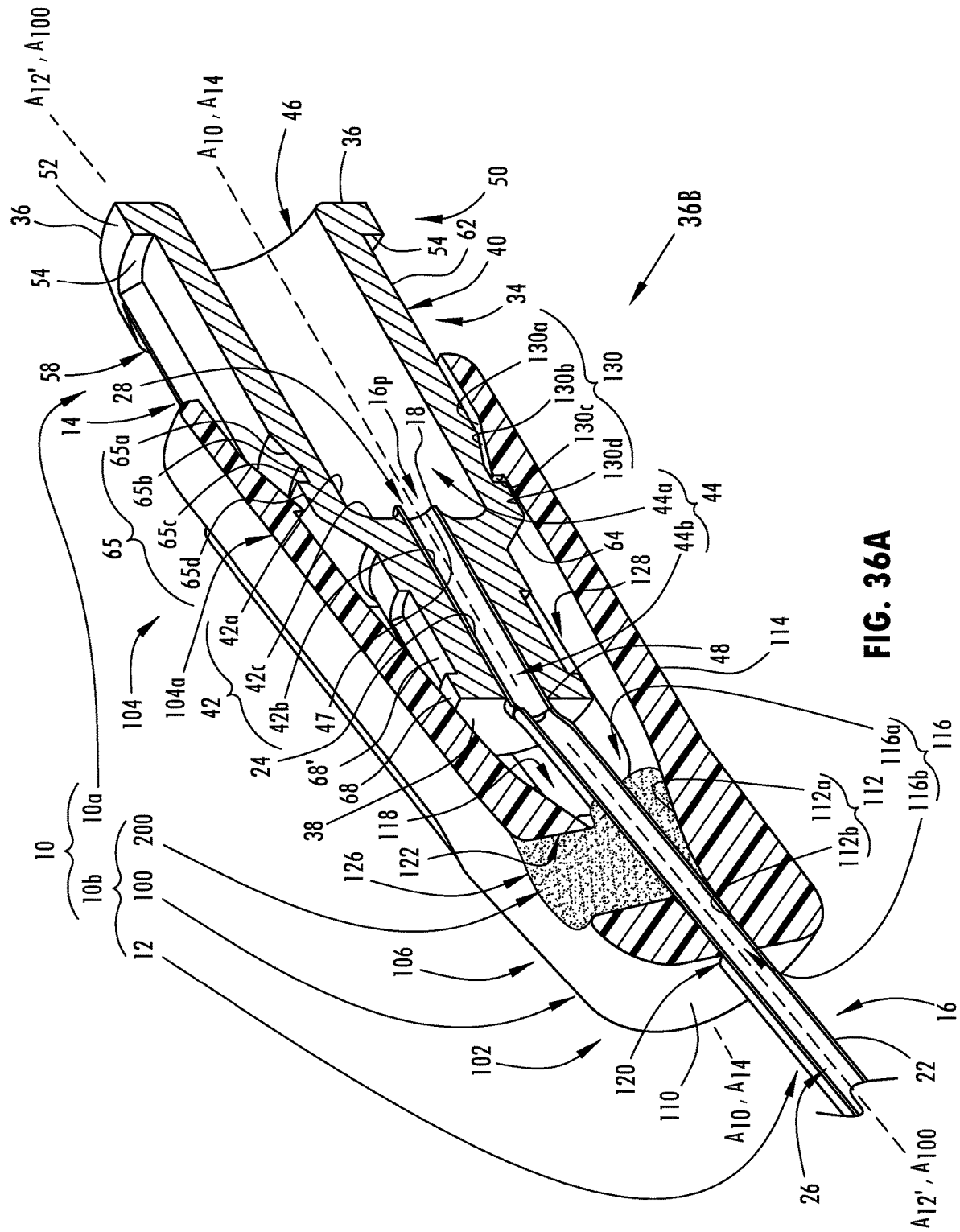
FIG. 36A is another perspective cross-sectional view according to the front perspective view of the hypodermic interface assembly of FIG. 35A that is arranged in a biased orientation.
Figure 36B:
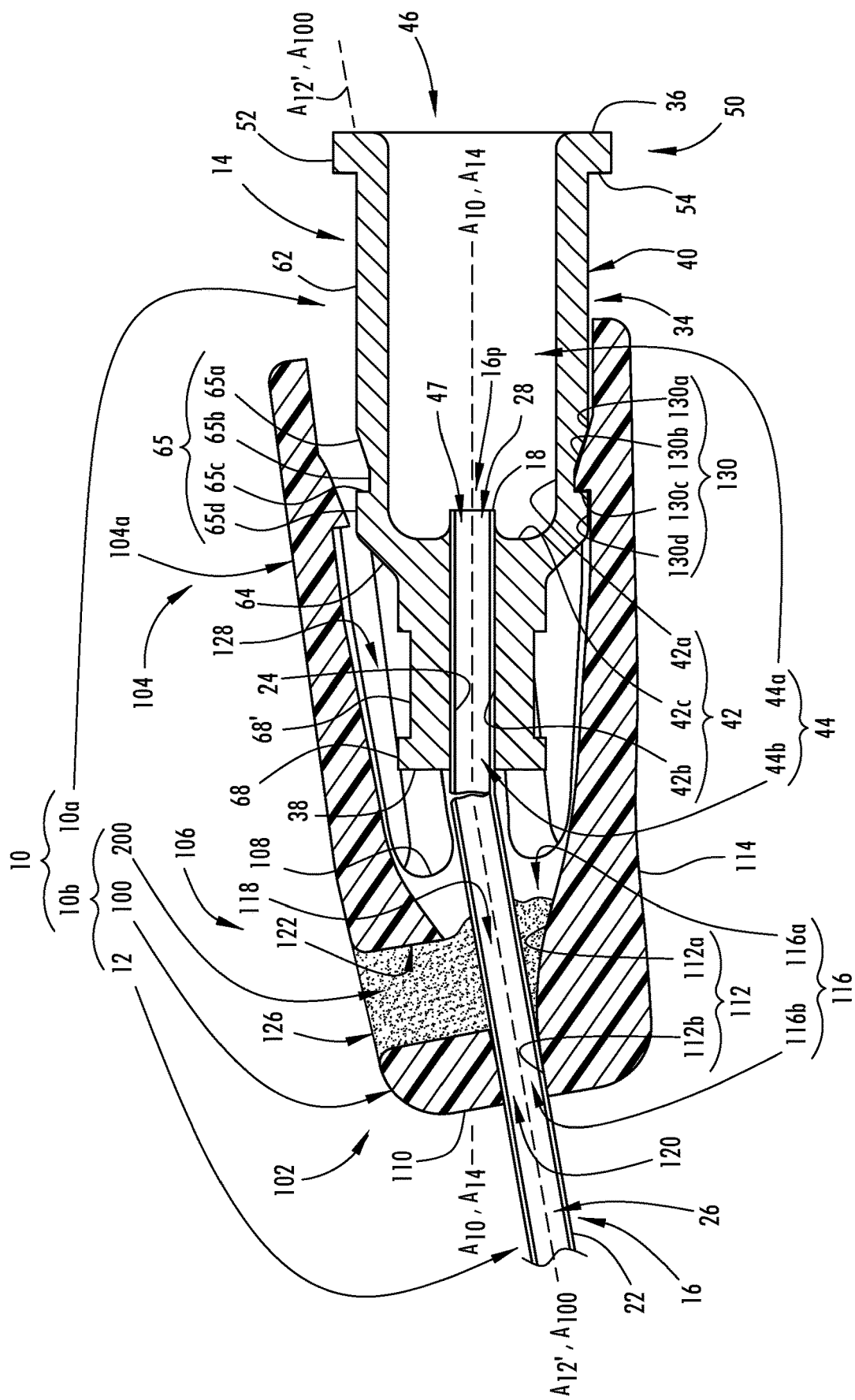
FIG. 36B is side cross-sectional view of the assembled hypodermic interface assembly according to arrow 36B of FIG. 36A.

Referring to FIGS. 34 and 35A-35B, the hypodermic interface assembly 10 is shown at an at-rest orientation. At FIGS. 36A-36B, the hypodermic interface assembly 10 is shown at a biased orientation. Thereafter, as seen at FIGS. 37A-37B, the hypodermic interface assembly 10 is shown arranged in a separated orientation defined by a first portion 10a of the hypodermic interface assembly 10 that is configured to remain attached to an injection gun I and a second portion 10b of the hypodermic interface assembly 10 that is configured to be removed from an impaled orientation within the flesh of the animalia S.

Figure 38B:
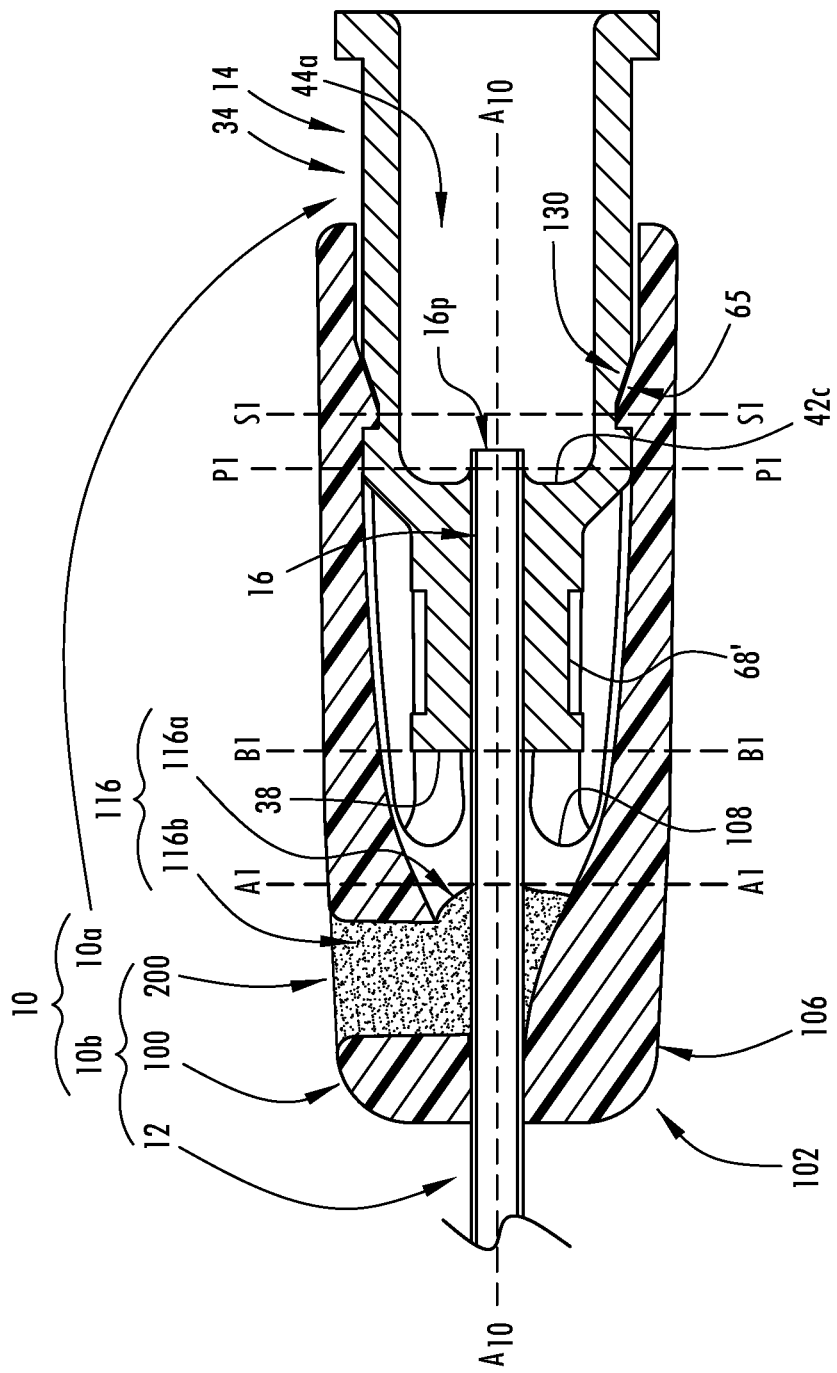
FIG. 38B is a cross-sectional side view of the assembled hypodermic interface assembly of FIG. 38A.

With reference to FIG. 38A, the third inner surface portion 42c of the inner surface 42 of the substantially tube-shaped body 34 of the hub 14 may define a curved or frustoconical surface that extends into the first passage portion 44a of the passage 44 of the hub 14. As seen at FIG. 38B, a peak of the curved or frustoconical surface defined by the third inner surface portion 42c of the inner surface 42 of the substantially tube-shaped body 34 is defined generally by a dashed line P1 that is orthogonal to the central axis $A_{10}$-$A_{10}$ of the hypodermic interface assembly 10. Furthermore, as also seen at FIG. 38B, another dashed line S1 that is orthogonal to the central axis $A_{10}$-$A_{10}$ of the hypodermic interface assembly 10 extends across the region where the proximal barb portion 130 of each leg portion 104a, 104b, 104c, 104d mechanically-joins the cannula carrier 100 to the circumferential notch or groove 65 formed by a portion of the outer body surface portion 62 of the outer surface 40 of the substantially tube-shaped body 34 of the hub 14. Yet even further, another dashed line B1 that is orthogonal to the central axis $A_{10}$-$A_{10}$ of the hypodermic interface assembly 10 extends across the distal end surface 38 of the hub 14. Further, yet another dashed line A1 that is orthogonal to the central axis $A_{10}$-$A_{10}$ of the hypodermic interface assembly 10 extends across a region of the head portion 102 of the cannula carrier 100 near the proximal end surface 108 of the body 106 of the head portion 102 of the cannula carrier 100.

The dashed line S1 generally demarcates a region of the hypodermic interface assembly 10 where the proximal barb portion 130 of each leg portion 104a, 104b, 104c, 104d of the cannula carrier 100 is configured to predictably mechanically separate from surface portions 65a, 65b, 65c, 65d that define the circumferential notch or groove 65 such that the cannula carrier 100 is permitted to mechanically separate from the hub 14. Furthermore, the dashed line B1 generally demarcates a region of the hypodermic interface assembly 10 where the cannula 12 may (but is not intended to) structurally fail and break into first and second portions. As such, a portion of the cannula 12 and the hub 14 that defines the first portion 10a of the hypodermic interface assembly 10 is configured to remain attached to the injection gun I. Similarly, the other portion of the cannula 12 that is non-removably-joined to the cannula carrier 100 by the adhesive 200 defines the second portion 10b of the hypodermic interface assembly 10 is configured to be removed from an impaled orientation within the flesh of the animalia S. Yet even further, the dashed line A1 generally demarcates a "fill line" where the amount of adhesive 200 should not further fill the first passage portion 116a or surround the cannula 12 in a region beyond the "fill line" A1. Furthermore, a distance extending between the "fill line" A1 and the dashed line B1 may be sized to permit the cannula 12 to in the region between the dashed lines A1 and B1 while not allowing the any surface portion of the needle carrier 100 to engage or come into contact with the distal end surface 38 of the hub 14.

Figure 37A:
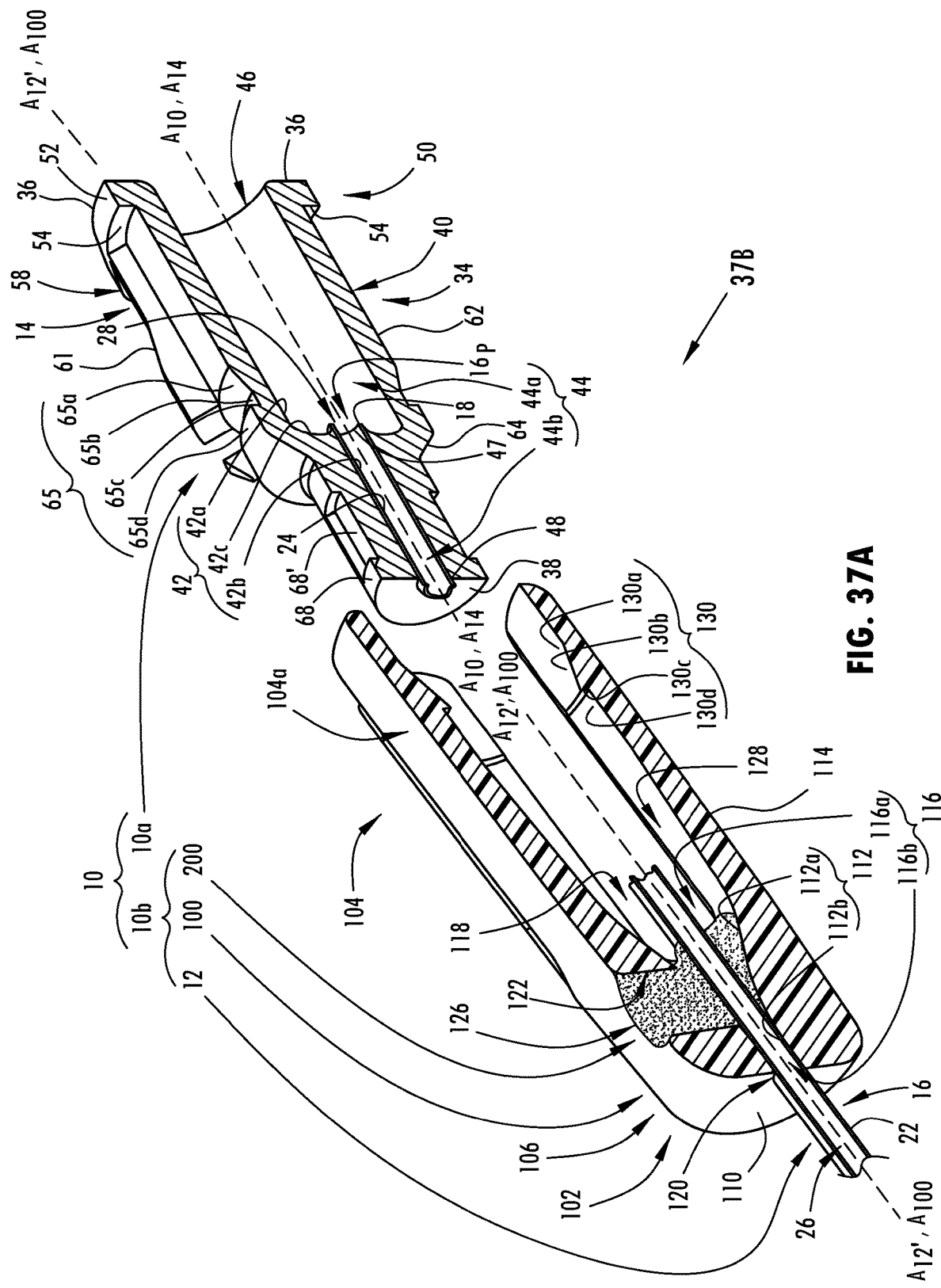
FIG. 37A is another perspective cross-sectional view according to the front perspective view of the hypodermic interface assembly of FIG. 35A that is arranged in a separated orientation.
Figure 37B:
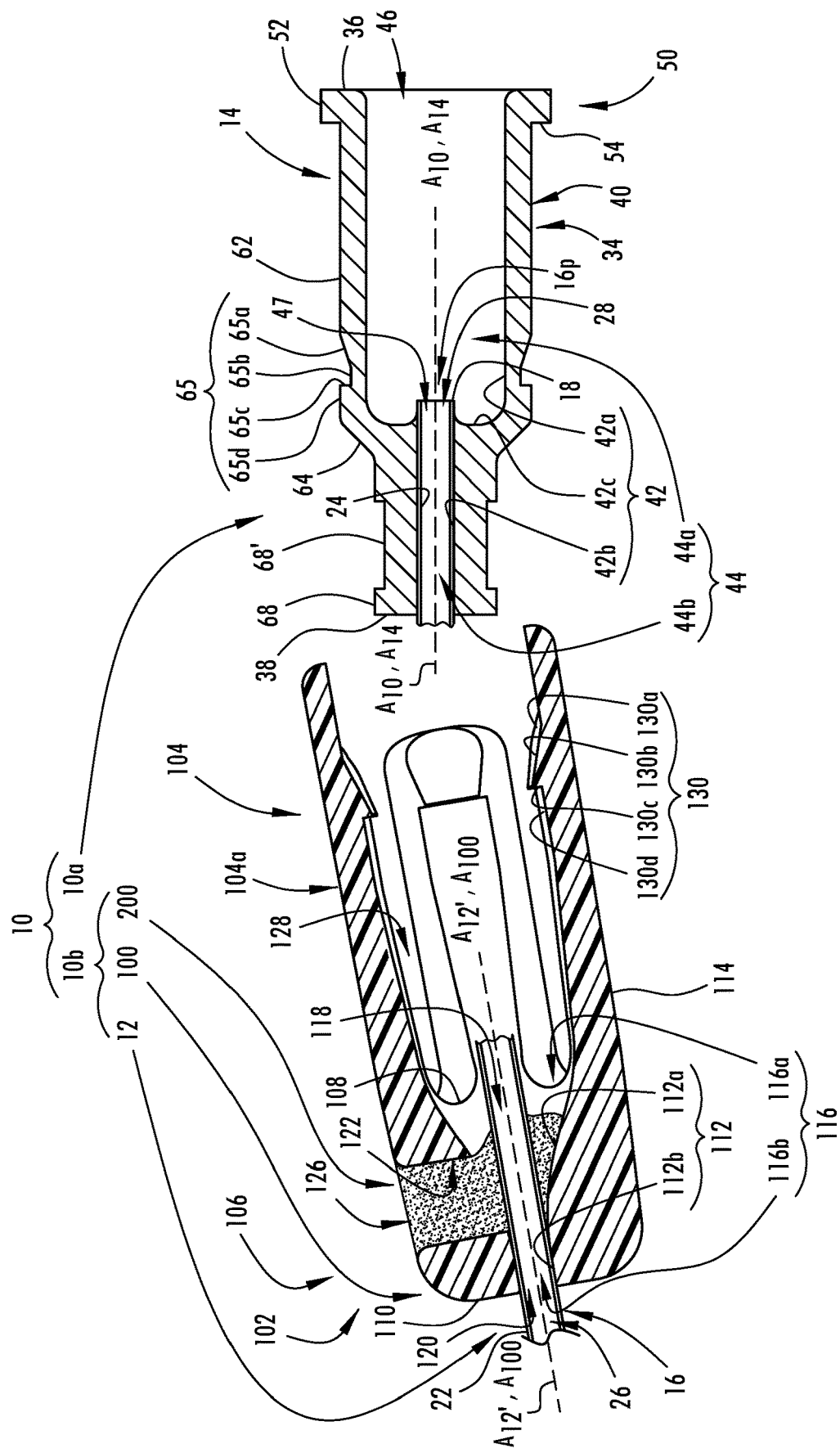
FIG. 37B is side cross-sectional view of the assembled hypodermic interface assembly according to arrow 37B of FIG. 37A.
Figure 38C:
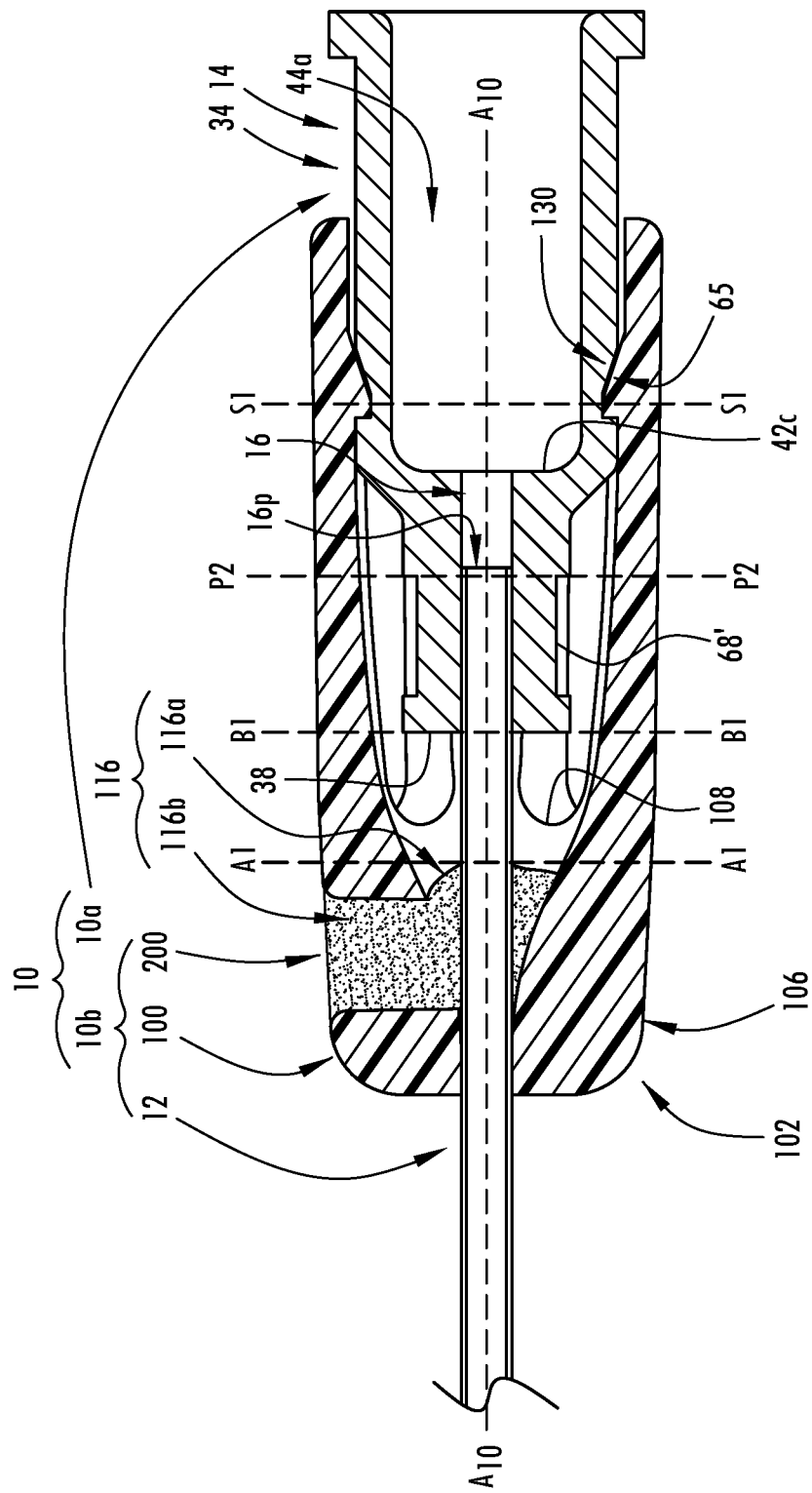
FIG. 38C is a cross-sectional side view of another assembled hypodermic interface assembly.

Although the structural integrity of the cannula 12 is shown to potentially (but is not intended to) fail in association with the exemplary implementation of the hypodermic interface assembly 10 as seen at FIGS. 37A-37B and 38A-38B, resulting in the cannula 12 breaking into first and second portions as seen at FIGS. 37A and 37B, with reference to FIGS. 38C and 39A-39C, the proximal end $16_P$ of the tube-shaped body 16 of the cannula 12 may be arranged within the hub 14 closer to the distal end surface 38 of the hub 14. Furthermore, as seen at FIG. 38C, the proximal end $16_P$ of the tube-shaped body 16 of the cannula 12 may be arranged proximal of a dashed line P2 that extends across a proximal-most end of the crimping pockets 68' defined by the outer head surface portion 68 of the outer surface 40 of the substantially tube-shaped body 34 of the hub 14. Although the proximal end $16_P$ of the tube-shaped body 16 of the cannula 12 is shown arranged proximal of the dashed line P2, the proximal end $16_P$ of the tube-shaped body 16 of the cannula 12 may be arranged anywhere between, for example the dashed line B1 and the dashed line P2.

Figure 38D:
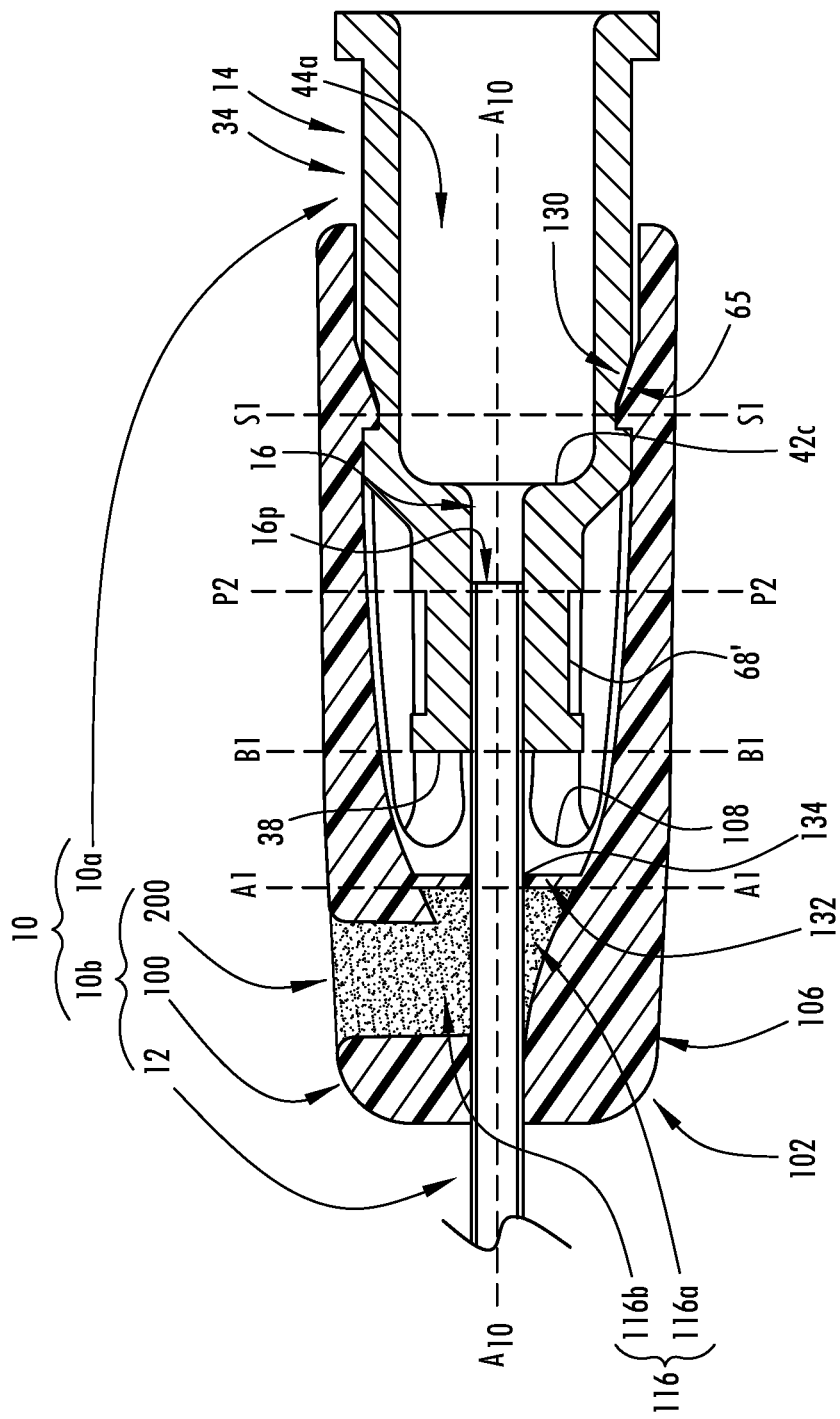
FIG. 38D is a cross-sectional side view of another assembled hypodermic interface assembly.

With reference to FIG. 38D, another exemplary configuration of the hypodermic interface assembly 10 is shown that is substantially similar to FIG. 38C with the exception that the body 106 of the head portion 102 of the cannula carrier 100 includes an adhesive blocking wall 132 including a cannula passage 134. The adhesive blocking wall 132 contains the adhesive 200 within at least a portion of the first passage portion 116a and prevents axial migration of the adhesive 200 in a direction further toward the dashed line B1 such that the adhesive 200 does not surround a portion of the cannula extending beyond the dashed line A1.

Figure 38E:
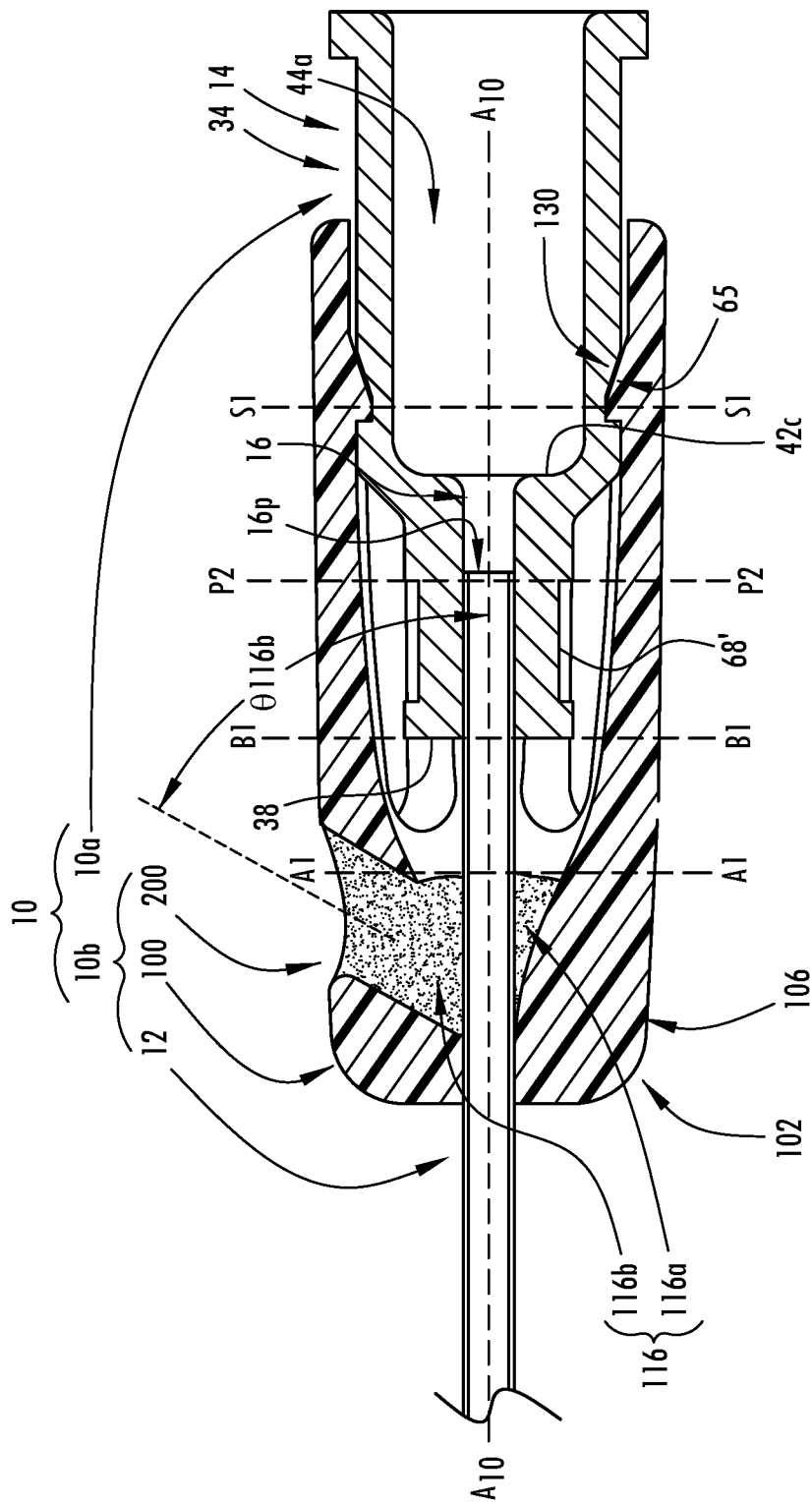
FIG. 38E is a cross-sectional side view of another assembled hypodermic interface assembly.

With reference to FIG. 38E, another exemplary configuration of the hypodermic interface assembly 10 is shown that is substantially similar to FIG. 38C with the exception that second passage portion 116b is arranged at an angle $\theta_{116b}$ that is not orthogonal to the central axis $A_{10}$-$A_{10}$. In an example, the angle $\theta_{116b}$ may be approximately equal to about 45° in order to assist in controlled depositing of the adhesive 200 into the first passage portion 116a such that the adhesive 200 substantially surrounds the cannula 12 up to and not beyond the fill line A1.

Figure 38F:
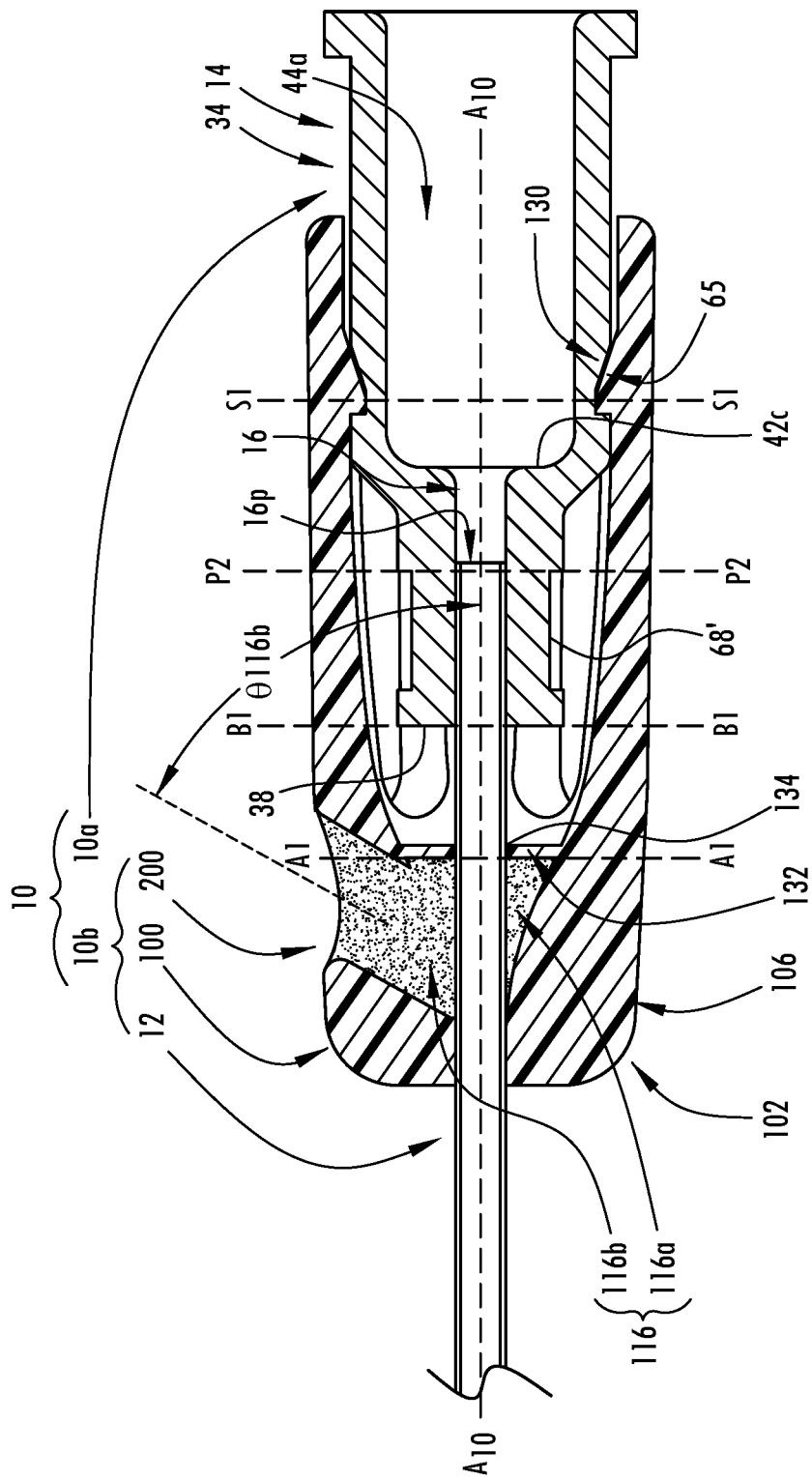
FIG. 38F is a cross-sectional side view of another assembled hypodermic interface assembly.

With reference to FIG. 38F, another exemplary configuration of the hypodermic interface assembly 10 is shown that is substantially similar to FIG. 38E with the exception that the body 106 of the head portion 102 of the cannula carrier 100 includes the adhesive blocking wall 132 including a cannula passage 134. The adhesive blocking wall 132 contains the adhesive 200 within at least a portion of the first passage portion 116a and prevents axial migration of the adhesive 200 in a direction further toward the dashed line B1 such that the adhesive 200 does not surround a portion of the cannula extending beyond the dashed line A1. Such an arrangement seen at FIGS. 38C and 39A results in the proximal end $16_P$ of the tube-shaped body 16 of the cannula 12 being "ripped" out of, or, alternatively, being "migrated away from" (as seen at FIGS. 39B and 39C) the first portion 10a of the hypodermic interface assembly 10 while the entire tube-shaped body 16 of the cannula 12 remains joined to the second portion 10b of the hypodermic interface assembly 10. Accordingly, as seen at FIG. 39C, all of the cannula 12 remains structurally intact and does not break into first and second portions as seen at FIGS. 37A and 37B (and, as a result, does not define a 'break line').

Referring now to FIGS. 40 and 41A-41G, a methodology for utilizing any configuration of the exemplary hypodermic interface assemblies 10 is shown. Although FIGS. 40 and 41A-41G show a methodology for utilizing the hypodermic interface assembly 10 described at FIGS. 33-35B, any of the other hypodermic interface assemblies described in the present disclosure may also be utilized in a substantially similar manner as seen at FIGS. 40 and 41A-41G.

As described above, the design of the hypodermic interface assembly 10 promotes controlled separation (see, e.g., FIGS. 37A-37B, 39A-39C and 41E) of the cannula 12, the cannula carrier 100, and the adhesive 200 (that collectively define the second portion 10b of the hypodermic interface assembly 10) relative to the hub 14 (that defines the first portion 10a of the hypodermic interface assembly 10).

Figure 41A:
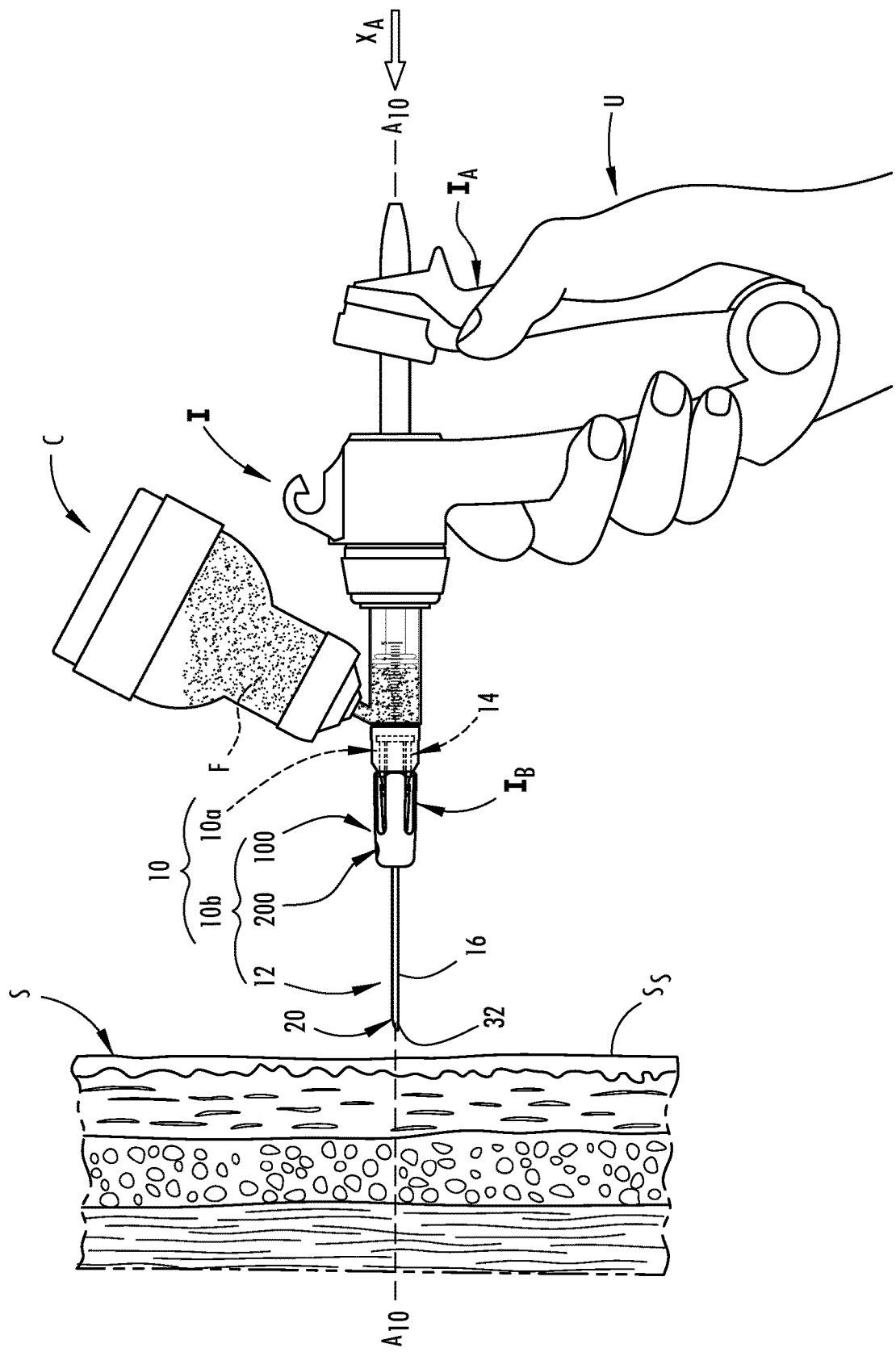
FIG. 41A is a side view of the hypodermic interface assembly and a cross-sectional view of a portion of the animalia of FIG. 40 arranged in a spaced-apart relationship.
Figure 41B:
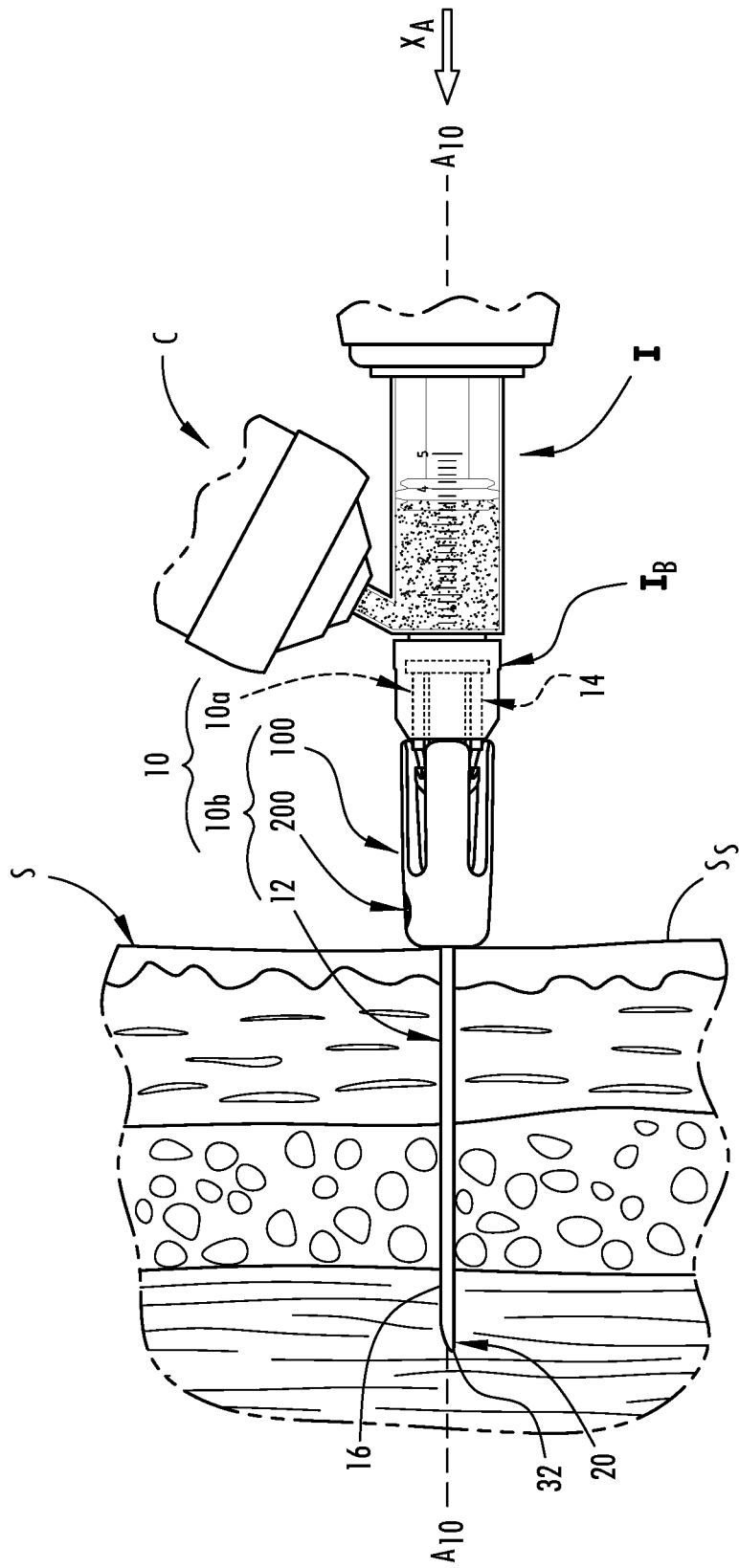
FIG. 41B is another side view of the hypodermic interface assembly and another cross-sectional view of a portion of the animalia according to FIG. 41A arranged in a pierced relationship.

In some instances, predictable and controlled separation of the second portion 10b of the hypodermic interface assembly 10 from the first portion 10a of the hypodermic interface assembly 10 may occur after the cannula 12 pierces the subject S (see, e.g., FIGS. 41A-41B). The subject S may be, for example, animalia, such as a human or non-human (i.e., an animal such as, for example, pig or swine). In other examples, the subject S may be an inanimate object. The predicable and controlled separation of the second portion 10b of the hypodermic interface assembly 10 from the first portion 10a of the hypodermic interface assembly 10 mitigates separation of the cannula 12 from the entirety of the hub 14, which may otherwise undesirably result in the cannula 12 being broken-off and subsequently lost (or make difficult easily locating the broken-off cannula) within the flesh of the animalia.

Figure 40:
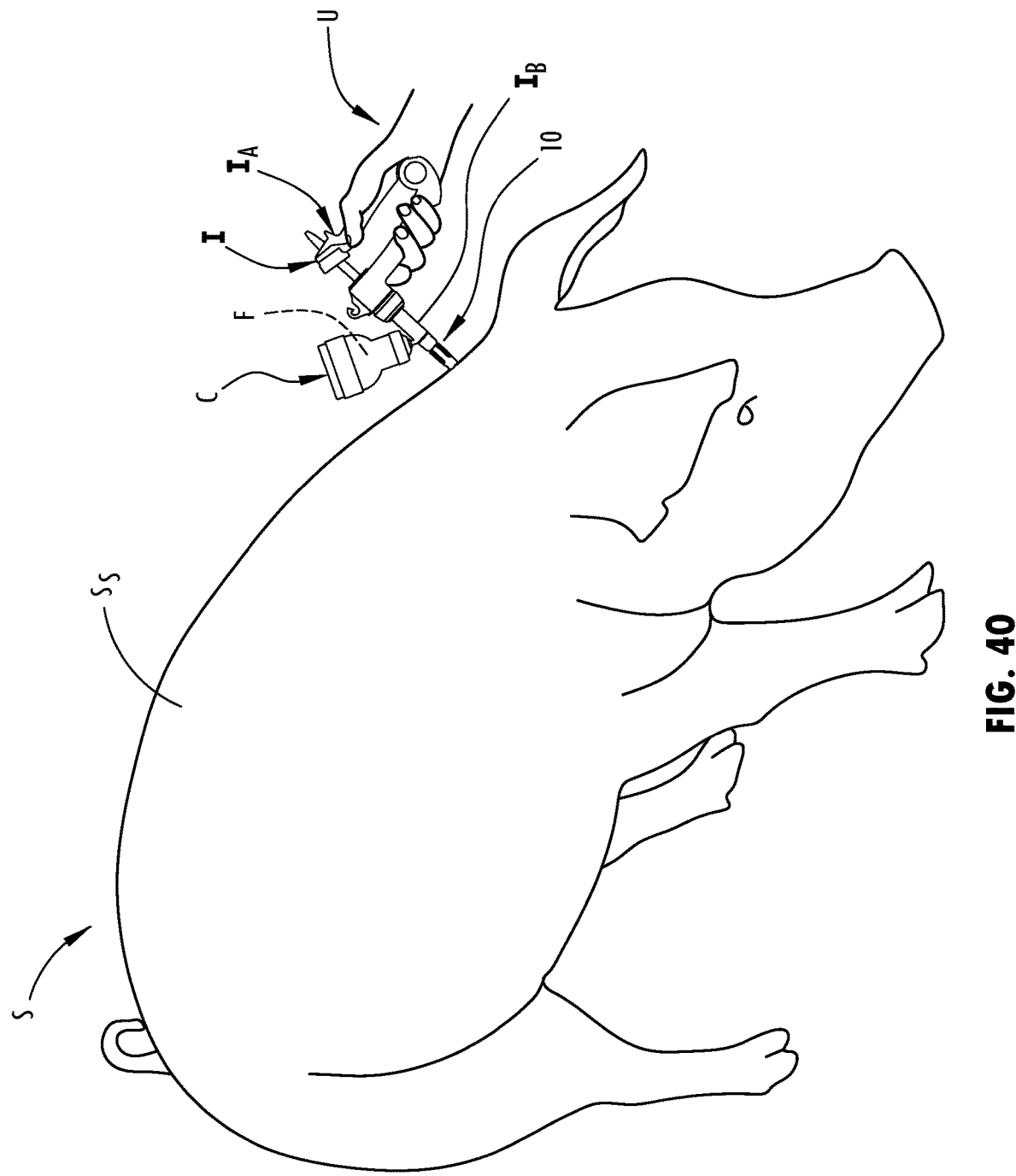
FIG. 40 is a view of a hypodermic interface assembly arranged proximate animalia.

Referring to FIG. 40, the hypodermic interface assembly 10 is shown connected to an injecting device I, such as, for example, an injection gun. The hypodermic interface assembly 10 may be connected to a barrel portion $I_B$ of the injection gun I by arranging, for example, the first radially-outward projection or ear 56 and the second radially-outward projection or ear 58 extending from the of the barrel-engaging portion 50 that extends from the outer surface 40 of the substantially tube-shaped body 34 of the hub 14 in corresponding recesses (not shown) formed by the barrel portion $I_B$ of the injection gun I and then, for example, quarter-turn locking the hypodermic interface assembly 10 for removably-securing the first radially-outward projection or ear 56 and the second radially-outward projection or ear 58 extending from the of the barrel-engaging portion 50 to the barrel portion $I_B$ of the injection gun I.

Figure 41C:
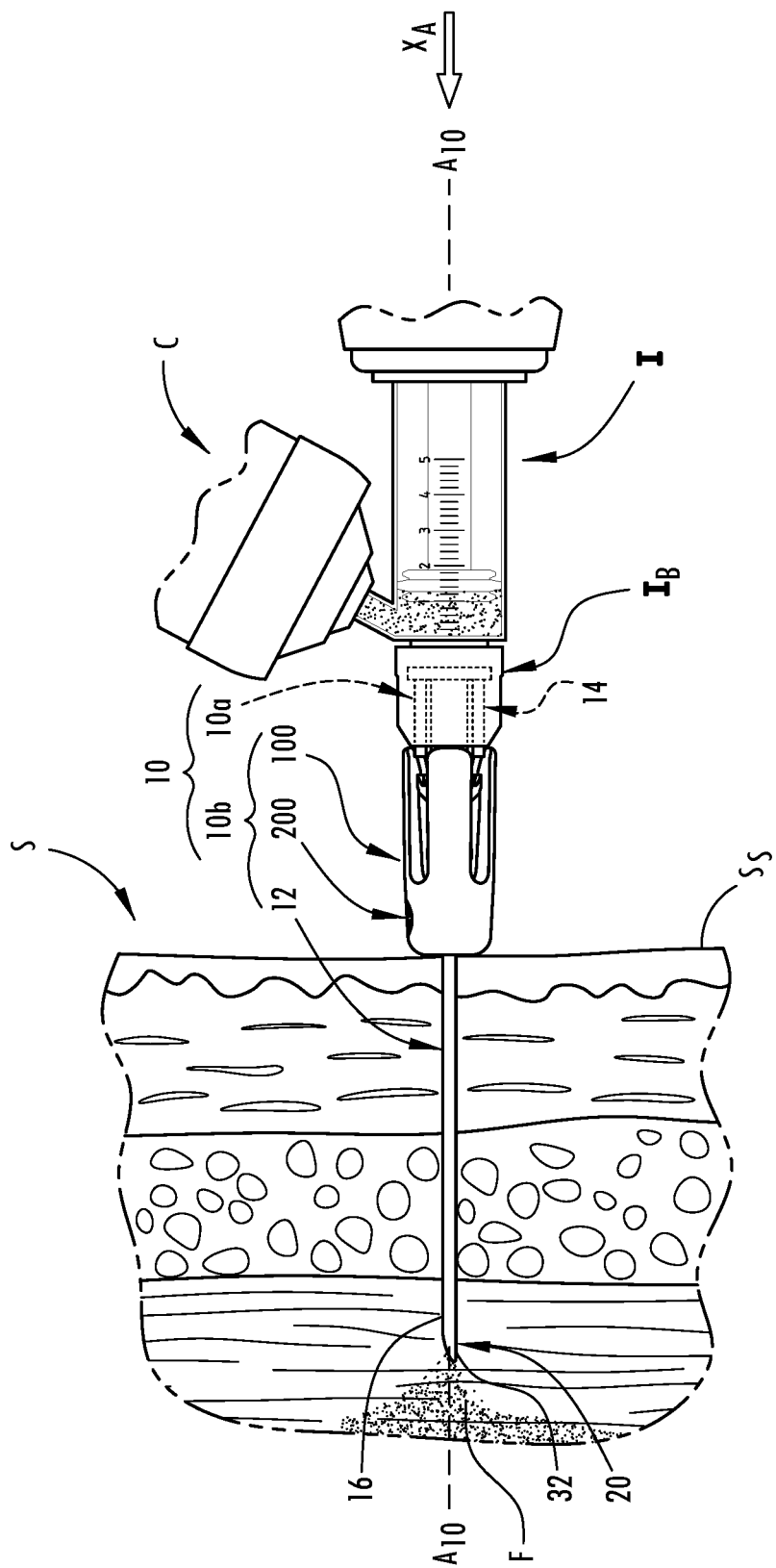
FIG. 41C is another side view of the hypodermic interface assembly and another cross-sectional view of a portion of the animalia according to FIG. 41B arranged in a pierced relationship while, optionally, the hypodermic interface assembly is utilized for injecting a fluid into the animalia.

The injection gun I may include a fluid container C that contains a fluid F (see also, e.g., FIG. 41C). The fluid F may be metered from: (1) the container C; (2) through the injection gun I; (3) into the hypodermic interface assembly 10; and (4) out of the hypodermic interface assembly 10 and into the flesh of the subject S. The injection gun I may be actuated when a user U presses, for example, an actuator IA such as, for example, a trigger in order to cause movement of the fluid F as described above. The injection gun I may be powered in any desirable manner such as, for example: battery powered; air powered; manually powered; or a combination thereof.

Referring to FIG. 41A, the user may grasp the injection gun I and position the sharp piercing tip 32 formed by the distal end surface 20 of the tube-shaped body 16 of the cannula 12 near the outer surface $S_S$ of the subject S, which may define the skin or hide of the subject S. Referring to FIGS. 41A-41B, the user U may impart an axial force according to the direction of the arrow $X_A$ to the injection gun I along the central axis $A_{10}$-$A_{10}$ extending through the hypodermic interface assembly 10 such that the sharp piercing tip 32 formed by the distal end surface 20 of the tube-shaped body 16 of the cannula 12 axially pierces the outer surface $S_S$ of the subject S.

Referring to FIGS. 38A and 41C, after the outer surface $S_S$ of the subject S has been axially pierced by the cannula 12, the user U may optionally actuate the actuator IA in order to cause movement of the fluid F from: (1) the container C; (2) through the injection gun I; (3) into the hypodermic interface assembly 10; and (4) out of the hypodermic interface assembly 10 and into the flesh of the subject S. In an example, the fluid F may firstly enter the hypodermic interface assembly 10 from the injection gun I at the passage 44 formed by the substantially tube-shaped body 34 of the hub 14 by way of the proximal opening 46 formed by the proximal end surface 36 of the substantially tube-shaped body 34 of the hub 14. Then, the fluid F may secondly enter the passage 26 extending through the tube-shaped body 16 of the cannula 12 by way of the proximal opening 28 formed by the proximal end surface 18 of the body 16 of the cannula 12. Then, thirdly, the fluid F may exit the passage 44 formed by the substantially tube-shaped body 34 of the hub 14 by way of the distal opening 48 formed by the distal end surface 38 of the substantially tube-shaped body 34 of the hub 14. Thereafter, fourthly, the fluid F may exit the passage 26 extending through the tube-shaped body 16 of the cannula 12 by way of the distal opening 30 formed by the distal end surface 20 of the body 16 of the cannula 12.

The fluid F may be any desirable composition that is intended to be delivered to the animalia S. In some instances, the fluid F may be a medicament, a pharmaceutical, a vaccine, an anesthetic, or the like. Accordingly, the fluid F may not include any type of fluid that is not intended to be injected into animalia S. Although the hypodermic interface assembly 10 also may be utilized for injecting fluid F into animalia S, the hypodermic interface assembly 10 may be utilized for removing fluid F (e.g., blood) from animalia S. Therefore, it will be appreciated that the hypodermic interface assembly 10 may deliver or receive fluid F.

Referring to FIGS. 36A-36B, 39B, and 41D, after the outer surface $S_S$ of the subject S has been axially pierced by the cannula 12, the subject S may experience discomfort as a result of pain arising from the outer surface $S_S$ being pierced by the sharp piercing tip 32 formed by the distal end surface 20 of the tube-shaped body 16 of the cannula 12. Accordingly, if the user U is sufficiently grasping the injection gun I, any movement of the subject S may result in the cannula 12 being subjected to one or more radial forces $X_R$ relative the central axis $A_{10}$-$A_{10}$ extending through the hypodermic interface assembly 10 that may cause the cannula 12 to bend or warp, such that the central axis $A_{12}$-$A_{12}$ extending through the axial center of the tube-shaped body 16 of the cannula 12 is not coincident with the central axis $A_{10}$-$A_{10}$ extending through the hypodermic interface assembly 10 that may be coaxially aligned with the other components of the hypodermic interface assembly 10 such as, for example, the hub 14 and the cannula carrier 100.

Because the cannula carrier 100 may be formed from a flexible or substantially non-rigid material (e.g., plastic), any stresses imparted to the cannula 12 arising from the one or more radial forces $X_R$ may be transmitted from the cannula 12 to the cannula carrier 100; and any such stresses transmitted from the cannula 12 to the cannula carrier 100 may be directed to and concentrated at a predetermined portion or region of the hypodermic interface assembly 10. The predetermined portion or region of the hypodermic interface assembly 10 that receives the concentrated stresses is generally defined by a portion or region of the hypodermic interface assembly 10 where the separation line (see, e.g., the dashed line S1 of FIGS. 38B, 38C, which may be referred to as a separation line) traverses the cannula carrier 100 and the hub 14 of the hypodermic interface assembly 10. As described above, the separation line S1 generally demarcates the regions with the cannula carrier 100 being capable of mechanically separating from the hub 14. Also, depending on the inset orientation of the cannula 12 relative the hub 14, the cannula 12 may remain intact, unbroken (as seen at, e.g., FIG. 39C), or, in some configurations, the cannula 12 may (but is not intended to) structurally fail and break (as seen at, e.g., FIG. 37A and according to the break line B1 of FIG. 38B) as a result of a stress concentration arising from the one or more radial forces $X_R$ that also may be transmitted to the cannula 12 and concentrated at, substantially at, about, along, or on the region of the hypodermic interface assembly 10 defined by the break line B1. And in either implementation, the distal portion of the cannula 12 remains non-removably connected to the cannula carrier 100 by way of, for example, the adhesive 200.

As seen at FIG. 38A, the cannula carrier 100 may be defined by a length $L_{100}$ that is further defined by sub-lengths $L_{100a}$ and $L_{100b}$. The sub-length $L_{100b}$ may be further defined by sub-length portions $L_{100b1}$ and $L_{100b2}$.

The sub-length $L_{100a}$ may be defined by a length of the head portion 102 of the cannula carrier 100. The sub-length $L_{100b}$ may be defined by a length of each leg portion 104a, 104b, 104c, 104d of the cannula carrier 100. The sub-length portion $L_{100b1}$ may be defined by a length of each leg portion 104a, 104b, 104c, 104d not including the proximal barb portion 130 of each leg portion 104a, 104b, 104c, 104d. The sub-length portion $L_{100b2}$ may be defined by a length of each proximal barb portion 130 of each leg portion 104a, 104b, 104c, 104d.

Each length portion $L_{100a}$ and $L_{100b}$ and each sub-length portions $L_{100b1}$ and $L_{100b2}$ may be selectively distanced or configured in order to optimize mechanical separation of the cannula carrier 100 from the hub 14 at the separation line S1. For example, sufficient leg length (e.g., as defined by the sub-length portion $L_{100b2}$) may assist in allowing each leg portion 104a, 104b, 104c, 104d of the cannula carrier 100 to separate from the hub 14 at the separation line S1 without the body 106 of cannula carrier 100 interfering with the distal end surface 38 of the hub 14 when the one or more radial forces $X_R$ is/are applied to the cannula 12. Furthermore, a combination of the selective distancing or configuration of the length portions $L_{100a}$ and $L_{100b}$ and each sub-length portions $L_{100b1}$ and $L_{100b2}$ in combination with providing a UV adhesive for the adhesive portion 200 may strengthen the overall hypodermic interface assembly 10.

Figure 41D:
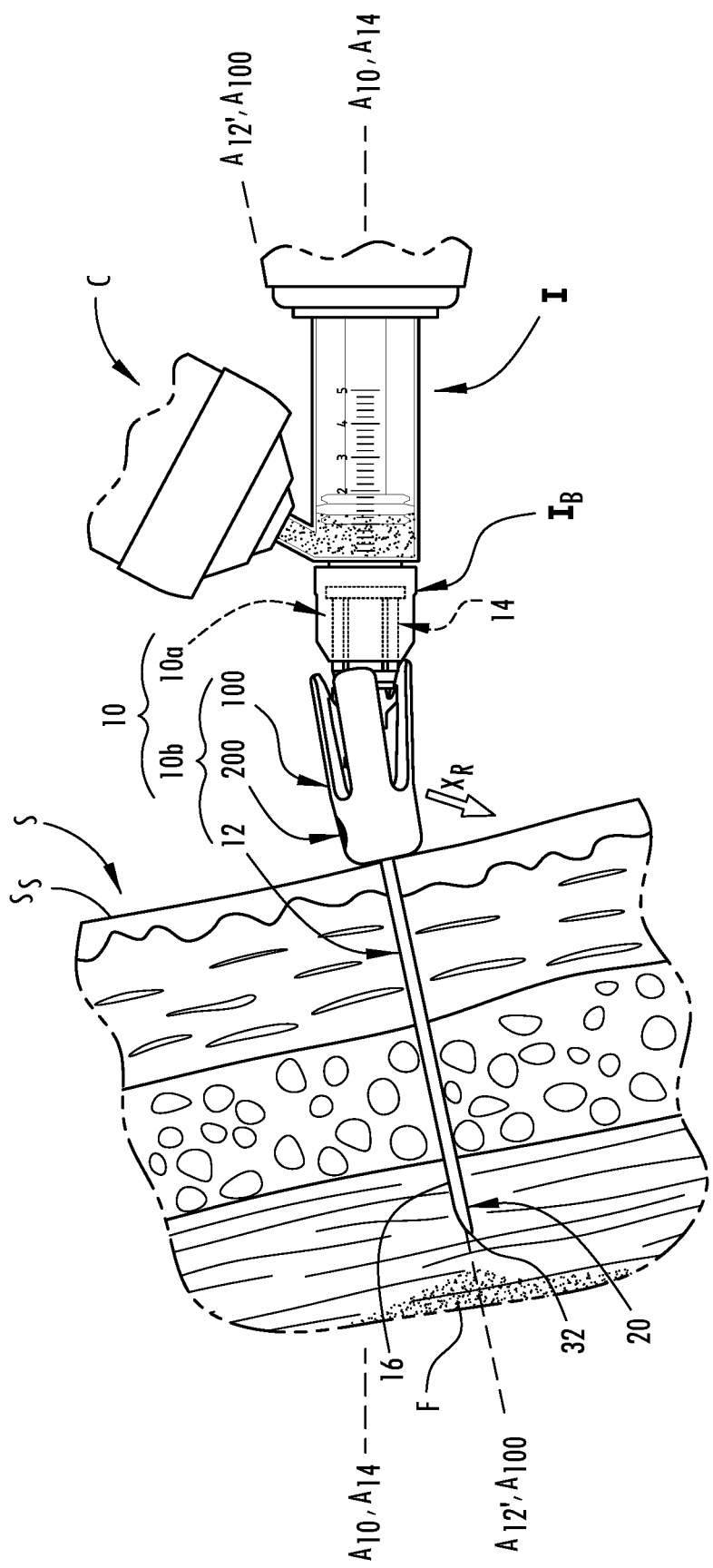
FIG. 41D is another side view of the hypodermic interface assembly and another cross-sectional view of a portion of the animalia according to FIG. 41B arranged in a pierced-and-torqued relationship.

As seen at FIG. 41D, as a result of stresses transmitted from the cannula 12 to the hub 14 being directed to and concentrated at a predetermined portion or region of the cannula carrier 100 and the hub 14, the cannula carrier 100 may be permitted to also bend or deviate with the cannula 12 away from the central axis $A_{10}$-$A_{10}$ extending through the hypodermic interface assembly 10 (see, e.g., the axes $A_{12}$-$A_{12}$, $A_{100}$-$A_{100}$ of the cannula 12 and the cannula carrier 100). Accordingly, the axes $A_{12}$-$A_{12}$, $A_{100}$-$A_{100}$ of the cannula 12 and the cannula carrier 100 generally deviate away from the axis $A_{14}$-$A_{14}$ of the hub 14, which may remain coincident with the central axis $A_{10}$-$A_{10}$ extending through the hypodermic interface assembly 10.

Figure 41E:
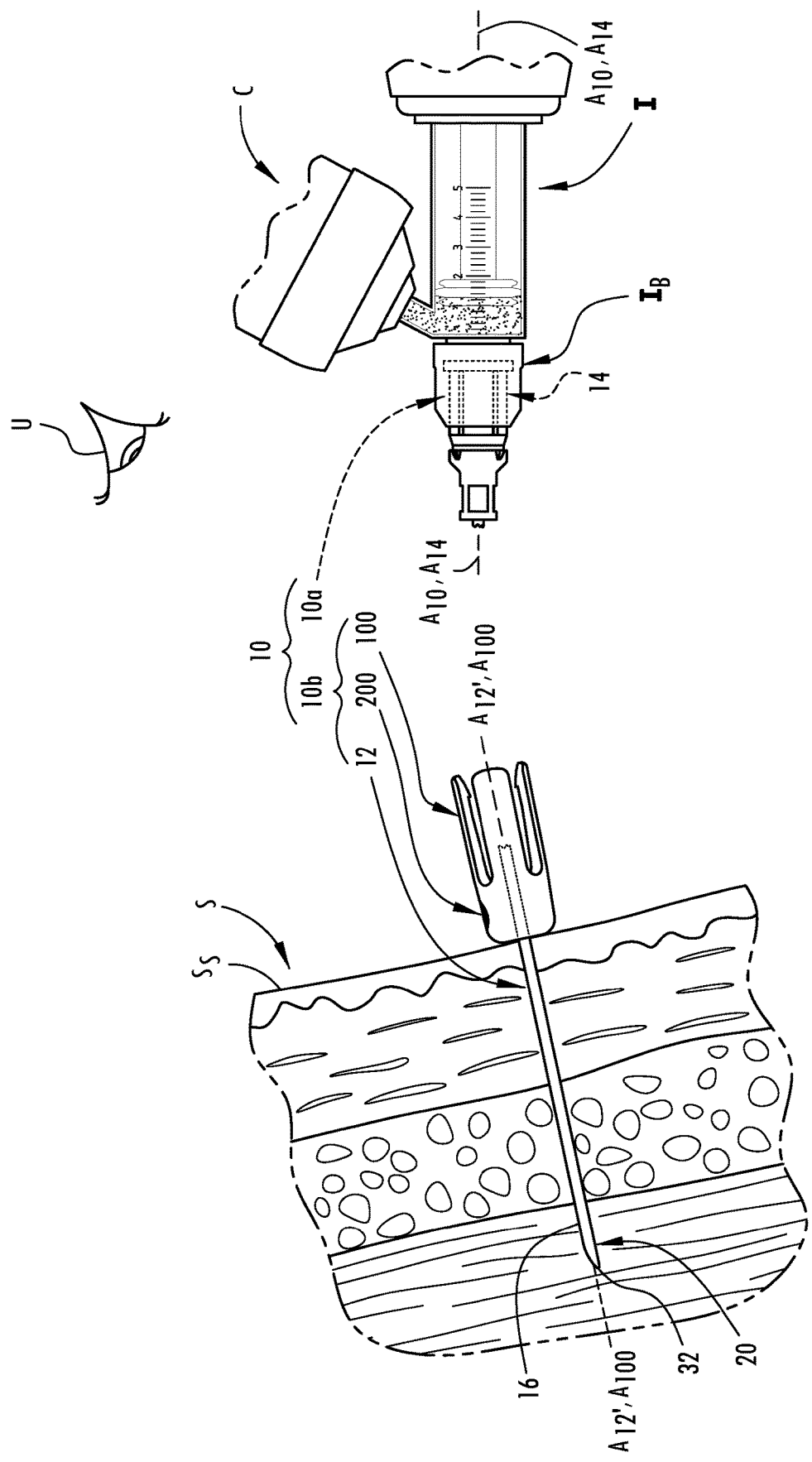
FIG. 41E is another side view of the hypodermic interface assembly and another cross-sectional view of a portion of the animalia according to FIG. 41D arranged in a separated-after-pierced relationship defining a first portion of the hypodermic interface assembly attached to an injection gun and a second portion of the hypodermic interface assembly impaled within flesh of the animalia.

Referring to FIGS. 37A-37B and 41E, the stresses transmitted from the cannula 12 to the interface assembly (10) that were directed to and concentrated at the predetermined portion or region (e.g., at separation line S1) may continue to bend the cannula carrier 100 relative the hub 14 until the cannula carrier 100 controllably mechanically separates from the hub 14 by flexibly-disconnecting the proximal barb portion 130 of each leg portion 104a, 104b, 104c, 104d of the cannula carrier 100 from surface portions 65a, 65b, 65c, 65d that define the circumferential notch or groove 65 such that the cannula carrier 100 is permitted to mechanically separate from the hub 14. As a result, the second portion 10b of the hypodermic interface assembly 10 including the cannula carrier 100, the cannula 12, and the adhesive 200 predictably and controllably separates from the first portion 10a of the hypodermic interface assembly 10 defined by the hub 14 (at, or substantially at, about, along, or on break line B1). After separation, each leg portion 104a, 104b, 104c, 104d of the cannula carrier 100 may deform, expand, or splay outwardly, which may increase visibility to a user to assist in locating where the cannula 12 is impaled within the flesh of the animalia S.

As seen at FIG. 41E, because the cannula carrier 100 is non-separably joined to the cannula 12 with the adhesive 200, the user U, may easily identify a location of the animalia S where the cannula 12 is impaled within the flesh of the animalia S. The location of the animalia S where the cannula 12 is impaled within the flesh of the animalia S is easily identifiable as a result of, for example, the cannula carrier 100 of the second portion 10b of the hypodermic interface assembly 10 resting upon the skin $S_S$ or hide of the animalia S (while the cannula 12 is not visible to the user U since the cannula 12 is contained within and obscured by the flesh of the animalia S.

Figure 41F:
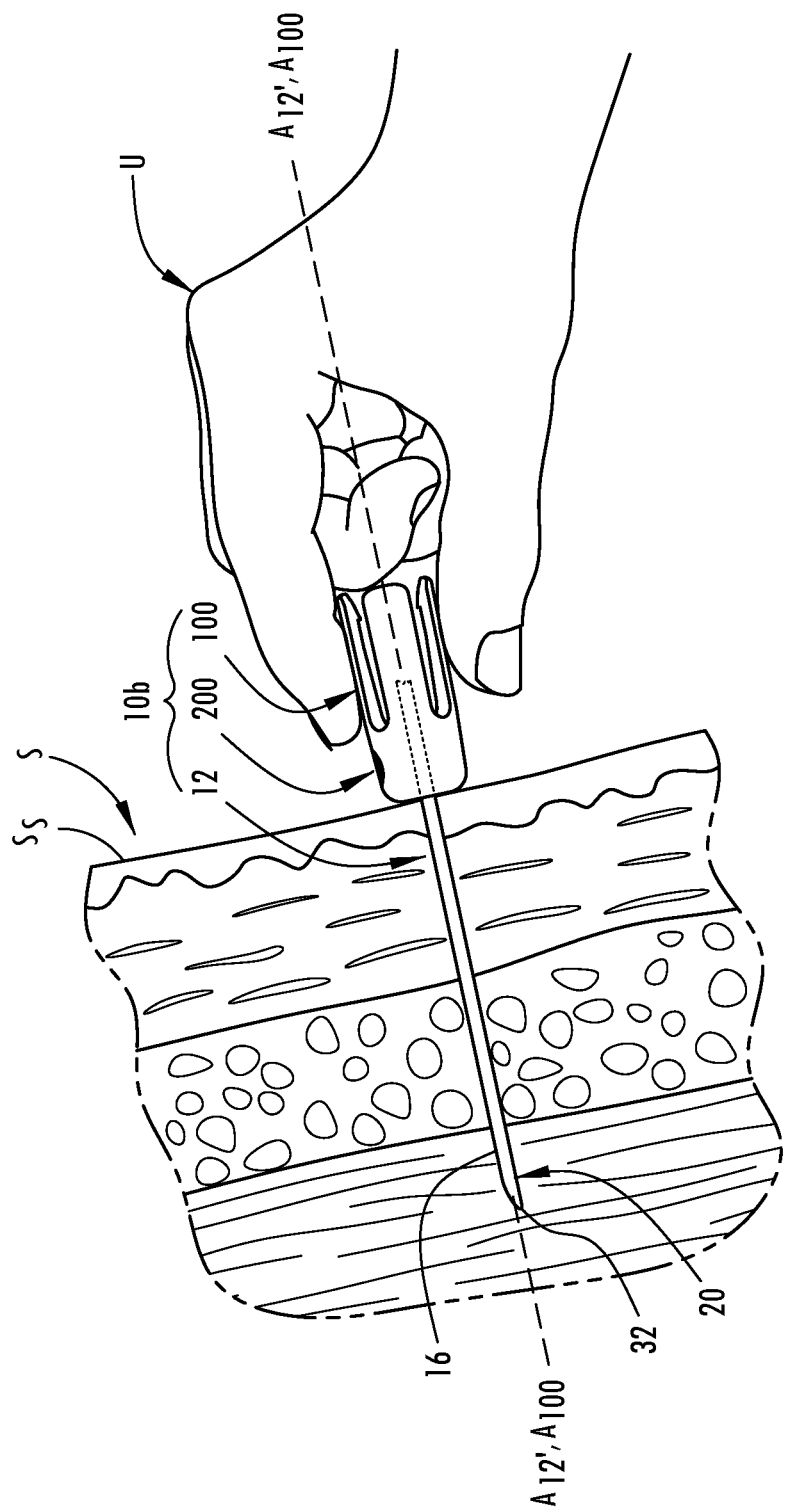
FIG. 41F is another side view of the according to FIG. 41E illustrating a user grasping the second portion of the hypodermic interface assembly that is impaled within flesh of the animalia.
Figure 41G:
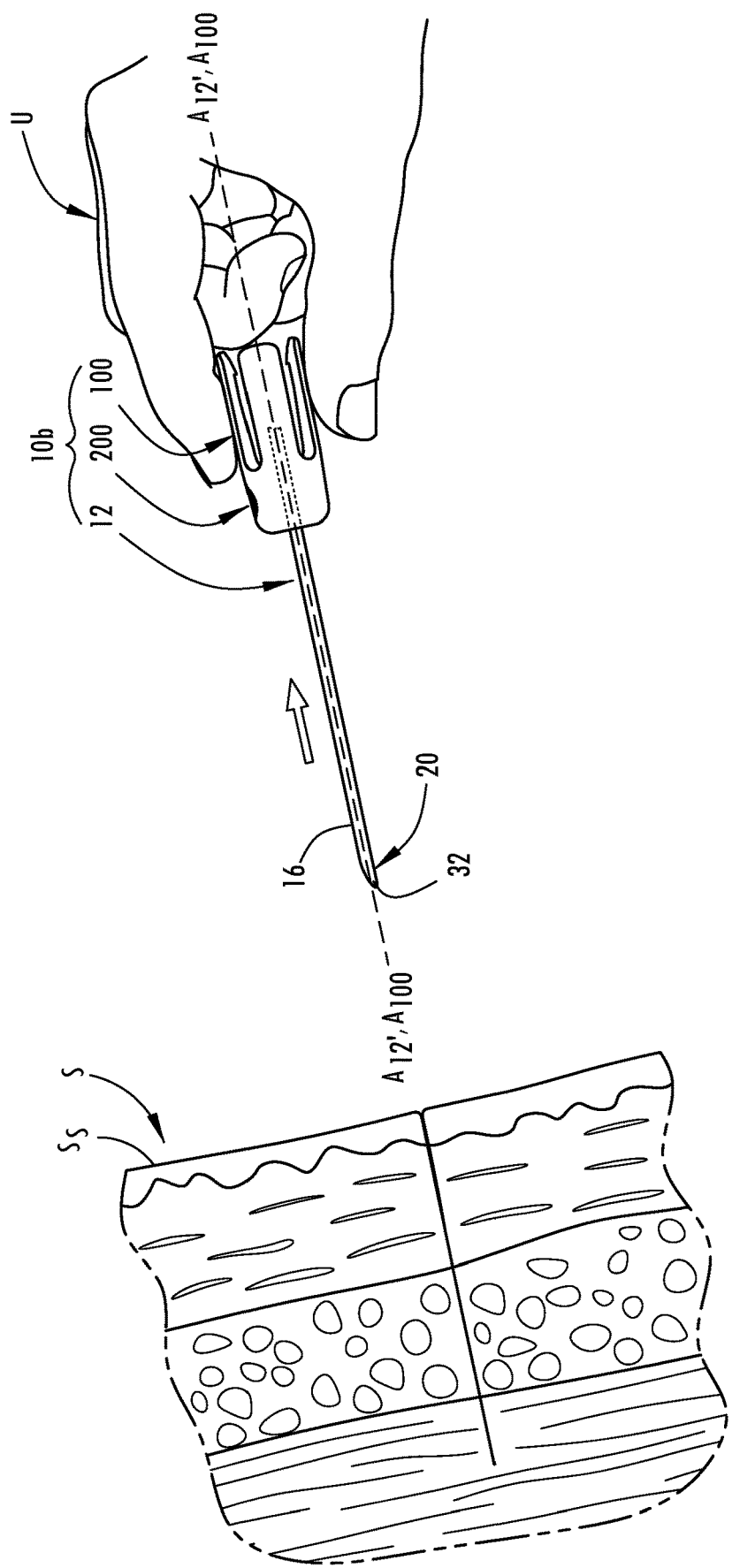
FIG. 41G is another side view of the according to FIG. 41F illustrating the user removing the second portion of the hypodermic interface assembly that was impaled within flesh of the animalia.

Thereafter, as seen at FIG. 41F, the user U may pinch or grasp the second portion 10b of the hypodermic interface assembly 10 and apply a pulling force to the second portion 10b of the hypodermic interface assembly 10 (that also includes the impaled cannula 12). As seen at FIG. 41Q as a result of the pulling force to the second portion 10b of the hypodermic interface assembly 10 by the user U, the cannula 12 is removed from the flesh of the animalia S such that the cannula 12 is not lost or would therefore otherwise undesirably remain within the flesh of the animalia S.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

The terminology used herein is for the purpose of describing particular exemplary configurations only and is not intended to be limiting. As used herein, the singular articles "a," "an," and "the" may be intended to include the plural forms as well, unless the context clearly indicates otherwise. The terms "comprises," "comprising," "including," and "having," are inclusive and therefore specify the presence of features, steps, operations, elements, and/or components, but do not preclude the presence or addition of one or more other features, steps, operations, elements, components, and/or groups thereof. The method steps, processes, and operations described herein are not to be construed as necessarily requiring their performance in the particular order discussed or illustrated, unless specifically identified as an order of performance. Additional or alternative steps may be employed.

When an element or layer is referred to as being "on," "engaged to," "connected to," "attached to," or "coupled to" another element or layer, it may be directly on, engaged, connected, attached, or coupled to the other element or layer, or intervening elements or layers may be present. In contrast, when an element is referred to as being "directly on," "directly engaged to," "directly connected to," "directly attached to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The terms first, second, third, etc. may be used herein to describe various elements, components, regions, layers and/or sections. These elements, components, regions, layers and/or sections should not be limited by these terms. These terms may be only used to distinguish one element, component, region, layer or section from another region, layer or section. Terms such as "first," "second," and other numerical terms do not imply a sequence or order unless clearly indicated by the context. Thus, a first element, component, region, layer or section discussed below could be termed a second element, component, region, layer or section without departing from the teachings of the example configurations.

What is claimed is:

1. A hypodermic interface assembly for injecting or drawing a fluid from an animalia, comprising:
    a hub having a longitudinal axis extending therethrough, an outer surface, a proximal end portion, a distal end portion, and at least one rib projecting radially outwardly away from the outer surface of the hub, wherein the at least one rib has a longitudinal length extending substantially parallel to the longitudinal axis of the hub from the proximal end portion of the hub in a direction toward the distal end portion of the hub;
    a cannula having a central axis extending therethrough; and
    a cannula carrier having a central axis extending therethrough, a head portion, at least one pair of leg portions, and a gap between the at least one pair of leg portions, wherein the gap has a length extending along the central axis of the cannula carrier
        wherein the gap and the at least one pair of leg portions of the cannula carrier extend axially along the central axis of the cannula carrier from the head portion of the cannula carrier in a direction toward the proximal end portion of the hub,
        wherein the length of the at least one rib of the hub is aligned with the length of the gap,
        wherein the cannula carrier is non-removably connected to the cannula, and
        wherein the at least one pair of leg portions of the cannula carrier is controllably separable from the hub when the animalia moves during the injecting or drawing of the fluid and the cannula is subjected to a radial force relative to the central axis of the cannula.

2. The hypodermic interface assembly of claim 1, further comprising an adhesive connecting the cannula to the cannula carrier.

3. The hypodermic interface assembly of claim 2, wherein the cannula carrier includes an adhesive-depositing passage, and wherein the adhesive is deposited into the adhesive-depositing passage of the cannula carrier.

4. The hypodermic interface assembly of claim 1, wherein each leg portion of the plurality of leg portions of the cannula carrier includes a barb portion, and wherein the hub includes a groove that is sized to receive the barb portions.

5. The hypodermic interface assembly of claim 1, wherein the cannula is disposed within:
    a hub passage extending through the hub; and
    a central passage of a body of the head portion of the cannula carrier.

6. The hypodermic interface assembly of claim 5, wherein an outer surface of the cannula is secured to an inner surface that defines the hub passage.

7. The hypodermic interface assembly of claim 5, wherein a first portion of an outer surface of the cannula is arranged in a spaced-apart relationship with respect to a first inner surface portion of the central passage of the head portion of the cannula carrier, wherein a second portion of the outer surface of the cannula is disposed adjacent a second inner surface portion of the central passage of the head portion of the cannula carrier.

8. The hypodermic interface assembly of claim 1, wherein the at least one pair of legs portions includes at least two pairs of leg portions.

9. The hypodermic interface assembly of claim 1,
    wherein the longitudinal axis of the hub is coincident with the central axis of the cannula, and
    wherein at least one leg portion of the at least one pair of leg portions is configured to move away from the longitudinal axis of the hub in response to the radial force.

10. The hypodermic interface assembly of claim 1,
    wherein the head portion of the cannula carrier is defined by a body including a central passage, the central passage extending along the central axis of the cannula carrier, and,
    wherein at least a portion of the central passage of the body of the head portion of the cannula carrier is not occupied by the hub.

11. A hypodermic interface assembly for injecting or drawing a fluid from an animalia, comprising:
    a first hypodermic interface assembly portion that is defined by:
    a hub having a longitudinal axis extending therethrough, an outer surface, a proximal end portion, a distal end portion, and at least one rib projecting radially outwardly away from the outer surface of the hub, wherein the at least one rib has a longitudinal length extending substantially parallel to the longitudinal axis of the hub from the proximal end portion of the hub in a direction toward the distal end portion of the hub; and
    a second hypodermic interface assembly portion that is separably-connected to the first hypodermic interface assembly portion, wherein the second hypodermic interface assembly portion is defined by:
        a cannula having a central axis extending therethrough; and
        a cannula carrier having a central axis extending therethrough, a head portion, at least one pair of leg portions, and a gap between the at least one pair of leg portions,
        wherein the gap and the at least one pair of leg portions of the cannula carrier extend axially along the central axis of the cannula carrier from the head portion of the cannula carrier in a direction toward the proximal end portion of the hub,
        wherein the at least one rib of the hub is in axial alignment with the gap between the at least one pair of leg portions of the cannula carrier, wherein the cannula carrier is non-removably-connected to the cannula, and wherein the at least one pair of leg portions of the cannula carrier is controllably separable from the hub when the animalia moves during the injecting or drawing of the fluid and the cannula is subjected to a radial force relative to the central axis of the cannula.

12. The hypodermic interface assembly of claim 11, further comprising an adhesive connecting the cannula to the cannula carrier.

13. The hypodermic interface assembly of claim 12, wherein the cannula carrier includes an adhesive-depositing passage, and wherein the adhesive is deposited into the adhesive-depositing passage of the cannula carrier.

14. The hypodermic interface assembly of claim 11, wherein each leg portion of the plurality of leg portions of the cannula carrier includes a barb portion, and wherein the hub includes a groove that is sized to receive the barb portions.

15. The hypodermic interface assembly of claim 11, wherein the cannula is disposed within:
a hub passage extending through the hub; and
a central passage of a body of the head portion of the cannula carrier.

16. The hypodermic interface assembly of claim 15, wherein an outer surface of the cannula is secured to an inner surface that defines the hub passage.

17. The hypodermic interface assembly of claim 15, wherein a first portion of an outer surface of the cannula is arranged in a spaced-apart relationship with respect to a first inner surface portion of the central passage of the head portion of the cannula carrier, wherein a second portion of the outer surface of the cannula is disposed adjacent a second inner surface portion of the central passage of the head portion of the cannula carrier.

18. The hypodermic interface assembly of claim 11, wherein the at least one pair of leg portions include at least two pairs of leg portions.

19. The hypodermic interface assembly of claim 11,
wherein the longitudinal axis of the hub is coincident with the central axis of the cannula, and wherein at least one leg portion of the at least one pair of leg portions is configured to move away from the longitudinal axis of the hub in response to the radial force.

20. The hypodermic interface assembly of claim 11,
wherein the head portion of the cannula carrier is defined by a body including a central passage, the central passage extending along the central axis of the cannula carrier, and, wherein at least a portion of the central passage of the body of the head portion of the cannula carrier is not occupied by the hub.

21. A method for injecting or drawing a fluid from an animalia comprising:
providing the hypodermic interface assembly of claim 1;
separably joining the hub to an injection gun; and
inserting the cannula into the flesh of an animalia.

22. The method of claim 21:
wherein when the cannula is subjected to the radial force relative to a central axis of the cannula, the cannula carrier is mechanically separated from the hub whereby:
the hub remains separably joined to the injection gun; and
the cannula is removably disposed within flesh of the animalia and the cannula carrier is disposed adjacent an outer surface of the flesh of the animalia.

23. The method of claim 22 further comprising:
locating the cannula carrier that is disposed adjacent the outer surface of the flesh of the animalia;
grasping the cannula carrier; and
applying a force to the cannula carrier to remove the cannula from the flesh of the animalia.

24. The method of claim 22, wherein the cannula carrier includes a high visibility dye or pigment.

25. The method of claim 22, wherein the radial force relative to a central axis of the cannula results in splaying one or more leg portions of the at least one pair of leg portions of the cannula carrier.

26. The method of claim 22 further comprising:
separating the hub from the injection gun.

* * * * *